(12) United States Patent
Marks et al.

(10) Patent No.: US 11,505,598 B2
(45) Date of Patent: Nov. 22, 2022

(54) ANTIBODIES TO BOTULINUM NEUROTOXINS

(71) Applicant: The Regents of the University of California, Oakland, CA (US)

(72) Inventors: James D. Marks, San Francisco, CA (US); Maria Consuelo Garcia Rodriguez, San Francisco, CA (US); Jianbo Dong, San Francisco, CA (US); Zhengda Sun, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 36 days.

(21) Appl. No.: 16/259,418

(22) Filed: Jan. 28, 2019

(65) Prior Publication Data

US 2019/0256584 A1 Aug. 22, 2019

Related U.S. Application Data

(60) Provisional application No. 62/624,035, filed on Jan. 30, 2018.

(51) Int. Cl.
| | | |
|---|---|---|
| *C07K 16/12* | (2006.01) | |
| *A61P 31/04* | (2006.01) | |
| *G01N 33/533* | (2006.01) | |
| *G01N 33/563* | (2006.01) | |
| *G01N 33/569* | (2006.01) | |
| *G01N 33/549* | (2006.01) | |

(52) U.S. Cl.
CPC .......... *C07K 16/1282* (2013.01); *A61P 31/04* (2018.01); *G01N 33/533* (2013.01); *G01N 33/549* (2013.01); *G01N 33/563* (2013.01); *G01N 33/56911* (2013.01)

(58) Field of Classification Search
None
See application file for complete search history.

(56) References Cited

U.S. PATENT DOCUMENTS

| | | |
|---|---|---|
| 9,000,131 B2 | 4/2015 | Marks et al. |
| 9,181,330 B2 | 11/2015 | Marks et al. |
| 9,243,057 B2 | 1/2016 | Marks et al. |
| 9,453,068 B2 | 9/2016 | Marks et al. |
| 9,902,780 B2 | 2/2018 | Marks et al. |
| 9,902,781 B2 | 2/2018 | Marks et al. |
| 2014/0105910 A1 | 4/2014 | Marks et al. |
| 2015/0030600 A1 | 1/2015 | Marks et al. |
| 2015/0197559 A1 | 7/2015 | Marks et al. |
| 2016/0168265 A1 | 6/2016 | Marks et al. |
| 2016/0229921 A1 | 8/2016 | Marks et al. |
| 2017/0096474 A1 | 4/2017 | Marks et al. |
| 2018/0208679 A1 | 7/2018 | Marks et al. |
| 2018/0208680 A1 | 7/2018 | Marks et al. |

OTHER PUBLICATIONS

Skolnick et al. (Trends in Biotechnology 18: 34-39, 2000).*
Greenspan et al. (Nature Biotechnology 7: 936-937, 1999).*
Giusti et al. (Proc. Natl. Acad. Sci. USA. May 1987; 84 (9): 2926-2930).*
Winkler et al (J. Imm., 265:4505-4514, 2000).*
Chien et al. (Proc. Natl. Acad. Sci. USA. Jul. 1989; 86 (14): 5532-5536).*
Caldas et al. (Mol. Immunol. May 2003; 39 (15): 941-952).*
Casadevall et al. (PNAS vol. 109 No. 31, pp. 12272-12273).*
Sela-Culang et al. (Frontiers in Immunology, 2013 vol. 4, article 302, pp. 1-13).*
ClinicalTrials.gov; "Study to Evaluate Safety and PK of NTM-1634 vs Placebo Administered Intravenously in Healthy Adults"; 5 pages (May 1, 2017).

* cited by examiner

*Primary Examiner* — Robert A Zeman
(74) *Attorney, Agent, or Firm* — Bozicevic, Field & Francis LLP; Shweta Chandra

(57) ABSTRACT

The present disclosure provides antibodies that specifically bind to botulinum neurotoxins. The antibodies and derivatives thereof that specifically bind to the neutralizing epitopes provided herein can be used in methods to specifically bind and, in some embodiments, neutralize, botulinum neurotoxin and are therefore also useful in the treatment.

14 Claims, 8 Drawing Sheets

Specification includes a Sequence Listing.

Figure 1

| Clone VH | Framework 1 | CDR1 | Framework 2 | CDR2 |
|---|---|---|---|---|
| 4C10.5 | QVQLVQSGGGVVQPGRSLRLSCGASRFTFS (SEQ ID NO:1) | GFDMH (SEQ ID NO:4) | WVRQAPGKGLEWVA (SEQ ID NO:5) | RISHDGSMADYADSLRG (SEQ ID NO:6) |
| 4C10.8 | QVQLVQSGGGVVQPGRSLRLSCGASRFTFS (SEQ ID NO:1) | GFDMH (SEQ ID NO:4) | WVRQAPGKGLEWVA (SEQ ID NO:5) | RISHDGSMADYADSLRG (SEQ ID NO:6) |
| 4C10.15 | QVQLVQSGGGVVQPGRSLRLSCGASRFTFS (SEQ ID NO:1) | GFDMH (SEQ ID NO:4) | WVRQAPGKGLEWVA (SEQ ID NO:5) | RISHDGSMADYADSLRG (SEQ ID NO:6) |
| 4C10.17 | QVQLVQSGGGVAQPGRSLRLSCGASRFTFS (SEQ ID NO:1) | GFDMH (SEQ ID NO:4) | WVRQAPGKGLEWVA (SEQ ID NO:5) | RISHDGSMADYADSLRG (SEQ ID NO:6) |
| 4C10.18 | QVQLVQSGGGVVQPGRSLRLSCGASRFTFS (SEQ ID NO:2) | GFDMH (SEQ ID NO:4) | WVRQAPGKGLEWVA (SEQ ID NO:5) | RISHDGSMADYADSLRG (SEQ ID NO:6) |
| 4C10.20 | QVQLVQSGGGVVQPGRSLRLSCGASRFTFS (SEQ ID NO:1) | GFDMH (SEQ ID NO:4) | WVRQAPGKGLEWVA (SEQ ID NO:5) | RISHDGSMADYADSLRG (SEQ ID NO:6) |
| 4C10.22 | QVQLVQSGGGVVQPGRSLRLSCGASGFKFS (SEQ ID NO:3) | GFDMH (SEQ ID NO:4) | WVRQAPGKGLEWVA (SEQ ID NO:5) | RISHDGSMADYADSLRG (SEQ ID NO:6) |

| Clone VH | Framework 3 | CDR3 | Framework 4 |
|---|---|---|---|
| 4C10.5 | RFTISRDNSKNTLYLQMNSLRVEDTALYYCAK (SEQ ID NO:7) | DRWRSGSYPAFEI (SEQ ID NO:8) | WGQGTMVTVSS (SEQ ID NO:10) |
| 4C10.8 | RFTISRDNSKNTLYLQMNSLRVEDTALYYCAK (SEQ ID NO:7) | DPWRSGSYPAFEI (SEQ ID NO:9) | WGQGTMVTVSS (SEQ ID NO:10) |
| 4C10.15 | RFTISRDNSKNTLYLQMNSLRVEDTALYYCAK (SEQ ID NO:7) | DRWRSGSYPAFEI (SEQ ID NO:8) | WGQGTMVTVSS (SEQ ID NO:10) |
| 4C10.17 | RFTISRDNSKNTLYLQMNSLRVEDTALYYCAK (SEQ ID NO:7) | DRWRSGSYPAFEI (SEQ ID NO:8) | WGQGTMVTVSS (SEQ ID NO:10) |
| 4C10.18 | RFTISRDNSKNTLYLQMNSLRVEDTALYYCAK (SEQ ID NO:7) | DRWRSGSYPAFEI (SEQ ID NO:8) | WGQGTMVTVSS (SEQ ID NO:10) |
| 4C10.20 | RFTISRDNSKNTLYLQMNSLRVEDTALYYCAK (SEQ ID NO:7) | DPWRSGSYPAFEI (SEQ ID NO:9) | WGQGTMVTVSS (SEQ ID NO:10) |
| 4C10.22 | RFTISRDNSKNTLYLQMNSLRVEDTALYYCAK (SEQ ID NO:7) | DPWRSGSYPAFEI (SEQ ID NO:9) | WGQGTMVTVSS (SEQ ID NO:10) |

| Clone VL | Framework 1 | CDR1 | Framework 2 | CDR2 |
|---|---|---|---|---|
| 4C10.5 | EIVLTQSPSFLSAFVGDRITITC (SEQ ID NO:11) | RASQGISNRLA (SEQ ID NO:13) | WYQQKPGKAPNLLIHP (SEQ ID NO:16) | ASTLQS (SEQ ID NO:18) |
| 4C10.8 | EIVLTQSPSFLSAFIGDRITITC (SEQ ID NO:12) | RASQGISNRLA (SEQ ID NO:13) | WYQQKPGKAPNLLIYP (SEQ ID NO:17) | ASTLQS (SEQ ID NO:18) |
| 4C10.15 | EIVLTQSPSFLSAFVGDRITITC (SEQ ID NO:11) | RASKGISNRLA (SEQ ID NO:14) | WYQQKPGKAPNLLIHP (SEQ ID NO:16) | ASTLQS (SEQ ID NO:18) |
| 4C10.17 | EIVLTQSPSFLSAFVGDRITITC (SEQ ID NO:11) | RASQGISNRLA (SEQ ID NO:13) | WYQQKPGKAPNLLIHP (SEQ ID NO:16) | ASSLQS (SEQ ID NO:19) |
| 4C10.18 | EIVLTQSPSFLSAFIGDRITITC (SEQ ID NO:12) | RASQGIGNRLA (SEQ ID NO:15) | WYQQKPGKAPNLLIYP (SEQ ID NO:17) | ASTLQS (SEQ ID NO:18) |
| 4C10.20 | EIVLTQSPSFLSAFIGDRITITC (SEQ ID NO:12) | RASQGISNRLA (SEQ ID NO:13) | WYQQKPGKAPNLLIYP (SEQ ID NO:17) | ASTLQS (SEQ ID NO:18) |
| 4C10.22 | EIVLTQSPSFLSAFIGDRITITC (SEQ ID NO:12) | RASQGISNRLA (SEQ ID NO:13) | WYQQKPGKAPNLLIYP (SEQ ID NO:17) | ASTLQS (SEQ ID NO:18) |

| Clone VL | Framework 3 | CDR3 | Framework 4 |
|---|---|---|---|
| 4C10.5 | GVPSRFSGSGSGTDFTLTISSLQPEDFATYYC (SEQ ID NO:20) | QQANSFPLT (SEQ ID NO:21) | FGGGTKVEIKR (SEQ ID NO:46) |
| 4C10.8 | GVPSRFSGSGSGTDFTLTISSLQPEDFATYYC (SEQ ID NO:20) | QQANSFPLT (SEQ ID NO:21) | FGGGTKVEIKR (SEQ ID NO:46) |
| 4C10.15 | GVPSRFSGSGSGTDFTLTISSLQPEDFATYYC (SEQ ID NO:20) | QQANSFPLT (SEQ ID NO:21) | FGGGTKVEIKR (SEQ ID NO:46) |
| 4C10.17 | GVPSRFSGSGSGTDFTLTISSLQPEDFATYYC (SEQ ID NO:20) | QQANSFPLT (SEQ ID NO:21) | FGGGTKVEIKR (SEQ ID NO:46) |
| 4C10.18 | GVPSRFSGSGSGTDFTLTISSLQPEDFATYYC (SEQ ID NO:20) | QQAHRFPLT (SEQ ID NO:22) | FGGGTKVEIKR (SEQ ID NO:46) |
| 4C10.20 | GVPSRFSGSGSGTDFTLTISSLQPEDFATYYC (SEQ ID NO:20) | QQANSFPLT (SEQ ID NO:21) | FGGGTKVEIKR (SEQ ID NO:46) |
| 4C10.22 | GVPSRFSGSGSGTDFTLTISSLQPEDFATYYC (SEQ ID NO:20) | QQANSFPLT (SEQ ID NO:21) | FGGGTKVEIKR (SEQ ID NO:46) |

Figure 2

Clone: 4C10.5

VH:
QVQLVQSGGGVVQPGRSLRLSCGASRFTFSGFDMHWVRQAPGKGLEWVARISHDGSMADYADSLRGRFTISRDNSKNTLYLQMNSLRVEDTALYYCAKDRWRSGSYPAFEIWGQGTMVTVSS (SEQ ID NO:23)

VL:
EIVLTQSPSFLSAFVGDRITITCRASQGISNRLAWYQQKPGKAPNLLIHPASTLQSGVPSRFSGSGSGTDFTLTISSLQPEDFATYYCQQANSFPLTFGGGTKVEIKR (SEQ ID NO:24)

Full Sequence:
QVQLVQSGGGVVQPGRSLRLSCGASRFTFSGFDMHWVRQAPGKGLEWVARISHDGSMADYADSLRGRFTISRDNSKNTLYLQMNSLRVEDTALYYCAKDRWRSGSYPAFEIWGQGTMVTVSSEIVLTQSPSFLSAFVGDRITITCRASQGISNRLAWYQQKPGKAPNLLIHPASTLQSGVPSRFSGSGSGTDFTLTISSLQPEDFATYYCQQANSFPLTFGGGTKVEIKR (SEQ ID NO:25)

Clone: 4C10.8

VH:
QVQLVQSGGGVVQPGRSLRLSCGASRFTFSGFDMHWVRQAPGKGLEWVARISHDGSMADYADSLRGRFTISRDNSKNTLYLQMNSLRVEDTALYYCAKDPWRSGSYPAFEIWGQGTMVTVSS (SEQ ID NO:26)

VL:
EIVLTQSPSFLSAFIGDRITITCRASQGISNRLAWYQQKPGKAPNLLIYPASTLQSGVPSRFSGSGSGTDFTLTISSLQPEDFATYYCQQANSFPLTFGGGTKVEIKR (SEQ ID NO:27)

Full Sequence:
QVQLVQSGGGVVQPGRSLRLSCGASRFTFSGFDMHWVRQAPGKGLEWVARISHDGSMADYADSLRGRFTISRDNSKNTLYLQMNSLRVEDTALYYCAKDPWRSGSYPAFEIWGQGTMVTVSSEIVLTQSPSFLSAFIGDRITITCRASQGISNRLAWYQQKPGKAPNLLIYPASTLQSGVPSRFSGSGSGTDFTLTISSLQPEDFATYYCQQANSFPLTFGGGTKVEIKR (SEQ ID NO:28)

Figure 2 CONTINUED

Clone: 4C10.15
VH:
QVQLVQSGGGVVQPGRSLRLSCGASRFTFSGFDMHWVRQAPGKGLEWVARISHDGSMADYADSLRGRFTISRDNSKNTLYLQMNSLRVEDTALYYCAKDRWRSGSYPAFEIWGQGTMVTVSS (SEQ ID NO:23)

VL:
EIVLTQSPSFLSAFVGDRITITCRASKGIGNRLAWYQQKPGKAPNLLIHPASTLQSGVPSRFSGSGSGTDFTLTISSLQPEDFATYYCQQANSFPLTFGGGTKVEIKR (SEQ ID NO:29)

Full Sequence:
QVQLVQSGGGVVQPGRSLRLSCGASRFTFSGFDMHWVRQAPGKGLEWVARISHDGSMADYADSLRGRFTISRDNSKNTLYLQMNSLRVEDTALYYCAKDRWRSGSYPAFEIWGQGTMVTVSSEIVLTQSPSFLSAFVGDRITITCRASKGIGNRLAWYQQKPGKAPNLLIHPASTLQSGVPSRFSGSGSGTDFTLTISSLQPEDFATYYCQQANSFPLTFGGGTKVEIKR (SEQ ID NO:30)

Clone: 4C10.17
VH:
QVQLVQSGGGVVQPGRSLRLSCGASRFTFSGFDMHWVRQAPGKGLEWVARISHDGSMADYADSLRGRFTISRDNSKNTLYLQMNSLRVEDTALYYCAKDRWRSGSYPAFEIWGQGTMVTVSS (SEQ ID NO:23)

VL:
EIVLTQSPSFLSAFVGDRITITCRASQGISNRLAWYQQKPGKAPNLLIHPASSLQSGVPSRFSGSGSGTDFTLTISSLQPEDFATYYCQQANSFPLTFGGGTKVEIKR (SEQ ID NO:31)

Full Sequence:
QVQLVQSGGGVVQPGRSLRLSCGASRFTFSGFDMHWVRQAPGKGLEWVARISHDGSMADYADSLRGRFTISRDNSKNTLYLQMNSLRVEDTALYYCAKDRWRSGSYPAFEIWGQGTMVTVSSEIVLTQSPSFLSAFVGDRITITCRASQGISNRLAWYQQKPGKAPNLLIHPASSLQSGVPSRFSGSGSGTDFTLTISSLQPEDFATYYCQQANSFPLTFGGGTKVEIKR (SEQ ID NO:32)

Figure 2 CONTINUED

Clone: 4C10.18

VH:
QVQLVQSGGGVAQPGRSLRLSCGASRFTFSGFDMHWVRQAPGKGLEWVARISHDGSMADYADSLRGRFTISRDNSKNTLYLQMNSLRVEDTALYYCAKDRWRSGSYPAFEIWGQGTMVTVSS (SEQ ID NO:33)

VL:
EIVLTQSPSFLSAFVGDRITITCRASQGIGNRLAWYQQKPGKAPNLLIHPASTLQSGVPSRFSGSGSGTDFTLTISSLQPEDFATYYCQQAHRFPLTFGGGTKVEIKR (SEQ ID NO:34)

Full Sequence:
QVQLVQSGGGVAQPGRSLRLSCGASRFTFSGFDMHWVRQAPGKGLEWVARISHDGSMADYADSLRGRFTISRDNSKNTLYLQMNSLRVEDTALYYCAKDRWRSGSYPAFEIWGQGTMVTVSSEIVLTQSPSFLSAFVGDRITITCRASQGIGNRLAWYQQKPGKAPNLLIHPASTLQSGVPSRFSGSGSGTDFTLTISSLQPEDFATYYCQQAHRFPLTFGGGTKVEIKR (SEQ ID NO:35)

Clone: 4C10.20

VH:
QVQLVQSGGGVVQPGRSLRLSCGASRFTFSGFDMHWVRQAPGKGLEWVARISHDGSMADYADSLRGRFTISRDNSKNTLYLQMNSLRVEDTALYYCAKDPWRSGSYPAFEIWGQGTMVTVSS (SEQ ID NO:26)

VL:
EIVLTQSPSFLSAFIGDRITITCRASQGIGNRLAWYQQKPGKAPNLLIYPASTLQSGVPSRFSGSGSGTDFTLTISSLQPEDFATYYCQQANSFPLTFGGGTKVEIKR (SEQ ID NO:36)

Full Sequence:
QVQLVQSGGGVVQPGRSLRLSCGASRFTFSGFDMHWVRQAPGKGLEWVARISHDGSMADYADSLRGRFTISRDNSKNTLYLQMNSLRVEDTALYYCAKDPWRSGSYPAFEIWGQGTMVTVSSEIVLTQSPSFLSAFIGDRITITCRASQGIGNRLAWYQQKPGKAPNLLIYPASTLQSGVPSRFSGSGSGTDFTLTISSLQPEDFATYYCQQANSFPLTFGGGTKVEIKR (SEQ ID NO:37)

Figure 2 CONTINUED

Clone: 4C10.22

VH:
QVQLVQSGGGVVQPGRSLRLSCGASGFKFSGFDMHWVRQAPGKGLEWVARISHDGSMADYADSLRGRFTISRDNSKNTLYLQMNSLRVEDTALYYCAKDPWRSGSYPAFEIWGQGTMVTVSS (SEQ ID NO:38)

VL:
EIVLTQSPSFLSAFIGDRITITCRASQGISNRLAWYQQKPGKAPNLLIYPASTLQSGVPSRFSGSGSGTDFTLTISSLQPEDFATYYCQQANSFPLTFGGGTKVEIKR (SEQ ID NO:27)

Full Sequence:
QVQLVQSGGGVVQPGRSLRLSCGASGFKFSGFDMHWVRQAPGKGLEWVARISHDGSMADYADSLRGRFTISRDNSKNTLYLQMNSLRVEDTALYYCAKDPWRSGSYPAFEIWGQGTMVTVSSEIVLTQSPSFLSAFIGDRITITCRASQGISNRLAWYQQKPGKAPNLLIYPASTLQSGVPSRFSGSGSGTDFTLTISSLQPEDFATYYCQQANSFPLTFGGGTKVEIKR (SEQ ID NO:39)

Figure 3: DNA and Corresponding Amino Acid Sequence of 4C10.20 Light Chain

```
        M   D   M   R   V   P   A   Q   L   L   G   L   L   L   L   W   L   P   G   A
   1   ATG GAC ATG CGT GTG CCT GCC CAG CTT CTG GGG CTC TTG CTG CTC TGG CTG CCA GGA GCT

R   C   +1E  I   V   L   T   Q   S   P   S   F   L   S   A   F   I   G   D   R
  61   AGA TGC GAA ATC GTT CTT ACA CAA TCT CCA TCC TTC CTG AGT GCC TTT ATC GGT GAT AGA

I   T   I   T   C   R   A   S   Q   G   I   G   N   R   L   A   W   Y   Q   Q
 121   ATC ACA ATC ACC TGC CGT GCT TCA CAG GGT ATT GGC AAC AGG CTG GCC TGG TAT CAG CAG

K   P   G   K   A   P   N   L   L   I   Y   P   A   S   T   L   Q   S   G   V
 181   AAA CCC GGC AAA GCA CCT AAT TTG CTG ATC TAC CCA GCC AGT ACA CTG CAG AGT GGC GTA

P   S   R   F   S   G   S   G   S   G   T   D   F   T   L   T   I   S   S   L
 241   CCA TCT CGC TTT AGC GGG TCC TCT GGC ACT GAT TTT ACA CTG ACC ATA TCA AGC CTG

Q   P   E   D   F   A   T   Y   Y   C   Q   Q   A   N   S   F   P   L   T   F
 301   CAG CCA GAG GAT TTC GCC ACC TAT TAT TGT CAA CAA GCA AAC TCC TTC CCC CTG ACC TTC

G   G   G   T   K   V   E   I   K   R   T   V   A   A   P   S   V   F   I   F
 361   GGA GGT GGA ACA AAA GTG GAG ATT AAG CGT ACG GTG GCT GCA CCA TCT GTC TTC ATC TTC

P   P   S   D   E   Q   L   K   S   G   T   A   S   V   V   C   L   L   N   N
 421   CCG CCA TCT GAT GAG CAG TTG AAA TCT GGA ACT GCC TCT GTT GTG TGC CTG CTG AAT AAC

F   Y   P   R   E   A   K   V   Q   W   K   V   D   N   A   L   Q   S   G   N
 481   TTC TAT CCC AGA GAG GCC AAA GTA CAG TGG AAG GTG GAT AAC GCC CTC CAA TCG GGT AAC

S   Q   E   S   V   T   E   Q   D   S   K   D   S   T   Y   S   L   S   S   T
 541   TCC CAG GAG AGT GTC ACA GAG CAG GAC AGC AAG GAC AGC ACC TAC AGC CTC AGC ACC

L   T   L   S   K   A   D   Y   E   K   H   K   V   Y   A   C   E   V   T   H
 601   CTG ACG CTG AGC AGC TCG CCC GTC ACA GCA GAC TAC GAG AAA CAC AAA GTC TAC GCC TGC GAA GTC ACC CAT

Q   G   L   S   S   P   V   T   K   S   F   N   R   G   E   C   .
 661   CAG GGC CTG AGC TCG CCC GTC ACA AAG AGC TTC AAC AGG GGA GAG TGT TAG
```

Figure 4: DNA and Corresponding Amino Acid Sequence of 4C10.20 Heavy Chain

ANTIBODIES TO BOTULINUM NEUROTOXINS

CROSS-REFERENCE

This application claims the benefit of U.S. Provisional Patent Application No. 62/624,035, filed Jan. 30, 2018, which application is incorporated herein by reference in its entirety.

STATEMENT AS TO FEDERALLY SPONSORED RESEARCH

This invention was made with government support under Grant No. AI075443 awarded by the National Institutes of Health, Grant No. HDTRA1-07-1-0030 awarded by the Department of Defense, Defense Threat Reduction Agency, and Grant No. 200-2006-16697 awarded by the Centers for Disease Control. The government has certain rights in the invention.

INCORPORATION BY REFERENCE OF SEQUENCE LISTING PROVIDED AS A TEXT FILE

A Sequence Listing is provided herewith as a text file, "UCSF-551_SEQ_LISTING_ST25.txt" created on Jan. 11, 2019 and having a size of 32 KB. The contents of the text file are incorporated by reference herein in their entirety.

INTRODUCTION

Botulism is caused by botulinum neurotoxin secreted by members of the genus Clostridium and is characterized by flaccid paralysis, which if not immediately fatal requires prolonged hospitalization in an intensive care unit and mechanical ventilation. Naturally occurring botulism is found in infants or adults whose gastrointestinal tracts become colonized by Clostridial bacteria (infant or intestinal botulism), after ingestion of contaminated food products (food botulism), or in anaerobic wound infections (wound botulism) (Center for Disease Control (1998) Botulism in the United States, 1899-1998. Handbook for epidemiologists, clinicians, and laboratory workers. Atlanta, Ga. U.S. Department of Health and Human Services, Public Health Service: downloadable at "bt(dot)cdc(dot)gov/agent/botulism/index(dot)asp"). Botulinum neurotoxins (BoNTs) are also classified by the Centers for Disease Control (CDC) as one of the six highest-risk threat agents for bioterrorism (the "Category A agents"), due to their extreme potency and lethality, ease of production and transport, and need for prolonged intensive care (Arnon et al. (2001) JAMA 285: 1059-1070). As a result of these threats, specific pharmaceutical agents are needed for prevention and treatment of intoxication.

No specific small molecule drugs exist for prevention or treatment of botulism, but an investigational pentavalent toxoid vaccine is available from the CDC (Siegel (1988) J. Clin. Microbiol.26: 2351-2356) and a recombinant vaccine is under development (Smith (1998) Toxicon 36: 1539-1548). Regardless, mass civilian or military vaccination is unlikely due to the rarity of disease or exposure and the fact that vaccination would prevent subsequent medicinal use of BoNT. Toxin neutralizing antibody (Ab) can be used for pre- or post-exposure prophylaxis or for treatment (Franz et al. (1993) Pp. 473-476 In B. R. DasGupta (ed.), Botulinum and Tetanus Neurotoxins: Neurotransmission and Biomedical Aspects. Plenum Press, New York) Small quantities of both equine antitoxin and human botulinum immune globulin exist and are currently used to treat adult (Black and Gunn. (1980) Am. J. Med., 69: 567-570; Hibbs et al. (1996) Clin. Infect. Dis., 23: 337-340) and infant botulism (Arnon (1993). Clinical trial of human botulism immune globulin, p. 477-482. In B. R. DasGupta (ed.), Botulinum and Tetanus Neurotoxins: Neurotransmission and Biomedical Aspects. Plenum Press, New York) respectively. Currently existing equine antitoxins include Botulism Antitoxin Heptavalent (A,B,C,D,E,F,G)—Equine (BAT), which is an FDA-Approved CDC stock for Anti-BoNT treatment following documented or suspective exposure to botulinum neurotoxin serotypes in adults and pediatric patients (Center for Biologics Evaluation and Research, Cangene Corporation, and U.S. Food and Drug Administration. "Fractionated Plasma Products-BAT (Botulism Antitoxin Heptavalent (A, B, C, D, E, F, G)—(Equine)." U.S. Food and Drug Administration Home Page. Center for Biologics Evaluation and Research, 16 Jul. 2016).

The development of monoclonal antibody (mAb) therapy for botulism is complicated by the fact that there are at least seven BoNT serotypes (A-G) (Hatheway (1995) Curr. Top. Microbio. Immunol, 195: 55-75) that show little, if any, antibody cross-reactivity. While only four of the BoNT serotypes routinely cause human disease (A, B, E, and F), there has been one reported case of infant botulism caused by BoNT/C (Oguma et al. (1990) Lancet 336: 1449-1450), one outbreak of foodborne botulism linked to BoNT/D (Demarchi, et al. (1958) Bull. Acad. Nat. Med., 142: 580-582), and several cases of suspicious deaths where BoNT/G was isolated (Sonnabend et al. (1981) J. Infect. Dis., 143: 22-27). Aerosolized BoNT/C, D, and G have also been shown to produce botulism in primates by the inhalation route (Middlebrook and Franz (1997) Botulinum Toxins, chapter 33. In F. R. Sidell, E. T. Takafuji, D. R. Franz (eds.), Medical Aspects of Chemical and Biological Warfare. TMM publications, Washington, D.C.), and would most likely also affect humans. Thus, it is likely that any one of the seven BoNT serotypes can be used as a biothreat agent.

Variability of the BoNT gene and protein sequence within serotypes has also been reported and there is evidence that such variability can affect the binding of monoclonal antibodies to BoNT/A (Kozaki et al. (1998) Infect. Immun, 66: 4811-4816; Kozaki et al. (1995) Microbiol. Immunol., 39: 767-774).

SUMMARY

The present disclosure provides antibodies that specifically bind to botulinum neurotoxins. The antibodies and derivatives thereof that specifically bind to the neutralizing epitopes provided herein can be used in methods to specifically bind and, in some embodiments, neutralize, botulinum neurotoxin and are therefore also useful in the treatment.

Antibodies that bind to and neutralize and/or otherwise clear botulinum neurotoxin(s) are disclosed herein. Particularly effective neutralization of a BoNT serotype can be achieved by the use of neutralizing antibodies that bind two or more subtypes of the particular neurotoxin serotype with particularly high affinity and/or by combinations of such antibodies. The present disclosure provides antibodies that bind BoNT serotypes BoNT/C, BoNT/D, BoNT/CD, BoNT/DC, as well as subtypes thereof. BoNT subtypes include but are not limited to pure BoNT/C. BoNT mosaics include BoNT/CD and BoNT/DC. Compositions comprising neutralizing antibodies that bind two or more BoNT subtypes (e.g., BoNT/C, BoNT/C, BoNT/D, BoNT/DC, etc.) with high affinity are also provided herein.

An antibody for Botulinum neurotoxin (BoNT) is provided herein. The antibody typically comprises at least one VH complementarity determining region (CDR) selected from an antibody from a clone listed in FIG. 1 or FIG. 2, and/or at least one VL complementarity determining region selected from an antibody from a clone listed in FIG. 1.

The antibody may be a single chain Fv (scFv), a Fab, a (Fab')2, an (ScFv)2, and the like. The antibody may be an IgG. The antibody may also be in a pharmaceutically acceptable excipient (e.g., in a unit dosage formulation).

Methods of inhibiting and/or neutralizing the activity of BoNT in a mammal may involve administering to a mammal in need thereof a composition comprising at least one neutralizing anti-BoNT antibody as described herein. The composition may include at least two different antibodies, each of which binds to different BoNT subtypes. The composition may also include at least three, at least four, or more different antibodies, each of which may bind to different BoNT epitopes.

Compositions provided herein may specifically bind to a BoNT. The compositions typically include a first antibody that binds one or more serotypes, e.g., one or more antibodies as described above, can optionally include a second antibody, a third antibody, or a fourth antibody, or more that bind one or more BoNT serotypes.

Nucleic acids provided herein encode one or more antibodies that are described herein. Cells containing such nucleic acids are also provided herein. Kits provided for neutralizing a BoNT may include a composition containing one or more antibodies as described herein. The kits optionally also include instructional materials teaching the use of the composition to specifically bind to a BoNT. The composition may be stored in a disposable syringe.

BRIEF DESCRIPTION OF THE DRAWINGS

FIG. 1 Amino acid sequences of the variable heavy chain region and variable light chain region of monoclonal antibodies 4C10.5, 4C10.8, 4C10.15, 4C10.17, 4C10.18, 4C10.20, and 4C10.22.

FIG. 2. Amino acid sequences of monoclonal antibodies 4C10.5, 4C10.8, 4C10.15, 4C10.17, 4C10.18, 4C10.20, and 4C10.22.

FIG. 3. DNA (SEQ ID NO: 47) and corresponding amino acid sequence (SEQ ID NO: 48) of 4C10.20 light chain. The start of the mature variable (V) region sequence is shown as +1.

FIG. 4. DNA (SEQ ID NO: 49) and corresponding amino acid sequence (SEQ ID NO: 50) of 4C10.20 heavy chain. The start of the mature variable (V) region sequence is shown as +1.

DEFINITIONS

Figure 5:
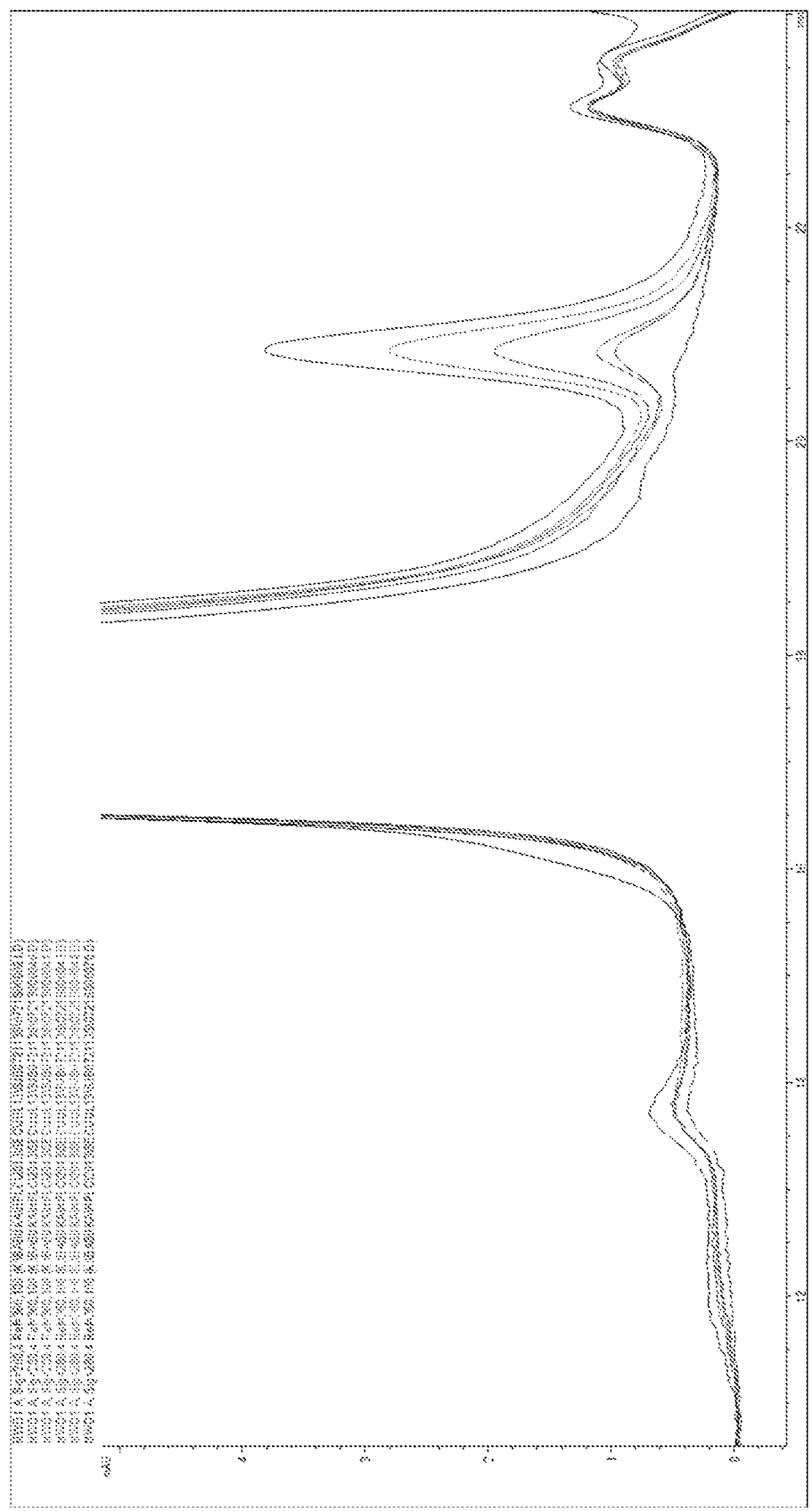
FIG. 5. Chromatographic overlay of 4C10.20 showing gradual decrease in percent aggregate (small peak infront of main peak) for samples stored a 50° C.

A "BoNT polypeptide" refers to a Botulinum neurotoxin polypeptide (e.g., a BoNT/A polypeptide, a BoNT/B polypeptide, a BoNT/C polypeptide, and so forth). The BoNT polypeptide can refer to a full-length polypeptide or to a fragment thereof. Thus, for example, the term "BoNT/C polypeptide" refers to either a full-length BoNT/C (a neurotoxin produced by Clostridium botulinum of the type C serotype) or a fragment thereof (e.g. the HC fragment). The HC fragment of BoNT/A is an approximately 50 kDa C-terminal fragment (residues 873-1296) of BoNT/A (Lacy and Stevens (1999) J. Mol. Biol., 291: 1091-1104).

A "BoNT serotype" refers one of the standard known BoNT serotypes (e.g. BoNT/A, BoNT/B, BoNT/C, BoNT/D, etc.).

The term "BoNT subtype" refers to botulinum neurotoxin gene sequences of a particular serotype (e.g., A, B, C, D, E, F, G etc.) that differ from each other sufficiently to produce differential antibody binding.

A "mosaic BoNT", as used herein, refers to a BoNT polypeptide that contains at least two contiguous amino acid sequences, each of which is derived from a different serotype or subtype.

"Derived from" in the context of an amino acid sequence or polynucleotide sequence (e.g., an amino acid sequence "derived from" BoNT/C) is meant to indicate that the polypeptide or nucleic acid has a sequence that is based on that of a reference polypeptide or nucleic acid (e.g., a naturally occurring BoNT/C or encoding nucleic acid), and is not meant to be limiting as to the source or method in which the protein or nucleic acid is made.

An "anti-BoNT antibody" refers to an antibody that binds a BoNT polypeptide, specifically binds a BoNT polypeptide with a $K_D$ less than about $10^{-7}$, less than about $10^{-8}$, less than about $10^{-9}$, less than about $10^{-10}$, less than about $10^{-11}$, or less than about $10^{12}$ or less. In certain embodiments, "high affinity" antibodies have a $K_D$ of 5 nM or less.

"Neutralization" refers to a measurable decrease in the toxicity and/or circulating level of a Botulinum neurotoxin (e.g., BoNT/C) in in vitro testing, animals, or human patient.

By "treatment" it is meant that at least an amelioration of the symptoms associated with the condition afflicting the host is achieved, where amelioration refers to at least a reduction in the magnitude of a parameter, e.g. symptom, associated with the condition being treated. As such, treatment includes situations where the condition, or at least symptoms associated therewith, are reduced or avoided. Thus treatment includes: (i) prevention, that is, reducing the risk of development of clinical symptoms, including causing the clinical symptoms not to develop, e.g., preventing disease progression to a harmful or otherwise undesired state; (ii) inhibition, that is, arresting the development or further development of clinical symptoms, e.g., mitigating or completely inhibiting an active disease.

"Potency" refers to the degree of protection from challenge with BoNT. This can be measured/quantified for example, as an increase in the $LD_{50}$ of a Botulinum neurotoxin (BoNT). In toxicology, the median lethal dose, $LD_{50}$ (abbreviation for "Lethal Dose, 50%"), or $LCt_{50}$ (Lethal Concentration & Time) of a toxic substance or radiation is the dose required to kill half the members of a tested population. The $LD_{50}$ usually expressed as the mass of substance administered per unit mass of test subject, such as grams of substance per kilogram of body mass. Stating it this way allows the relative toxicity of different substances to be compared, and normalizes for the variation in the size of the animals exposed (although toxicity does not always scale simply with body mass). Typically, the $LD_{50}$ of a substance is given in milligrams per kilogram of body weight. In the case of some toxins, the $LD_{50}$ may be more conveniently expressed as micrograms per kilogram (µg/kg) of body mass.

The term "high affinity" when used with respect to an antibody refers to an antibody that specifically binds to its target(s) with an affinity ($K_D$) of at least about 5 nM or less.

The following abbreviations are used herein: BoNT; Botulinum neurotoxin, BoNT/A; BoNT serotype A, BoNT/B; BoNT serotype B, BoNT/C; BoNT serotype C, BoNT/D; BoNT serotype D, BoNT/F; BoNT serotype F, BoNT/G; BoNT serotype G, Fc; fragment crystalizable, Fab'$_2$; fragment, antigen binding, mAb; monoclonal antibody, IgG; immunoglobulin G, LD$_{50}$; lethal dose 50%, scFv; single chain variable fragment, V$_H$; heavy chain variable region, V$_k$; kappa light chain variable region, PCR; polymerase chain reaction, Agall or Aga2; yeast agglutinin receptor II, BoNT/A L$_C$; BoNT/A light chain, BoNT/B L$_C$; BoNT/B light chain, BoNT/B H$_C$; C-terminal domain of the BoNT/B heavy chain, pM; picomolar, fM; femtomolar, IU; International Unit, SD-CAA; selective dextrose casamino acids media, SG-CAA; selective galactose casamino acids media, CHO; Chinese hamster ovary cells, FACS; fluorescent activated cell sorting, K$_D$; equilibrium dissociation constant, k$_{on}$; association rate constant, k$_{off}$; dissociation rate constant, MFI: mean fluorescent intensity.

The terms "polypeptide", "peptide", and "protein" are used interchangeably herein to designate a linear series of amino acid residues connected one to the other by peptide bonds between the alpha-amino and carboxy groups of adjacent residues. The amino acid residues are usually in the natural "L" isomeric form. However, residues in the "D" isomeric form can be substituted for any L-amino acid residue, as long as the desired functional property is retained by the polypeptide. In addition, the amino acids, in addition to the 20 "standard" amino acids, include modified and unusual amino acids, which include, but are not limited to those listed in 37 CFR (§ 1.822(b)(4)). Furthermore, it should be noted that a dash at the beginning or end of an amino acid residue sequence indicates either a peptide bond to a further sequence of one or more amino acid residues or a covalent bond to a carboxyl or hydroxyl end group. However, the absence of a dash should not be taken to mean that such peptide bonds or covalent bond to a carboxyl or hydroxyl end group is not present, as it is conventional in representation of amino acid sequences to omit such.

The term "antibody" (also used interchangeably with "immunoglobulin") encompasses polyclonal and monoclonal antibody preparations where the antibody may be of any class of interest (e.g., IgM, IgG, and subclasses thereof), as well as preparations including hybrid antibodies, altered antibodies, F(ab')$_2$ fragments, F(ab) molecules, Fv fragments, scFv fragments, single chain antibodies, single domain antibodies, chimeric antibodies, humanized antibodies, and functional fragments thereof which exhibit immunological binding properties of the parent antibody molecule. The antibodies may be conjugated to other moieties, and/or may be bound to a support (e.g., a solid support), such as a polystyrene plate or bead, test strip, and the like.

Immunoglobulin polypeptides include the kappa and lambda light chains and the alpha, gamma (IgG$_1$, IgG$_2$, IgG$_3$, IgG$_4$), delta, epsilon and mu heavy chains or equivalents in other species. Full-length immunoglobulin "light chains" (usually of about 25 kDa or about 214 amino acids) comprise a variable region of about 110 amino acids at the NH$_2$-terminus and a kappa or lambda constant region at the COOH-terminus. Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids).

An immunoglobulin light or heavy chain variable region is composed of a "framework" region (FR) interrupted by three hypervariable regions, also called "complementarity determining regions" or "CDRs". The extent of the framework region and CDRs have been defined (see, "Sequences of Proteins of Immunological Interest," E. Kabat et al., U.S. Department of Health and Human Services, (1991) and Lefranc et al. IMGT, the international ImMunoGeneTics information system®. Nucl. Acids Res., (2005) 33:D593-D597)). A detailed discussion of the IMGTS system, including how the IMGTS system was formulated and how it compares to other systems, is provided on the World Wide Web at imgt.cines.fr/textes/IMGTScientificChart/Numbering/IMGTnumberingsTable.html. The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen. All CDRs and framework provided by the present disclosure are defined according to Kabat et al, supra, unless otherwise indicated. The three light chain CDRs, as used herein, are also referred to as "CDR-L1", "CDR-L2", and "CDR-L3". The three heavy chain variable CDRs, as used herein, are also referred to as "CDR-H1", "CDR-H2", and "CDR-H3".

An "antibody" thus encompasses a protein having one or more polypeptides that can be genetically encodable, e.g., by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (V$_L$) and variable heavy chain (V$_H$) refer to these light and heavy chains respectively.

Antibodies encompass intact immunoglobulins as well as a number of well characterized fragments produced by digestion with various peptidases. Thus, for example, pepsin digests an antibody below the disulfide linkages in the hinge region to produce F(ab)'$_2$, a dimer of Fab which itself is a light chain joined to VH-CHI by a disulfide bond. The F(ab)'$_2$ may be reduced under mild conditions to break the disulfide linkage in the hinge region thereby converting the (Fab')$_2$ dimer into an Fab' monomer. The Fab' monomer is essentially an Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies, including, but are not limited to, Fab'$_2$, IgG, IgM, IgA, scFv, dAb, nanobodies, unibodies, and diabodies.

Antibodies and fragments of the present disclosure encompass those that are bispecific. Bispecific antibodies or fragments can be of several configurations. For example, bispecific antibodies may resemble single antibodies (or antibody fragments) but have two different antigen binding sites (variable regions). Bispecific antibodies may be produced by chemical techniques (Kranz et al. (1981) *Proc. Natl. Acad. Sci.*, USA, 78: 5807), by "polydoma" techniques (see, e.g., U.S. Pat. No. 4,474,893), or by recombinant DNA techniques. Bispecific antibodies may have binding specificities for at least two different epitopes, at least one of which is an epitope of BoNT. The BoNT binding antibodies and fragments can also be heteroantibodies. Heteroantibodies are two or more antibodies, or antibody binding fragments (e.g., Fab) linked together, each antibody or fragment having a different specificity.

An "antigen-binding site" or "binding portion" refers to the part of an immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" or "FRs". Thus, the term "FR" refers to amino acid sequences that are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and light chains are referred to as "complementarity determining regions" or "CDRs" and are characterized, for example by Kabat et al. *Sequences of proteins of immunological interest*, 4th ed. U.S. Dept. Health and Human Services, Public Health Services, Bethesda, Md. (1987).

A 4C10.20 antibody refers to an antibody expressed by clone 4C10.20 or to an antibody synthesized in other manners, but having the same CDRs and optionally, the same framework regions as the antibody expressed by clone 4C10.20. Similarly, antibody 4C10.5 and any other shown in FIG. 1 or FIG. 2 and the like refer to antibodies expressed by the corresponding clone(s) and/or to antibodies synthesized in other manners, but having the same CDRs and optionally, the same framework regions as the referenced antibodies.

As used herein, the terms "immunological binding" and "immunological binding properties" refer to the non-covalent interactions of the type which occur between an immunoglobulin molecule and an antigen for which the immunoglobulin is specific. The strength or affinity of immunological binding interactions can be expressed in terms of the dissociation constant ($K_D$) of the interaction, wherein a smaller $K_D$ represents a greater affinity Immunological binding properties of selected polypeptides can be quantified using methods well known in the art. One such method entails measuring the rates of antigen binding site/antigen complex formation and dissociation, wherein those rates depend on the concentrations of the complex partners, the affinity of the interaction, and on geometric parameters that equally influence the rate in both directions. Thus, both the "on rate constant" ($k_{on}$) and the "off rate constant" ($k_{off}$) can be determined by calculation of the concentrations and the actual rates of association and dissociation. The ratio of $k_{off}/k_{on}$ enables cancellation of all parameters not related to affinity and is thus equal to the equilibrium dissociation constant $K_D$ (see, generally, Davies el al. *Ann. Rev. Biochem.* 1990, 59: 439-15 473).

An "anti-BoNT antibody" refers to an antibody that binds to one or more Botulinum neurotoxin(s) (e.g., BoNT/C, BoNT/CD, etc.). Thus, for example the term "anti-BoNT/C-antibody", as used herein refers to an antibody that specifically binds to a BoNT/C polypeptide (e.g., a BoNT/C polypeptide). An example of an antibody of the present disclosure may bind to an LC domain of a BoNT/C polypeptide.

Antibodies derived from anti-BoNT antibodies have a binding affinity of about $1.6 \times 10^{-8}$ or better and can be derived by screening libraries of single chain Fv fragments displayed on phage or yeast constructed from heavy ($V_H$) and light ($V_L$) chain variable region genes obtained from mammals, including mice and humans, immunized with botulinum toxoid, toxin, or BoNT fragments. Antibodies can also be derived by screening phage or yeast display libraries in which a known BoNT-neutralizing variable heavy ($V_H$) chain is expressed in combination with a multiplicity of variable light ($V_L$) chains or conversely a known BoNT-neutralizing variable light chain is expressed in combination with a multiplicity of variable heavy ($V_H$) chains. BoNT-neutralizing antibodies also include those antibodies produced by the introduction of mutations into the variable heavy or variable light complementarity determining regions (CDR1, CDR2 or CDR3) as described herein. Finally BoNT-neutralizing antibodies include those antibodies produced by any combination of these modification methods as applied to the BoNT-neutralizing antibodies described herein and their derivatives.

An "epitope" is a site on an antigen (e.g. BoNT) to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

A neutralizing epitope refers to the epitope specifically bound by a neutralizing antibody.

"Isolated" refers to an entity of interest that is in an environment different from that in which the compound may naturally occur. An "isolated" compound (e.g., an "isolated" antibody) is separated from all or some of the components that accompany it in nature and may be substantially enriched, e.g., may be purified so that the compound is at least about 70% pure, at least about 80% pure, at least about 90% pure, at least about 95% pure, at least about 98% pure, at least about 99%, or greater than 99% pure, or free of impurities, contaminants, and/or components other than the compound. "Isolated" also refers to the state of a compound separated from all or some of the components that accompany it during manufacture (e.g., chemical synthesis, recombinant expression, culture medium, and the like).

A single chain Fv ("scFv") polypeptide is a covalently linked $V_H::V_L$ heterodimer which may be expressed from a nucleic acid including $V_H$- and $V_L$-encoding sequences either joined directly or joined by a peptide-encoding linker (Huston, et al. (1988) *Proc. Nat. Acad. Sci.* USA, 85: 5879-5883). A number of structures are available for converting the light and heavy polypeptide chains from an antibody V region into an scFv molecule which will fold into a three dimensional structure substantially similar to the structure of an antigen-binding site. See, e.g. U.S. Pat. Nos. 5,091,513 and 5,132,405 and 4,956,778.

Recombinant design methods may be used to develop suitable chemical structures (linkers) for converting two heavy and light polypeptide chains from an antibody variable region into a scFv molecule which will fold into a three-dimensional structure that is substantially similar to native antibody structure.

Design criteria include determination of the appropriate length to span the distance between the C-terminal of one chain and the N-terminal of the other, wherein the linker is generally formed from small hydrophilic amino acid residues that do not tend to coil or form secondary structures. Such methods have been described in the art. See, e.g., U.S. Pat. Nos. 5,091,513 and 5,132,405 to Huston et al.; and U.S. Pat. No. 4,946,778 to Ladner et al.

In this regard, the first general step of linker design involves identification of plausible sites to be linked. Appropriate linkage sites on each of the $V_H$ and $V_L$ polypeptide domains include those which will result in the minimum loss of residues from the polypeptide domains, and which will necessitate a linker comprising a minimum number of residues consistent with the need for molecule stability. A pair of sites defines a "gap" to be linked. Linkers connecting the C-terminus of one domain to the N-terminus of the next generally comprise hydrophilic amino acids which assume an unstructured configuration in physiological solutions and may be free of residues having large side groups which might interfere with proper folding of the $V_H$ and $V_L$ chains. Thus, suitable linkers generally comprise polypeptide chains of alternating sets of glycine and serine residues, and may include glutamic acid and lysine residues inserted to enhance solubility. One particular linker has the amino acid sequence $(Gly_4Ser)_3$ (SEQ ID NO: 42). Another example of a suitable linker is a linker that has the amino acid sequence comprising 2 or 3 repeats of $[(Ser)_4Gly]$ (SEQ ID NO: 43), such as $[(Ser)_4Gly]_3$ (SEQ ID NO: 44), and the like. Nucleotide sequences encoding such linker moieties can be readily provided using various oligonucleotide synthesis techniques known in the art (see, e.g., Sambrook, supra.).

The phrase "specifically binds to" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to a protein under such conditions may require an antibody that is selected for its specificity for a particular protein. For example, BoNT/C-neutralizing antibodies can be raised to BoNT/C protein(s) that specifically bind to BoNT/C protein(s), and not to other proteins present in a tissue sample. A variety of immunoassay formats may be used to select antibodies specifically immunoreactive with a particular protein. For example, solid-phase enzyme-linked immunosorbent assay (ELISA) immunoassays are routinely used to select monoclonal antibodies specifically immunoreactive with a protein. See Harlow and Lane (1988) Antibodies, A Laboratory Manual, Cold Spring Harbor Publications, New York, for a description of immunoassay formats and conditions that can be used to determine specific immunoreactivity.

The term "conservative substitution" is used in reference to proteins or peptides to reflect amino acid substitutions that do not substantially alter the activity (specificity or binding affinity) of the molecule. Typically conservative amino acid substitutions involve substituting one amino acid for another amino acid with similar chemical properties (e.g. charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

DETAILED DESCRIPTION

The present disclosure provides antibodies that specifically bind to botulinum neurotoxins. The antibodies and derivatives thereof that specifically bind to the neutralizing epitopes provided herein can be used in methods to specifically bind and, in some embodiments, neutralize, botulinum neurotoxin and are therefore also useful in the treatment.

Botulinum neurotoxin is produced by the anaerobic bacterium *Clostridium botulinum*. Botulinum neurotoxin poisoning (botulism) arises in a number of contexts including, but not limited to food poisoning (food borne botulism), infected wounds (wound botulism), "infant botulism" from ingestion of spores and production of toxin in the intestine of infants, and as a chemical/biological warfare agent. Botulism is a paralytic disease that typically begins with cranial nerve involvement and progresses caudally to involve the extremities. In acute cases, botulism can prove fatal.

For each BoNT serotype, there can be multiple subtypes of BoNT. Antibodies of the present disclosure encompass antibodies that specifically bind one serotype (e.g. the BoNT/C serotype) and also antibodies that can bind more than one subtype/serotype.

The present disclosure is related to the discovery of high affinity antibodies. The antibodies are particularly efficient in the neutralization of a botulism neurotoxin (BoNT) subtype. The antibodies have a high affinity for BoNT and each of the various antibodies is either highly specific for a serotype/subtype or can cross-react with two, three, or more serotypes/subtypes (e.g. BoNT/C, BoNT/D, BoNT/CD and/or BoNT/DC). Neutralizations of BoNT may also be accomplished by using one, two, three, four, or more different antibodies directed against each of the subtypes, or alternatively, by the use of antibodies that are cross-reactive for different BoNT subtypes (e.g. BoNT/C, BoNT/D, BoNT/CD and/or BoNT/DC), or by bispecific or polyspecific antibodies with specificities for two, three, or four or more BoNT epitopes, and/or serotypes, and/or subtypes.

Compositions containing at least two, or at least three high affinity antibodies that bind overlapping (partial or complete overlapping) or non-overlapping epitopes on the BoNT are contemplated herein.

Thus, compositions contemplated herein may include one, two or more, three or more, four or more, five or more different antibodies selected from the antibodies described herein (see, e.g., FIG. 1 and FIG. 2) and/or antibodies comprising one or more CDRs from these antibodies, and/or one or more antibodies comprising mutants or derivatives of these antibodies.

Compositions contemplated herein may include antitoxins that specifically bind one or more of BoNT/C, BoNT/D, and/or (or mosaics thereof). Compositions containing trivalent BoNT/C and/or BoNT/D antibodies (e.g. comprising antibodies selected from those described in PCT Pub. Nos.

WO 07/094754, WO 05/016232, WO 09/008916, and WO 2010/014854) are also contemplated.

As indicated above, the antibodies provided by the present disclosure bind to one or more botulinum neurotoxin serotypes C or D (or mosaics thereof) and in certain instances BoNT serotypes, and, in some embodiments, can specifically bind to, and in some embodiments, neutralize the neurotoxin. Neutralization, in this context, refers to a measurable decrease in the toxicity and/or circulating level of the target neurotoxin. Such a decrease in toxicity can also be measured in vitro by a number of methods well known to those of skill in the art. One such assay involves measuring the time to a given percentage (e.g., 50%) twitch tension reduction in a hemidiaphragm preparation. Toxicity reduction can be determined in vivo, e.g. as an $LD_{50}$ in a test animal (e.g. mouse) BoNT in the presence of one or more putative neutralizing antibodies. The neutralizing antibody or antibody combination can be combined with the botulinum neurotoxin prior to administration, or the animal can be administered the antibody prior to, simultaneous with, or after administration of the neurotoxin. The rate of clearance of BoNT mediated by a test antibody, or combination of test antibodies, can be measured (e.g. in mice) by administering labeled BoNT (e.g. radiolabeled BoNT) and measuring the levels of BoNT in the serum and the liver and other organs over time in the presence or absence of test antibody or antibodies (see, e.g., Ravichandran et al. (2006) *J Pharmacol Exp Ther* 318: 1343-1351 (2006).

The present disclosure also contemplates an antibody that specifically binds an epitope shared by two or more (e.g., two, three, four, five, six, or seven) BoNT serotypes and/or subtypes and/or mosaics, e.g., BoNT polypeptides that share at least about 45%, at least about 50%, at least about 60%, at least about 70%, at least about 80%, at least about 90%, at least about 95%, at least about 98%, or at least about 99%, amino acid sequence identity over the complete holotoxin, over the light chain only, over the translocation domain only, or over the C-terminal third of the protein that includes the receptor-binding domain.

As the antibodies of the present disclosure act to specifically bind to, and in some embodiments, neutralize botulinum neurotoxins, they are useful in the treatment of pathologies associated with botulinum neurotoxin poisoning. The treatments essentially comprise administering to the poisoned organism (e.g. human or non-human mammal) a quantity of one or more neutralizing antibodies sufficient to neutralize (e.g. mitigate or eliminate) symptoms of BoNT poisoning.

Such treatments are most desired and efficacious in acute cases (e.g. where vital capacity is less than 30-40 percent of predicted and/or paralysis is progressing rapidly and/or hypoxemia with absolute or relative hypercarbia is present. These antibodies can also be used to treat early cases with symptoms milder than indicated (to prevent progression) or even prophylactically (a use the military envisions for soldiers going in harm's way). Treatment with the neutralizing antibody can be provided as an adjunct to other therapies (e.g. antibiotic treatment).

The antibodies provided by this disclosure can also be used for the rapid detection/diagnosis of botulism and thereby supplement and/or replace previous laboratory diagnostics.

This disclosure also provides the epitopes specifically bound by botulinum neurotoxin antibodies described herein Such epitopes are found at or near the N-terminus of the alpha helix-1 on the LC domain. These epitopes can be used to isolate, and/or identify and/or screen for other antibodies BoNT neutralizing antibodies as described herein.

I. Botulinum Neurotoxin (BoNT)—Binding Antibodies

Anti-BoNT antibodies may be selected based on their affinity to one or more BoNT serotypes/subtypes. Numbering system used herein for toxins is based on Lacy et al. (1999) *J. Mol. Biol.* 291:1091-1104. A number of subtypes are known for each BoNT serotype. Thus, for example, BoNT/A subtypes include, but are not limited to, BoNT/A1, BoNT/A2, BoNT/A3, and the like. It is also noted, for example, that the BoNT/A1 subtype includes, but is not limited to 62A, NCTC 2916, ATCC 3502, and Hall hyper (Hall Allergan) and are identical (99.9-100% identity at the amino acid level.) and have been classified as subtype A1. The BoNT/A2 sequences (Kyoto-F and FRI-A2H) (Willems, et al. (1993) Res. *Microbiol.* 144:547-556) are 100% identical at the amino acid level. Another BoNT/A subtype, e.g. A3, is produced by a strain called Loch Maree that killed a number of people in an outbreak in Scotland.

Similarly, a number of mosaics are also known for BoNT/C and BoNT/D. The subject antibodies encompass high affinity antibodies that are cross-reactive with two or more mosaics or subtypes within a serotype (e.g. BoNT/C, BoNT/D, BoNT/CD and/or BoNT/DC). The epitope for antibody 4C10, and its derivatives (e.g. 4C10.5, 4C10.8, 4C10.15, 4C10.17, 4C10.18, 4C10.20, and/or 4C10.22), comprises several amino acids found at or near the N-terminus of the first alpha-helix of the LC domain. The epitope for antibody 4C10, and its derivatives (e.g. 4C10.5, 4C10.8, 4C10.15, 4C10.17, 4C10.18, 4C10.20, and/or 4C10.22) comprises about 1 amino acid to about 25 amino acids, e.g., an epitope comprising 1 amino acid (aa) to 10 aa, 10 aa to 15 aa, 15 aa to 20 aa, or 20 aa to 25 aa. For example, an epitope for antibody 4C10, and its derivatives (e.g. 4C10.5, 4C10.8, 4C10.15, 4C10.17, 4C10.18, 4C10.20, and/or 4C10.22) comprises 1 aa, 2 aa, 3aa, 4 aa, 5 aa, 6 aa, 7, aa, 8 aa, 9 aa, 10 aa, 11 aa, 12 aa, 13 aa, 14 aa, 15 aa, 16 aa, 17 aa, 18 aa, 19 aa, 20 aa, 21 aa, 22 aa, 23 aa, 24 aa, or 25 aa. In some cases, the epitope for antibody 4C10, and its derivatives (e.g. 4C10.5, 4C10.8, 4C10.15, 4C10.17, 4C10.18, 4C10.20, and/or 4C10.22) comprises 5 amino acids to 10 amino acids, e.g., 5 aa, 6 aa, 7 aa, 8 aa, 9 aa, or 10 aa.

Serotypes that can be bound by the subject antibodies include BoNT/C, BoNT/D, or mosaics thereof. Other BoNT subtypes/serotypes include pure BoNT/C, BoNT/D, BoNT/CD and/or BoNT/DC. Moreover, without being bound to a particular theory, these cross-reactive antibodies can be more efficient in neutralizing Botulinum neurotoxin, particularly when used in combination with one or more different neutralizing antibodies.

The sequences of the variable heavy ($V_H$) and variable light ($V_L$) domains for a number of BoNT (e.g. BoNT/C, BoNT/D) antibodies are illustrated in FIG. 1, and Tables 2, 7, and 8. Some antibodies of interest as seen in FIG. 2 encompass antibodies from clones 4C10.5, 4C10.8, 4C10.15, 4C10.17, 4C10.18, 4C10.20, and/or 4C10.22. Antibodies of interest, as depicted in FIG. 2, include antibodies from clones 4C10.5, 4C10.8, 4C10.15, 4C10.17, 4C10.18, 4C10.20, and/or 4C10.22.

The relationship of certain antibodies specific for each subtype from each serotype is described in the example section below.

The antibodies of the present disclosure can be used individually, and/or in combination with each other, and/or in combination with other known anti-BoNT antibodies (see, e.g., Application Pub. No: 20080124328, 20020155114, 20040175385, 20020155114, and PCT Pub. Nos. WO 07/094754, WO 05/016232, WO 09/008916, and WO 2010/014854, which are incorporated herein by reference for all purposes). These antibodies can be used individually, and/or in combination with each other, and/or in combination with other known anti-BoNT antibodies to form bispecific or polyspecific antibodies.

Amino acid sequences of various antibodies, as well as each CDR and framework region, are shown in FIG. 1 and FIG. 2. It will be appreciated that the amino acid sequence of a CDR can also be defined using alternative systems, which will be readily apparent to and applied by the ordinarily skilled artisan (see, "Sequences of Proteins of Immunological Interest," E. Kabat et al., U.S. Department of Health and Human Services, (1991); and Lefranc et al. IMGT, the international ImMunoGeneTics information system. Nucl. Acids Res., (2005) 33:D593-D597)). A detailed discussion of the IMGTS system, including how the IMGTS system was formulated and how it compares to other systems, is provided on the World Wide Web at imgt.cines.fr/textes/ IMGTScientificChart/ Numbering/IMGTnumberingsTable.html. As seen in FIG. 1, CDRs are demarcated for each antibody in their respective columns and labels. All amino acid sequences of CDR in the present disclosure are defined according to Kabat et al., supra, unless otherwise indicated.

Using the teachings and the sequence information provided herein, the variable light and variable heavy chains can be joined directly or through a linker (e.g., $(Gly_4Ser)_3$, SEQ ID NO: 42) to form a single-chain Fv antibody. The various CDRs and/or framework regions can be used to form human antibodies, chimeric antibodies, antibody fragments, polyvalent antibodies, and the like.

Anti-BoNT antibodies of the present disclosure have a binding affinity ($K_D$) for a BoNT protein of at least $10^{-7}$ M, at least $10^{-8}$ M, at least $10^{-9}$ M, at least $10^{-10}$ M, at least $10^{-11}$ M, or at least $10^{-12}$ M. Some examples of $K_D$s ($M^{-1}$) for BoNT/C or BoNT/D fall in the following ranges: between about $2 \times 10^{-12}$ to about $5 \times 10^{-10}$, between about $5 \times 10^{-10}$ to about $1 \times 10^{-9}$, between $1 \times 10^{-9}$ to $5 \times 10^{-9}$, between $5 \times 10^{-9}$ to $1 \times 10^{-8}$, between $4 \times 10^{-9}$ to $2 \times 10^{-8}$. Certain antibodies (e.g. 8DC4) have a $K_D$ of more than 20 nM.

In some cases, the antibody has a $K_D$ with a Botulinum neurotoxin of about 5 nM or less. In some cases, the antibody binds to BoNT/C, BoNT/D, or a mosaic thereof with high affinity.

Some examples of $K_D$s ($M^{-1}$) for BoNT/C and BoNT/D fall in the following ranges: between about $5 \times 10^{-11}$ to about $1 \times 10^{-10}$, between about $1 \times 10^{-10}$ to about $5 \times 10^{-10}$, between about $5 \times 10^{-10}$ to about $1 \times 10^{-9}$, between $1 \times 10^{-9}$ to about $5 \times 10^{-9}$, between $5 \times 10^{-8}$ to about $1 \times 10^{-8}$ between $1 \times 10^{-8}$ to about $5 \times 10^{-8}$. Certain antibodies can have a $K_D$ for BoNT/C, BoNT/D, and/or BoNT/DC in the range between about $1 \times 10^{-8}$ to about $4 \times 10^{-8}$.

As noted above, the antibody may also be defined by the serotypes and/or subtypes with which it is cross-reactive. Some antibodies have an affinity that is specific for only one serotype or subtype. Others are cross-reactive for two or more subtypes and/or serotypes, for example BoNT/C, BoNT/D, BoNT/CD, and/or BoNT/DC. Examples of cross-reactive antibodies include 4C10, 4C10.1, 4C10.2, 4C10.5, 4C10.8, 4C10.15, 4C10.17, 4C10.18, 4C10.20, and 4C10.22. Antibodies can also be reactive across two or more serotypes (e.g. BoNT/C, BoNT/D, BoNT/CD and/or BoNT/DC).

The epitope for antibody 4C10, and its derivatives (e.g. 4C10.5, 4C10.8, 4C10.15, 4C10.17, 4C10.18, 4C10.20, and/or 4C10.22), comprises several amino acids found at or near the N-terminus of the first alpha-helix of the LC domain. The epitope for antibody 4C10, and its derivatives (e.g. 4C10.5, 4C10.8, 4C10.15, 4C10.17, 4C10.18, 4C10.20, and/or 4C10.22) comprises about 1 amino acid to about 25 amino acids, e.g., an epitope comprising 1 amino acid (aa) to 10 aa, 10 aa to 15 aa, 15 aa to 20 aa, or 20 aa to 25 aa. For example, an epitope for antibody 4C10, and its derivatives (e.g. 4C10.5, 4C10.8, 4C10.15, 4C10.17, 4C10.18, 4C10.20, and/or 4C10.22) comprises 1 aa, 2 aa, 3aa, 4 aa, 5 aa, 6 aa, 7, aa, 8 aa, 9 aa, 10 aa, 11 aa, 12 aa, 13 aa, 14 aa, 15 aa, 16 aa, 17 aa, 18 aa, 19 aa, 20 aa, 21 aa, 22 aa, 23 aa, 24 aa, or 25 aa. In some cases, the epitope for antibody 4C10, and its derivatives (e.g. 4C10.5, 4C10.8, 4C10.15, 4C10.17, 4C10.18, 4C10.20, and/or 4C10.22) comprises 5 amino acids to 10 amino acids, e.g., 5 aa, 6 aa, 7 aa, 8 aa, 9 aa, or 10 aa.

The antibody of the present disclosure may be defined by the epitope or the domain of BoNT bound by the antibody. The antibodies provided here may encompass those that bind to one or more epitopes or a specific domain of a BoNT to which an antibody containing one or more of the CDRs set forth in FIG. 1 bind. Epitopes bound by an antibody may be described by a specific BoNT domain and/or the residues therein that contribute to the interaction between the antibody and a BoNT protein. Domains bound by the certain antibodies are identified in the Table 8-9 and in the example section.

In some cases, the antibody specifically binds an epitope of a Botulinum neurotoxin that is specifically bound by an antibody comprising a $V_H$ comprising a CDR1, CDR2 and CDR3, wherein the CDR1, CDR2 and CDR3 are selected from a $V_H$ of an antibody selected from the group consisting of 4C10.5, 4C10.8, 4C10.15, 4C10.17, 4C10.18, 4C10.20, and/or 4C10.22; and a $V_L$ comprising a CDR1, CDR2 and CDR3, wherein the CDR1, CDR2 and CDR3 are are selected from a $V_L$ of an antibody selected from the group consisting 4C10.5, 4C10.8, 4C10.15, 4C10.17, 4C10.18, 4C10.20, and/or 4C10.22. In some cases, the antibody is 4C10.20.

In some cases, the antibody specifically binds an epitope of a Botulinum neurotoxin that is specifically bound by an antibody comprising a $V_H$ comprising a CDR1, CDR2 and CDR3, wherein the CDR1, CDR2 and CDR3 are present in a $V_H$ of an antibody selected from the group consisting of 4C10.5, 4C10.8, 4C10.15, 4C10.17, 4C10.18, 4C10.20, and/or 4C10.22; and a $V_L$ comprising a CDR1, CDR2 and CDR3, wherein the CDR1, CDR2 and CDR3 are are present in a $V_L$ of an antibody selected from the group consisting 4C10.5, 4C10.8, 4C10.15, 4C10.17, 4C10.18, 4C10.20, and/or 4C10.22. In some cases, the antibody is 4C10.20.

For example, based on Table 8, an antibody such as 4C10, may be described by its affinity to the LC domain and its cross reactivity with BoNT/C, BoNT/CD, BoNT/D, and BoNT/DC. In some cases, the antibody cross reacts with and specifically binds to, and in some embodiments, neutralizes a Botulinum neurotoxin BoNT/CD mosaic and a Botulinum neurotoxin BoNT/DC mosaic.

The 4C10 antibody and its derivatives (e.g. 4C10.5, 4C10.8, 4C10.15, 4C10.17, 4C10.18, 4C10.20, and/or 4C10.22) bind to an epitope that is part of the LC domain epitope cluster. Therefore, the 4C10 epitope overlaps with several other LC binding antibodies. Any of a number of competitive binding assays can be used to measure competition between two antibodies to the same antigen. For example, a sandwich ELISA assay can be used for this purpose. Additional methods for epitope mapping are described later below.

A first antibody is considered to competitively inhibit binding of a second antibody, if binding of the second antibody to the antigen is reduced by at least 30%, usually at least about 40%, 50%, 60% or 75%, and often by at least about 90%, in the presence of the first antibody using any of the assays used to assess competitive binding.

Accordingly, antibodies provided by the present disclosure encompass those that compete for binding to a BoNT with an antibody that includes one or more of the $V_H$ CDRs (e.g. one or more of CDR-H1, CDR-H2, and CDR-H3) set forth in FIG. 1 or FIG. 2 and/or one or more of the $V_L$ CDRs (e.g. one or more of CDR-L1, CDR-L2, and CDR-L3) set forth in FIG. 1 or FIG. 2.

In some cases, the antibody cross-reacts with and specifically binds to Botulinum neurotoxin serotype BoNT/C, Botulinum neurotoxin serotype BoNT/D, Botulinum neurotoxin serotype BoNT/C, Botulinum neurotoxin serotype BoNT/CD, and Botulinum neurotoxin serotype BoNT/DC, wherein the antibody specifically binds an epitope of a Botulinum neurotoxin that is specifically bound by an antibody comprising a $V_H$ comprising a CDR1, CDR2 and CDR3, wherein the CDR1, CDR2 and CDR3 are selected from a $V_H$ of an antibody selected from the group consisting of 4C10.5, 4C10.8, 4C10.15, 4C10.17, 4C10.18, 4C10.20, and 4C10.22; and a $V_L$ comprising a CDR1, CDR2 and CDR3, wherein the CDR1, CDR2 and CDR3 are selected from a $V_L$ of an antibody selected from the group consisting 4C10.5, 4C10.8, 4C10.15, 4C10.17, 4C10.18, 4C10.20, and 4C10.22.

In some cases, the antibody cross-reacts with and specifically binds to Botulinum neurotoxin serotype BoNT/C, Botulinum neurotoxin serotype BoNT/D, Botulinum neurotoxin serotype BoNT/C, Botulinum neurotoxin serotype BoNT/CD, and Botulinum neurotoxin serotype BoNT/DC, wherein the antibody specifically binds an epitope of a Botulinum neurotoxin that is specifically bound by an antibody comprising a $V_H$ comprising a CDR1, CDR2 and CDR3, wherein the CDR1, CDR2 and CDR3 are present in a $V_H$ of an antibody selected from the group consisting of 4C10.5, 4C10.8, 4C10.15, 4C10.17, 4C10.18, 4C10.20, and 4C10.22; and a $V_L$ comprising a CDR1, CDR2 and CDR3, wherein the CDR1, CDR2 and CDR3 are present in a $V_L$ of an antibody selected from the group consisting 4C10.5, 4C10.8, 4C10.15, 4C10.17, 4C10.18, 4C10.20, and 4C10.22.

In some cases, the antibody competes for binding to a Botulinum neurotoxin with an antibody comprising a $V_L$ CDR1 comprising an amino acid sequence of $V_L$ CDR1 of 4C10.20; a $V_L$ CDR2 comprising an amino acid sequence of $V_L$ CDR2 of 4C10.20; and a $V_L$ CDR3 comprising an amino acid sequence of $V_L$ CDR3 of 4C10.20.

In some cases, the antibody competes for binding to a Botulinum neurotoxin with an antibody comprising a $V_H$ CDR1 comprising an amino acid sequence of $V_H$ CDR1 of 4C10.20; a $V_H$ CDR2 comprising an amino acid sequence of $V_H$ CDR2 of 4C10.20; a $V_H$ CDR3 comprising an amino acid sequence of $V_H$ CDR3 of 4C10.20; a $V_L$ CDR1 comprising an amino acid sequence of $V_L$ CDR1 of 4C10.20; a $V_L$ CDR2 comprising an amino acid sequence of $V_L$ CDR2 of 4C10.20; and a $V_L$ CDR3 comprising an amino acid sequence of $V_L$ CDR3 of 4C10.20.

The present disclosure provides an antibody that competes for binding to a Botulinum neurotoxin with an antibody, wherein the antibody is selected from the group consisting of: a) an antibody comprising a heavy chain variable region comprising amino acid sequence:
QVQLVQSGGGVVQPGRSLRLSCGAS-RFTFSGFDMHWVRQAPGKGLEWVARISHDGS-MADYAD SLRGRFTISRDNSKNTLYLQMNSLRVED-TALYYCAKDRWRSGSYPAFEIWGQGTMVTVSS (SEQ ID NO: 23) and a light chain variable region comprising amino acid sequence:
EIVLTQSPSFLSAFVGDRITITCRASQGISNR-LAWYQQKPGKAPNLLIHPASTLQSGVPSRFSGSGS GTDFTLTISSLQPEDFA-TYYCQQANSFPLTFGGGTKVEIKR (SEQ ID NO: 24);
b) an antibody comprising a heavy chain variable region comprising amino acid sequence:
QVQLVQSGGGVVQPGRSLRLSCGAS-RFTFSGFDMHWVRQAPGKGLEWVARISHDGS-MADYAD SLRGRFTISRDNSKNTLYLQMNSLRVED-TALYYCAKDPWRSGSYPAFEIWGQGTMVTVSS (SEQ ID NO: 26) and a light chain variable region comprising amino acid sequence:
EIVLTQSPSFLSAFIGDRITITCRAS QGISNR-LAWYQQKPGKAPNLLIYPASTLQSGVPSRFSGSGSG TDFTLTISSLQPEDFA-TYYCQQANSFPLTFGGGTKVEIKR (SEQ ID NO: 27);
c) an antibody comprising a heavy chain variable region comprising amino acid sequence:
QVQLVQSGGGVVQPGRSLRLSCGAS-RFTFSGFDMHWVRQAPGKGLEWVARISHDGS-MADYAD SLRGRFTISRDNSKNTLYLQMNSLRVED-TALYYCAKDRWRSGSYPAFEIWGQGTMVTVSS (SEQ ID NO: 23) and a light chain variable region comprising amino acid sequence:
EIVLTQSPSFLSAFVGDRITITCRASKGIGNR-LAWYQQKPGKAPNLLIHPASTLQSGVPSRFSGSGS GTDFTLTISSLQPEDFA-TYYCQQANSFPLTFGGGTKVEIKR (SEQ ID NO: 29);
d) an antibody comprising a heavy chain variable region comprising amino acid sequence:
QVQLVQSGGGVVQPGRSLRLSCGAS-RFTFSGFDMHWVRQAPGKGLEWVARISHDGS-MADYAD SLRGRFTISRDNSKNTLYLQMNSLRVED-TALYYCAKDRWRSGSYPAFEIWGQGTMVTVSS (SEQ ID NO: 23) and a light chain variable region comprising amino acid sequence:
EIVLTQSPSFLSAFVGDRITITCRASQGISNR-LAWYQQKPGKAPNLLIHPASSLQSGVPSRFSGSGS GTDFTLTISSLQPEDFA-TYYCQQANSFPLTFGGGTKVEIKR (SEQ ID NO: 31);
e) an antibody comprising a heavy chain variable region comprising amino acid sequence:
QVQLVQSGGGVAQPGRSLRLSCGAS-RFTFSGFDMHWVRQAPGKGLEWVARISHDGS-MADYAD SLRGRFTISRDNSKNTLYLQMNSLRVED-TALYYCAKDRWRSGSYPAFEIWGQGTMVTVSS (SEQ ID NO: 33) and a light chain variable region comprising amino acid sequence:
EIVLTQSPSFLSAFVGDRITITCRASQGIGNR-LAWYQQKPGKAPNLLIHPASTLQSGVPSRFSGSGS GTDFTLTISSLQPEDFATYYCQQAH-RFPLTFGGGTKVEIKR (SEQ ID NO: 34); f) an antibody comprising a heavy chain variable region comprising amino acid sequence:
QVQLVQSGGGVVQPGRSLRLSCGAS-RFTFSGFDMHWVRQAPGKGLEWVARISHDGS-MADYAD SLRGRFTISRDNSKNTLYLQMNSLRVED-TALYYCAKDPWRSGSYPAFEIWGQGTMVTVSS (SEQ ID NO: 26) and a light chain variable region comprising amino acid sequence:
EIVLTQSPSFLSAFIGDRITITCRASQGIGNRLAWYQQKPGKAPNLLIYPASTLQSGVPSRFSGSGSG TDFTLTISSLQPEDFATYYCQQANSFPLTFGGGTKVEIKR (SEQ ID NO: 36); and g) an antibody comprising a heavy chain variable region comprising amino acid sequence:
QVQLVQSGGGVVQPGRSLRLSCGASGFKFSGFDMHWVRQAPGKGLEWVARISHDGSMADYAD SLRGRFTISRDNSKNTLYLQMNSLRVEDTALYYCAKDPWRSGSYPAFEIWGQGTMVTVSS (SEQ ID NO: 38) and a light chain variable region comprising amino acid sequence:

```
                                    (SEQ ID NO: 27)
EIVLTQSPSFLSAFIGDRITITCRASQGISNRLAWYQQKPGKAPNLLIYP

ASTLQSGVPSRFSGSGSGTDFTLTISSLQPEDFATYYCQQANSFPLTFGG

GTKVEIKR.
```

In some cases, the antibody competes for binding to a Botulinum neurotoxin with an antibody comprising an antibody heavy chain variable region comprising amino acid sequence:
QVQLVQSGGGVVQPGRSLRLSCGASRFTFSGFDMHWVRQAPGKGLEWVARISHDGSMADYAD SLRGRFTISRDNSKNTLYLQMNSLRVEDTALYYCAKDPWRSGSYPAFEIWGQGTMVTVSS (SEQ ID NO: 26) and an antibody light chain variable region comprising amino acid sequence:

```
                                    (SEQ ID NO: 36)
EIVLTQSPSFLSAFIGDRITITCRASQGIGNRLAWYQQKPGKAPNLLIYP

ASTLQSGVPSRFSGSGSGTDFTLTISSLQPEDFATYYCQQANSFPLTFGG

GTKVEIKR.
```

In some cases, the antibody competes for binding to a Botulinum neurotoxin with an antibody comprising amino acid sequence:

```
                                    (SEQ ID NO: 37)
QVQLVQSGGGVVQPGRSLRLSCGASRFTFSGFDMHWVRQAPGKGLEWVAR

ISHDGSMADYADSLRGRFTISRDNSKNTLYLQMNSLRVEDTALYYCAKDP

WRSGSYPAFEIWGQGTMVTVSSEIVLTQSPSFLSAFIGDRITITCRASQG

IGNRLAWYQQKPGKAPNLLIYPASTLQSGVPSRFSGSGSGTDFTLTISSL

QPEDFATYYCQQANSFPLTFGGGTKVEIKR.
```

The present disclosure provides an antibody that competes for binding to a Botulinum neurotoxin with an antibody, wherein the antibody is selected from the group consisting of: a) an antibody comprising a heavy chain variable region comprising amino acid sequence:
QVQLVQSGGGVVQPGRSLRLSCGASRFTFSGFDMHWVRQAPGKGLEWVARISHDGSMADYAD SLRGRFTISRDNSKNTLYLQMNSLRVEDTALYYCAKDRWRSGSYPAFEIWGQGTMVTVSS (SEQ ID NO: 23) and a light chain variable region comprising amino acid sequence:
EIVLTQSPSFLSAFVGDRITITCRASQGISNRLAWYQQKPGKAPNLLIHPASTLQSGVPSRFSGSGS GTDFTLTISSLQPEDFATYYCQQANSFPLTFGGGTKVEIKR (SEQ ID NO: 24); b) an antibody comprising a heavy chain variable region comprising amino acid sequence:
QVQLVQSGGGVVQPGRSLRLSCGASRFTFSGFDMHWVRQAPGKGLEWVARISHDGSMADYAD SLRGRFTISRDNSKNTLYLQMNSLRVEDTALYYCAKDPWRSGSYPAFEIWGQGTMVTVSS (SEQ ID NO: 26) and a light chain variable region comprising amino acid sequence:
EIVLTQSPSFLSAFIGDRITITCRAS QGISNRLAWYQQKPGKAPNLLIYPASTLQSGVPSRFSGSGSG TDFTLTISSLQPEDFATYYCQQANSFPLTFGGGTKVEIKR (SEQ ID NO: 27); c) an antibody comprising a heavy chain variable region comprising amino acid sequence:
QVQLVQSGGGVVQPGRSLRLSCGASRFTFSGFDMHWVRQAPGKGLEWVARISHDGSMADYAD SLRGRFTISRDNSKNTLYLQMNSLRVEDTALYYCAKDRWRSGSYPAFEIWGQGTMVTVSS (SEQ ID NO: 23) and a light chain variable region comprising amino acid sequence:
EIVLTQSPSFLSAFVGDRITITCRASKGIGNRLAWYQQKPGKAPNLLIHPASTLQSGVPSRFSGSGS GTDFTLTISSLQPEDFATYYCQQANSFPLTFGGGTKVEIKR (SEQ ID NO: 29); d) an antibody comprising a heavy chain variable region comprising amino acid sequence:
QVQLVQSGGGVVQPGRSLRLSCGASRFTFSGFDMHWVRQAPGKGLEWVARISHDGSMADYAD SLRGRFTISRDNSKNTLYLQMNSLRVEDTALYYCAKDRWRSGSYPAFEIWGQGTMVTVSS (SEQ ID NO: 23) and a light chain variable region comprising amino acid sequence:
EIVLTQSPSFLSAFVGDRITITCRASQGISNRLAWYQQKPGKAPNLLIHPASSLQSGVPSRFSGSGS GTDFTLTISSLQPEDFATYYCQQANSFPLTFGGGTKVEIKR (SEQ ID NO: 31); e) an antibody comprising a heavy chain variable region comprising amino acid sequence:
QVQLVQSGGGVAQPGRSLRLSCGASRFTFSGFDMHWVRQAPGKGLEWVARISHDGSMADYAD SLRGRFTISRDNSKNTLYLQMNSLRVEDTALYYCAKDRWRSGSYPAFEIWGQGTMVTVSS (SEQ ID NO: 33) and a light chain variable region comprising amino acid sequence:
EIVLTQSPSFLSAFVGDRITITCRASQGIGNRLAWYQQKPGKAPNLLIHPASTLQSGVPSRFSGSGS GTDFTLTISSLQPEDFATYYCQQAHRFPLTFGGGTKVEIKR (SEQ ID NO: 34); f) an antibody comprising a heavy chain variable region comprising amino acid sequence:
QVQLVQSGGGVVQPGRSLRLSCGASRFTFSGFDMHWVRQAPGKGLEWVARISHDGSMADYAD SLRGRFTISRDNSKNTLYLQMNSLRVEDTALYYCAKDPWRSGSYPAFEIWGQGTMVTVSS (SEQ ID NO: 26) and a light chain variable region comprising amino acid sequence:
EIVLTQSPSFLSAFIGDRITITCRAS QGIGNRLAWYQQKPGKAPNLLIYPASTLQSGVPSRFSGSGSG TDFTLTISSLQPEDFATYYCQQANSFPLTFGGGTKVEIKR (SEQ ID NO: 36); and g) an antibody comprising a heavy chain variable region comprising amino acid sequence:
QVQLVQSGGGVVQPGRSLRLSCGASGFKFSGFDMHWVRQAPGKGLEWVARISHDGSMADYAD SLRGRFTISRDNSKNT- LYLQMNSLRVEDTALYYCAKDPWRSGSYPAFEIWG
QGTMVTVSS (SEQ ID NO: 38) and a light chain
variable region comprising amino acid sequence:

```
                                     (SEQ ID NO: 27)
EIVLTQSPSFLSAFIGDRITITCRASQGISNRLAWYQQKPGKAPNLLIYP

ASTLQSGVPSRFSGSGSGTDFTLTISSLQPEDFATYYCQQANSFPLTFGG

GTKVEIKR.
```

In some cases, the antibody competes for binding to a Botulinum neurotoxin with an antibody comprising an antibody heavy chain variable region comprising amino acid sequence:
QVQLVQSGGGVVQPGRSLRLSCGAS-
RFTFSGFDMHWVRQAPGKGLEWVARISHDGS-
MADYAD SLRGRFTISRDNSKNTLYLQMNSLRVED-
TALYYCAKDPWRSGSYPAFEIWGQGTMVTVSS
(SEQ ID NO: 26) and an antibody light chain variable region comprising amino acid sequence:

```
                                     (SEQ ID NO: 36)
EIVLTQSPSFLSAFIGDRITITCRASQGIGNRLAWYQQKPGKAPNLLIYP

ASTLQSGVPSRFSGSGSGTDFTLTISSLQPEDFATYYCQQANSFPLTFGG

GTKVEIKR.
```

In some cases, the antibody competes for binding to a Botulinum neurotoxin with an antibody comprising amino acid sequence:

```
                                     (SEQ ID NO: 37)
QVQLVQSGGGVVQPGRSLRLSCGASRFTFSGFDMHWVRQAPGKGLEWVAR

ISHDGSMADYADSLRGRFTISRDNSKNTLYLQMNSLRVEDTALYYCAKDP

WRSGSYPAFEIWGQGTMVTVSSEIVLTQSPSFLSAFIGDRITITCRASQG

IGNRLAWYQQKPGKAPNLLIYPASTLQSGVPSRFSGSGSGTDFTLTISSL

QPEDFATYYCQQANSFPLTFGGGTKVEIKR.
```

The present disclosure provides an antibody that binds to a Botulinum neurotoxin, wherein the antibody is selected from the group consisting of: a) an antibody comprising a heavy chain variable region comprising amino acid sequence:
QVQLVQSGGGVVQPGRSLRLSCGAS-
RFTFSGFDMHWVRQAPGKGLEWVARISHDGS-
MADYAD SLRGRFTISRDNSKNTLYLQMNSLRVED-
TALYYCAKDRWRSGSYPAFEIWGQGTMVTVSS
(SEQ ID NO: 23) and a light chain variable region comprising amino acid sequence:
EIVLTQSPSFLSAFVGDRITITCRASQGISNR-
LAWYQQKPGKAPNLLIHPASTLQSGVPSRFSGSGS
GTDFTLTISSLQPEDFA-
TYYCQQANSFPLTFGGGTKVEIKR (SEQ ID NO: 24);
b) an antibody comprising a heavy chain variable region comprising amino acid sequence:
QVQLVQSGGGVVQPGRSLRLSCGAS-
RFTFSGFDMHWVRQAPGKGLEWVARISHDGS-
MADYAD SLRGRFTISRDNSKNTLYLQMNSLRVED-
TALYYCAKDPWRSGSYPAFEIWGQGTMVTVSS
(SEQ ID NO: 26) and a light chain variable region comprising amino acid sequence:
EIVLTQSPSFLSAFIGDRITITCRAS QGISNR-
LAWYQQKPGKAPNLLIYPASTLQSGVPSRFSGSG
SG
TDFTLTISSLQPEDFA-
TYYCQQANSFPLTFGGGTKVEIKR (SEQ ID NO: 27);
c) an antibody comprising a heavy chain variable region comprising amino acid sequence:
QVQLVQSGGGVVQPGRSLRLSCGAS-
RFTFSGFDMHWVRQAPGKGLEWVARISHDGS-
MADYAD SLRGRFTISRDNSKNTLYLQMNSLRVED-
TALYYCAKDRWRSGSYPAFEIWGQGTMVTVSS
(SEQ ID NO: 23) and a light chain variable region comprising amino acid sequence:
EIVLTQSPSFLSAFVGDRITITCRASKGIGNR-
LAWYQQKPGKAPNLLIHPASTLQSGVPSRFSGSGS
GTDFTLTISSLQPEDFA-
TYYCQQANSFPLTFGGGTKVEIKR (SEQ ID NO: 29);
d) an antibody comprising a heavy chain variable region comprising amino acid sequence:
QVQLVQSGGGVVQPGRSLRLSCGAS-
RFTFSGFDMHWVRQAPGKGLEWVARISHDGS-
MADYAD SLRGRFTISRDNSKNTLYLQMNSLRVED-
TALYYCAKDRWRSGSYPAFEIWGQGTMVTVSS
(SEQ ID NO: 23) and a light chain variable region comprising amino acid sequence:
EIVLTQSPSFLSAFVGDRITITCRASQGISNR-
LAWYQQKPGKAPNLLIHPASSLQSGVPSRFSGSGS
GTDFTLTISSLQPEDFA-
TYYCQQANSFPLTFGGGTKVEIKR (SEQ ID NO: 31);
e) an antibody comprising a heavy chain variable region comprising amino acid sequence:
QVQLVQSGGGVAQPGRSLRLSCGAS-
RFTFSGFDMHWVRQAPGKGLEWVARISHDGS-
MADYAD SLRGRFTISRDNSKNTLYLQMNSLRVED-
TALYYCAKDRWRSGSYPAFEIWGQGTMVTVSS
(SEQ ID NO: 33) and a light chain variable region comprising amino acid sequence:
EIVLTQSPSFLSAFVGDRITITCRASQGIGNR-
LAWYQQKPGKAPNLLIHPASTLQSGVPSRFSGSGS
GTDFTLTISSLQPEDFATYYCQQAH-
RFPLTFGGGTKVEIKR (SEQ ID NO: 34); f) an antibody comprising a heavy chain variable region comprising amino acid sequence:
QVQLVQSGGGVVQPGRSLRLSCGAS-
RFTFSGFDMHWVRQAPGKGLEWVARISHDGS-
MADYAD SLRGRFTISRDNSKNTLYLQMNSLRVED-
TALYYCAKDPWRSGSYPAFEIWGQGTMVTVSS
(SEQ ID NO: 26) and a light chain variable region comprising amino acid sequence:
EIVLTQSPSFLSAFIGDRITITCRAS QGIGNR-
LAWYQQKPGKAPNLLIYPASTLQSGVPSRFSGSGSG
TDFTLTISSLQPEDFA-
TYYCQQANSFPLTFGGGTKVEIKR (SEQ ID NO: 36);
and g) an antibody comprising a heavy chain variable region comprising amino acid sequence:
QVQLVQSGGGVVQPGRSLRLSC-
GASGFKFSGFDMHWVRQAPGKGLEWVA-
RISHDGSMADYAD SLRGRFTISRDNSKNT-
LYLQMNSLRVEDTALYYCAKDPWRSGSYPAFEIW
GQGTMVTVSS (SEQ ID NO: 38) and a light chain variable region comprising amino acid sequence:

```
                                     (SEQ ID NO: 27)
EIVLTQSPSFLSAFIGDRITITCRASQGISNRLAWYQQKPGKAPNLLIYP

ASTLQSGVPSRFSGSGSGTDFTLTISSLQPEDFATYYCQQANSFPLTFGG

GTKVEIKR.
```

In some cases, the antibody that binds to a Botulinum neurotoxin comprises an antibody heavy chain variable region comprising amino acid sequence: QVQLVQSGGGVVQPGRSLRLSCGASRFTFSGFDMHWVRQAPGKGLEWVARISHDGSMADYAD SLRGRFTISRDNSKNTLYLQMNSLRVEDTALYYCAKDPWRSGSYPAFEIWGQGTMVTVSS (SEQ ID NO: 26) and an antibody light chain variable region comprising amino acid sequence:

(SEQ ID NO: 36)
EIVLTQSPSFLSAFIGDRITITCRASQGIGNRLAWYQQKPGKAPNLLIYP

ASTLQSGVPSRFSGSGSGTDFTLTISSLQPEDFATYYCQQANSFPLTFGG

GTKVEIKR.

In some cases, the antibody that binds to a Botulinum neurotoxin comprises amino acid sequence:

(SEQ ID NO: 37)
QVQLVQSGGGVVQPGRSLRLSCGASRFTFSGFDMHWVRQAPGKGLEWVAR

ISHDGSMADYADSLRGRFTISRDNSKNTLYLQMNSLRVEDTALYYCAKDP

WRSGSYPAFEIWGQGTMVTVSSEIVLTQSPSFLSAFIGDRITITCRASQG

IGNRLAWYQQKPGKAPNLLIYPASTLQSGVPSRFSGSGSGTDFTLTISSL

QPEDFATYYCQQANSFPLTFGGGTKVEIKR.

In some cases, the antibody competes for binding to a Botulinum neurotoxin with an antibody selected from the group consisting of: a) an antibody comprising a CDR-H1 having amino acid sequence SEQ ID NO: 4, a CDR-H2 having amino acid sequence SEQ ID NO: 6, a CDR-H3 having amino acid sequence SEQ ID NO: 8, a CDR-L1 having amino acid sequence SEQ ID NO: 13, a CDR-L2 having amino acid sequence SEQ ID NO: 18, and a CDR-L3 having amino acid sequence SEQ ID NO: 21; b) an antibody comprising a CDR-H1 having amino acid sequence SEQ ID NO: 4, a CDR-H2 having amino acid sequence SEQ ID NO: 6, a CDR-H3 having amino acid sequence SEQ ID NO: 9, a CDR-L1 having amino acid sequence SEQ ID NO: 13, a CDR-L2 having amino acid sequence SEQ ID NO: 18, and a CDR-L3 having amino acid sequence SEQ ID NO: 21; c) an antibody comprising a CDR-H1 having amino acid sequence SEQ ID NO: 4, a CDR-H2 having amino acid sequence SEQ ID NO: 6, a CDR-H3 having amino acid sequence SEQ ID NO: 8, a CDR-L1 having amino acid sequence SEQ ID NO: 14, a CDR-L2 having amino acid sequence SEQ ID NO: 18, and a CDR-L3 having amino acid sequence SEQ ID NO: 21; d) an antibody comprising a CDR-H1 having amino acid sequence SEQ ID NO: 4, a CDR-H2 having amino acid sequence SEQ ID NO: 6, a CDR-H3 having amino acid sequence SEQ ID NO: 8, a CDR-L1 having amino acid sequence SEQ ID NO: 13, a CDR-L2 having amino acid sequence SEQ ID NO: 19, and a CDR-L3 having amino acid sequence SEQ ID NO: 21; e) an antibody comprising a CDR-H1 having an amino acid sequence SEQ ID NO: 4, a CDR-H2 having amino acid sequence SEQ ID NO: 6, a CDR-H3 having amino acid sequence SEQ ID NO: 8, a CDR-L1 having amino acid sequence SEQ ID NO: 15, a CDR-L2 having amino acid sequence SEQ ID NO: 18, and a CDR-L3 having amino acid sequence SEQ ID NO: 22; f) an antibody comprising a CDR-H1 having amino acid sequence SEQ ID NO: 4, a CDR-H2 having amino acid sequence SEQ ID NO: 6, a CDR-H3 having amino acid sequence SEQ ID NO: 9, a CDR-L1 having amino acid sequence SEQ ID NO: 15, a CDR-L2 having amino acid sequence SEQ ID NO: 18, and a CDR-L3 having amino acid sequence SEQ ID NO: 21; and g) an antibody comprising a CDR-H1 having amino acid sequence SEQ ID NO: 4, a CDR-H2 having amino acid sequence SEQ ID NO: 6, a CDR-H3 having amino acid sequence SEQ ID NO: 9, a CDR-L1 having amino acid sequence SEQ ID NO: 13, a CDR-L2 having amino acid sequence SEQ ID NO: 18, and a CDR-L3 having amino acid sequence SEQ ID NO: 21.

In some cases, the antibody competes for binding to a Botulinum neurotoxin with an antibody comprising a CDR-H1 having amino acid sequence SEQ ID NO: 4, a CDR-H2 having amino acid sequence SEQ ID NO: 6, a CDR-H3 having amino acid sequence SEQ ID NO: 9, a CDR-L1 having amino acid sequence SEQ ID NO: 15, a CDR-L2 having amino acid sequence SEQ ID NO: 18, a CDR-L3 having amino acid sequence SEQ ID NO: 21.

The present disclosure provides an antibody that competes for binding to a Botulinum neurotoxin with an antibody comprising a complementarity-determining region (CDR) having amino acid sequence selected from the group consisting of: SEQ ID NO: 4, SEQ ID NO: 6, SEQ ID NO: 8, SEQ ID NO: 13, SEQ ID NO: 18, and SEQ ID NO: 21; an antibody comprising a CDR having an amino acid sequence selected from the group consisting of: SEQ ID NO: 4, SEQ ID NO: 6, SEQ ID NO: 9, SEQ ID NO: 13, SEQ ID NO: 18, and SEQ ID NO: 21; an antibody comprising a CDR having an amino acid sequence selected from the group consisting of: SEQ ID NO: 4, SEQ ID NO: 6, SEQ ID NO: 6, SEQ ID NO: 14, SEQ ID NO: 18, and SEQ ID NO: 21; an antibody comprising a CDR having an amino acid sequence selected from the group consisting of: SEQ ID NO: 4, SEQ ID NO: 6, SEQ ID NO: 8, SEQ ID NO: 13, SEQ ID NO: 19, and SEQ ID NO: 21; an antibody comprising a CDR having an amino acid sequence selected from the group consisting of: SEQ ID NO: 4, SEQ ID NO: 6, SEQ ID NO: 8, SEQ ID NO: 15, SEQ ID NO: 18, and SEQ ID NO: 22; an antibody comprising a CDR having an amino acid sequence selected from the group consisting of: SEQ ID NO: 4, SEQ ID NO: 6, SEQ ID NO: 9, SEQ ID NO: 15, SEQ ID NO: 18, and SEQ ID NO: 21; and an antibody comprising a CDR having an amino acid sequence selected from the group consisting of: SEQ ID NO: 4, SEQ ID NO: 6, SEQ ID NO: 9, SEQ ID NO: 13, SEQ ID NO: 18, and SEQ ID NO: 21.

The present disclosure provides an antibody that binds to a Botulinum neurotoxin, wherein the antibody is selected from the group consisting of: a) an antibody comprising a CDR-H1 having amino acid sequence SEQ ID NO: 4, a CDR-H2 having amino acid sequence SEQ ID NO: 6, a CDR-H3 having amino acid sequence SEQ ID NO: 8, a CDR-L1 having amino acid sequence SEQ ID NO: 13, a CDR-L2 having amino acid sequence SEQ ID NO: 18, and a CDR-L3 having amino acid sequence SEQ ID NO: 21; b) an antibody comprising a CDR-H1 having amino acid sequence SEQ ID NO: 4, a CDR-H2 having amino acid sequence SEQ ID NO: 6, a CDR-H3 having amino acid sequence SEQ ID NO: 9, a CDR-L1 having amino acid sequence SEQ ID NO: 13, a CDR-L2 having amino acid sequence SEQ ID NO: 18, and a CDR-L3 having amino acid sequence SEQ ID NO: 21; c) an antibody comprising a CDR-H1 having amino acid sequence SEQ ID NO: 4, a CDR-H2 having amino acid sequence SEQ ID NO: 6, a CDR-H3 having amino acid sequence SEQ ID NO: 8, a CDR-L1 having amino acid sequence SEQ ID NO: 14, a CDR-L2 having amino acid sequence SEQ ID NO: 18, and a CDR-L3 having amino acid sequence SEQ ID NO: 21; d) an antibody comprising a CDR-H1 having amino acid sequence SEQ ID NO: 4, a CDR-H2 having amino acid sequence SEQ ID NO: 6, a CDR-H3 having amino acid sequence SEQ ID NO: 8, a CDR-L1 having amino acid sequence SEQ ID NO: 13, a CDR-L2 having amino acid sequence SEQ ID NO: 19, and a CDR-L3 having amino acid sequence SEQ ID NO: 21; e) an antibody comprising a CDR-H1 having an amino acid sequence SEQ ID NO: 4, a CDR-H2 having amino acid sequence SEQ ID NO: 6, a CDR-H3 having amino acid sequence SEQ ID NO: 8, a CDR-L1 having amino acid sequence SEQ ID NO: 15, a CDR-L2 having amino acid sequence SEQ ID NO: 18, and a CDR-L3 having amino acid sequence SEQ ID NO: 22; f) an antibody comprising a CDR-H1 having amino acid sequence SEQ ID NO: 4, a CDR-H2 having amino acid sequence SEQ ID NO: 6, a CDR-H3 having amino acid sequence SEQ ID NO: 9, a CDR-L1 having amino acid sequence SEQ ID NO: 15, a CDR-L2 having amino acid sequence SEQ ID NO: 18, and a CDR-L3 having amino acid sequence SEQ ID NO: 21; and g) an antibody comprising a CDR-H1 having amino acid sequence SEQ ID NO: 4, a CDR-H2 having amino acid sequence SEQ ID NO: 6, a CDR-H3 having amino acid sequence SEQ ID NO: 9, a CDR-L1 having amino acid sequence SEQ ID NO: 13, a CDR-L2 having amino acid sequence SEQ ID NO: 18, and a CDR-L3 having amino acid sequence SEQ ID NO: 21.

The present disclosure provides an antibody that binds to a Botulinum neurotoxin, wherein the antibody comprises a complementarity-determining region (CDR) having amino acid sequence selected from the group consisting of: SEQ ID NO: 4, SEQ ID NO: 6, SEQ ID NO: 8, SEQ ID NO: 13, SEQ ID NO: 18, and SEQ ID NO: 21; an antibody comprising a CDR having an amino acid sequence selected from the group consisting of: SEQ ID NO: 4, SEQ ID NO: 6, SEQ ID NO: 9, SEQ ID NO: 13, SEQ ID NO: 18, and SEQ ID NO: 21; an antibody comprising a CDR having an amino acid sequence selected from the group consisting of: SEQ ID NO: 4, SEQ ID NO: 6, SEQ ID NO: 6, SEQ ID NO: 14, SEQ ID NO: 18, and SEQ ID NO: 21; an antibody comprising a CDR having an amino acid sequence selected from the group consisting of: SEQ ID NO: 4, SEQ ID NO: 6, SEQ ID NO: 8, SEQ ID NO: 13, SEQ ID NO: 19, and SEQ ID NO: 21; an antibody comprising a CDR having an amino acid sequence selected from the group consisting of: SEQ ID NO: 4, SEQ ID NO: 6, SEQ ID NO: 8, SEQ ID NO: 15, SEQ ID NO: 18, and SEQ ID NO: 22; an antibody comprising a CDR having an amino acid sequence selected from the group consisting of: SEQ ID NO: 4, SEQ ID NO: 6, SEQ ID NO: 9, SEQ ID NO: 15, SEQ ID NO: 18, and SEQ ID NO: 21; and an antibody comprising a CDR having an amino acid sequence selected from the group consisting of: SEQ ID NO: 4, SEQ ID NO: 6, SEQ ID NO: 9, SEQ ID NO: 13, SEQ ID NO: 18, and SEQ ID NO: 21.

In some cases, the antibody that binds to a Botulinum neurotoxin comprises a CDR-H1 having amino acid sequence SEQ ID NO: 4, a CDR-H2 having amino acid sequence SEQ ID NO: 6, a CDR-H3 having amino acid sequence SEQ ID NO: 9, a CDR-L1 having amino acid sequence SEQ ID NO: 15, a CDR-L2 having amino acid sequence SEQ ID NO: 18, a CDR-L3 having amino acid sequence SEQ ID NO: 21.

In some cases, the antibody that binds to a Botulinum neurotoxin comprises a full length $V_H$ comprising an amino acid sequence of the full length $V_H$ of 4C10.20; and a full length $V_L$ comprising an amino acid sequence of the full length $V_H$ of 4C10.20.

In some cases, the antibody competes for binding to a Botulinum neurotoxin with an antibody comprising a full length $V_H$ comprising an amino acid sequence of the full length $V_H$ of 4C10.20; and a full length $V_L$ comprising an amino acid sequence of the full length $V_H$ of 4C10.20.

In some cases, the antibody competes for binding to a Botulinum neurotoxin with an antibody comprising: a) a $V_H$ CDR1 comprising the amino acid sequence of $V_H$ CDR1 of 4C10.20, a $V_H$ CDR2 comprising the amino acid sequence of $V_H$ CDR2 of 4C10.20, and a $V_H$ CDR3 comprising the amino acid sequence of $V_H$ CDR3 of 4C10.20; b) a $V_L$ CDR1 comprising the amino acid sequence of $V_L$ CDR1 of 4C10.20, a $V_L$ CDR2 comprising an amino acid sequence of $V_L$ CDR2 of 4C10.20, and a $V_L$ CDR3 comprising an amino acid sequence of $V_L$ CDR3 of 4C10.20; c) a full length $V_H$ comprising an amino acid sequence of the full length $V_H$ of 4C10.20; or d) a full length $V_L$ comprising an amino acid sequence of the full length $V_L$ of 4C10.20.

In some cases, the antibody competes for binding to a Botulinum neurotoxin with an antibody comprising a $V_H$ CDR1 comprising the amino acid sequence of $V_H$ CDR1 of 4C10.20; a $V_H$ CDR2 comprising the amino acid sequence of $V_H$ CDR2 of 4C10.20; and a $V_H$ CDR3 comprising the amino acid sequence of $V_H$ CDR3 of 4C10.20.

In some cases, the antibody competes for binding to a Botulinum neurotoxin with an antibody comprising a $V_L$ CDR1 comprising the amino acid sequence of $V_L$ CDR1 of 4C10.20; a $V_L$ CDR2 comprising the amino acid sequence of $V_L$ CDR2 of 4C10.20; and a $V_L$ CDR3 comprising the amino acid sequence of $V_L$ CDR3 of 4C10.20.

In some cases, the antibody competes for binding to a Botulinum neurotoxin with an antibody comprising: a) a $V_H$ CDR1 comprising the amino acid sequence of $V_H$ CDR1 of 4C10.20, a $V_H$ CDR2 comprises the amino acid sequence of $V_H$ CDR2 of 4C10. 20, and a $V_H$ CDR3 comprising an amino acid sequence of $V_H$ CDR3 of 4C10.20; b) a $V_L$ CDR1 comprising an amino acid sequence of $V_L$ CDR1 of an antibody selected from the group consisting of 4C10.5, 4C10.8, 4C10.15, 4C10.17, 4C10.18, or 4C10.22; c) a $V_L$ CDR2 comprising an amino acid sequence of $V_L$ CDR2 of an antibody selected from the group consisting of 4C10.5, 4C10.8, 4C10.15, 4C10.17, 4C10.18, or 4C10.22; and d) a $V_L$ CDR3 comprising an amino acid sequence of $V_L$ CDR3 of an antibody selected from the group consisting of 4C10.5, 4C10.8, 4C10.15, 4C10.17, 4C10.18, or 4C10.22.

Aspects of the present disclosure also include antibodies that encompass those that bind to a BoNT with an antibody that includes one or more of the $V_H$ CDRs set forth in FIG. 1 or FIG. 2 and/or one or more of the $V_L$ CDRs set forth in FIG. 1 or FIG. 2.

In some cases, the antibody is an antibody that binds to a Botulinum neurotoxin, wherein the antibody comprises: a $V_H$ CDR1 comprising an amino acid sequence of $V_H$ CDR1 of 4C10.20; a $V_H$ CDR2 comprising an amino acid sequence of $V_H$ CDR2 of 4C10.20; a $V_H$ CDR3 comprising an amino acid sequence of $V_H$ CDR3 of 4C10.20; a $V_L$ CDR1 comprising an amino acid sequence of $V_L$ CDR1 of 4C10.20; a $V_L$ CDR2 comprising an amino acid sequence of $V_L$ CDR2 of 4C10.20; and a $V_L$ CDR3 comprising an amino acid sequence of $V_L$ CDR3 of 4C10.20.

In some cases, the isolated antibody that binds to a Botulinum neurotoxin, comprises: a) a full length $V_H$ comprising an amino acid sequence of the full length $V_H$ of 4C10.20; b) a full length $V_L$ comprising an amino acid sequence of the full length $V_L$ of 4C10.20; c) a $V_H$ CDR1 comprising the amino acid sequence of $V_H$ CDR1 of 4C10.20, a $V_H$ CDR2 comprising the amino acid sequence of $V_H$ CDR2 of 4C10.20; and a $V_H$ CDR3 comprising the amino acid sequence of $V_H$ CDR3 of 4C10.20; d) a $V_L$ CDR1 comprising an amino acid sequence of $V_L$ CDR1 of 4C10.20, a $V_L$ CDR2 comprising the amino acid sequence of $V_L$ CDR2 of 4C10.20, and a $V_L$ CDR3 comprising the amino acid sequence of $V_L$ CDR3 of 4C10.20; e) a $V_H$ CDR1 comprising the amino acid sequence of $V_H$ CDR1 of 4C10.20, a $V_H$ CDR2 comprising the amino acid sequence of $V_H$ CDR2 of 4C10.20, a $V_H$ CDR3 comprising the amino acid sequence of $V_H$ CDR3 of 4C10.20, a $V_L$ CDR1 comprising the amino acid sequence of $V_L$ CDR1 of 4C10.20, a $V_L$ CDR2 comprising the amino acid sequence of $V_L$ CDR2 of 4C10.20, and a $V_L$ CDR3 comprising the amino acid sequence of $V_L$ CDR3 of 4C10.20; or f) a full length $V_H$ comprising the amino acid sequence of the full length $V_H$ of 4C10.20, and a full length $V_L$ comprising the amino acid sequence of the full length $V_L$ of 4C10.20.

In some cases, the isolated antibody that binds to a Botulinum neurotoxin comprises the full length $V_H$ comprising the amino acid sequence of the full length $V_H$ of 4C10.20.

In some cases, the isolated antibody that binds to a Botulinum neurotoxin comprises the full length $V_L$ comprising the amino acid sequence of the full length $V_L$ of 4C10.20.

In some cases, the isolated antibody that binds to a Botulinum neurotoxin comprises the full length $V_H$ comprising the amino acid sequence of the full length $V_H$ of 4C10.20; and the full length $V_L$ comprising the amino acid sequence of the full length $V_L$ of 4C10.20.

In some cases, the isolated antibody that binds to a Botulinum neurotoxin comprises: a) a $V_H$ CDR1 comprising the amino acid sequence of $V_H$ CDR1 of 4C10.20, a $V_H$ CDR2 comprising the amino acid sequence of $V_H$ CDR2 of 4C10.20, a $V_H$ CDR3 comprising the amino acid sequence of $V_H$ CDR3 of 4C10.20; and b) a $V_L$ CDR1 comprising the amino acid sequence of $V_L$ CDR1 of 4C10.20, a $V_L$ CDR2 comprising the amino acid sequence of $V_L$ CDR2 of 4C10.20, and a $V_L$ CDR3 comprising the amino acid sequence of $V_L$ CDR3 of 4C10.20.

In some cases, the antibody competes for binding to a Botulinum neurotoxin with an antibody comprising: a) a $V_H$ CDR1 comprising the amino acid sequence of $V_H$ CDR1 of 4C10.8, a $V_H$ CDR2 comprising the amino acid sequence of $V_H$ CDR2 of 4C10.8, and a $V_H$ CDR3 comprising the amino acid sequence of $V_H$ CDR3 of 4C10.8; b) a $V_L$ CDR1 comprising the amino acid sequence of $V_L$ CDR1 of 4C10.8, a $V_L$ CDR2 comprising the amino acid sequence of $V_L$ CDR2 of 4C10.8, and a $V_L$ CDR3 comprising the amino acid sequence of $V_L$ CDR3 of 4C10.8; c) a $V_H$ CDR1 comprising the amino acid sequence of $V_H$ CDR1 of 4C10.8, a $V_H$ CDR2 comprising the amino acid sequence of $V_H$ CDR2 of 4C10.8, a $V_H$ CDR3 comprising the amino acid sequence of $V_H$ CDR3 of 4C10.8, a $V_L$ CDR1 comprising the amino acid sequence of $V_L$ CDR1 of 4C10.8, a $V_L$ CDR2 comprising the amino acid sequence of $V_L$ CDR2 of 4C10.8, and a $V_L$ CDR3 comprising the amino acid sequence of $V_L$ CDR3 of 4C10.8; or d) a full length $V_H$ comprising the amino acid sequence of the full length $V_H$ of 4C10.8, and a full length $V_L$ comprising the amino acid sequence of the full length $V_L$ of 4C10.8.

In some cases, the antibody competes for binding to a Botulinum neurotoxin with an antibody comprising: a) a $V_H$ CDR1 comprising the amino acid sequence of $V_H$ CDR1 of 4C10.15, a $V_H$ CDR2 comprising the amino acid sequence of $V_H$ CDR2 of 4C10.15, and a $V_H$ CDR3 comprising the amino acid sequence of $V_H$ CDR3 of 4C10.15; b) a $V_L$ CDR1 comprising the amino acid sequence of $V_L$ CDR1 of 4C10.15, a $V_L$ CDR2 comprising the amino acid sequence of $V_L$ CDR2 of 4C10.15, and a $V_L$ CDR3 comprising the amino acid sequence of $V_L$ CDR3 of 4C10.15; c) a $V_H$ CDR1 comprising the amino acid sequence of $V_H$ CDR1 of 4C10.15, a $V_H$ CDR2 comprising the amino acid sequence of $V_H$ CDR2 of 4C10.15, a $V_H$ CDR3 comprising the amino acid sequence of $V_H$ CDR3 of 4C10.15, a $V_L$ CDR1 comprising the amino acid sequence of $V_L$ CDR1 of 4C10.15, a $V_L$ CDR2 comprising the amino acid sequence of $V_L$ CDR2 of 4C10.15, and a $V_L$ CDR3 comprising the amino acid sequence of $V_L$ CDR3 of 4C10.15; or d) a full length $V_H$ comprising the amino acid sequence of the full length $V_H$ of 4C10.15, and a full length $V_L$ comprising the amino acid sequence of the full length $V_L$ of 4C10.15.

In some cases, the antibody competes for binding to a Botulinum neurotoxin with an antibody comprising: a) a $V_H$ CDR1 comprising the amino acid sequence of $V_H$ CDR1 of 4C10.17, a $V_H$ CDR2 comprising the amino acid sequence of $V_H$ CDR2 of 4C10.17, and a $V_H$ CDR3 comprising the amino acid sequence of $V_H$ CDR3 of 4C10.17; b) a $V_L$ CDR1 comprising the amino acid sequence of $V_L$ CDR1 of 4C10.17, a $V_L$ CDR2 comprising the amino acid sequence of $V_L$ CDR2 of 4C10.17, and a $V_L$ CDR3 comprising the amino acid sequence of $V_L$ CDR3 of 4C10.17; c) a $V_H$ CDR1 comprising the amino acid sequence of $V_H$ CDR1 of 4C10.17, a $V_H$ CDR2 comprising the amino acid sequence of $V_H$ CDR2 of 4C10.17, a $V_H$ CDR3 comprising the amino acid sequence of $V_H$ CDR3 of 4C10.17, a $V_L$ CDR1 comprising the amino acid sequence of $V_L$ CDR1 of 4C10.17, a $V_L$ CDR2 comprising the amino acid sequence of $V_L$ CDR2 of 4C10.17, and a $V_L$ CDR3 comprising the amino acid sequence of $V_L$ CDR3 of 4C10.17; or d) a full length $V_H$ comprising the amino acid sequence of the full length $V_H$ of 4C10.17, and a full length $V_L$ comprising the amino acid sequence of the full length $V_L$ of 4C10.17.

In some cases, the antibody competes for binding to a Botulinum neurotoxin with an antibody comprising: a) a $V_H$ CDR1 comprising the amino acid sequence of $V_H$ CDR1 of 4C10.18, a $V_H$ CDR2 comprising the amino acid sequence of $V_H$ CDR2 of 4C10.18, and a $V_H$ CDR3 comprising an amino acid sequence of $V_H$ CDR3 of 4C10.18; b) a $V_L$ CDR1 comprising the amino acid sequence of $V_L$ CDR1 of 4C10.18, a $V_L$ CDR2 comprising the amino acid sequence of $V_L$ CDR2 of 4C10.18, and a $V_L$ CDR3 comprising the amino acid sequence of $V_L$ CDR3 of 4C10.18; c) a $V_H$ CDR1 comprising the amino acid sequence of $V_H$ CDR1 of 4C10.18, a $V_H$ CDR2 comprising the amino acid sequence of $V_H$ CDR2 of 4C10.18, a $V_H$ CDR3 comprising the amino acid sequence of $V_H$ CDR3 of 4C10.18, a $V_L$ CDR1 comprising the amino acid sequence of $V_L$ CDR1 of 4C10.18, a $V_L$ CDR2 comprising the amino acid sequence of $V_L$ CDR2 of 4C10.18, and a $V_L$ CDR3 comprising the amino acid sequence of $V_L$ CDR3 of 4C10.18; or d) a full length $V_H$ comprising the amino acid sequence of the full length $V_H$ of 4C10.18, and a full length $V_L$ comprising the amino acid sequence of the full length $V_L$ of 4C10.18.

In some cases, the antibody competes for binding to a Botulinum neurotoxin with an antibody comprising: a) a $V_H$ CDR1 comprising the amino acid sequence of $V_H$ CDR1 of 4C10.5, a $V_H$ CDR2 comprising the amino acid sequence of $V_H$ CDR2 of 4C10.5, and a $V_H$ CDR3 comprising the amino acid sequence of $V_H$ CDR3 of 4C10.5; b) a $V_L$ CDR1 comprising the amino acid sequence of $V_L$ CDR1 of 4C10.5, a $V_L$ CDR2 comprising the amino acid sequence of $V_L$ CDR2 of 4C10.5, and a $V_L$ CDR3 comprising the amino acid sequence of $V_L$ CDR3 of 4C10.5; c) a $V_H$ CDR1 comprising the amino acid sequence of $V_H$ CDR1 of 4C10.5, a $V_H$ CDR2 comprising the amino acid sequence of $V_H$ CDR2 of 4C10.5, a $V_H$ CDR3 comprising the amino acid sequence of $V_H$ CDR3 of 4C10.5, a $V_L$ CDR1 comprising the amino acid sequence of $V_L$ CDR1 of 4C10.5, a $V_L$ CDR2 comprising the amino acid sequence of $V_L$ CDR2 of 4C10.20, and a $V_L$ CDR3 comprising the amino acid sequence of $V_L$ CDR3 of 4C10.5; or d) a full length $V_H$ comprising the amino acid sequence of the full length $V_H$ of 4C10.5, and a full length $V_L$ comprising the amino acid sequence of the full length $V_L$ of 4C10.5.

In some cases, the antibody competes for binding to a Botulinum neurotoxin with an antibody comprising: a) a $V_H$ CDR1 comprising the amino acid sequence of $V_H$ CDR1 of 4C10.22, a $V_H$ CDR2 comprising the amino acid sequence of $V_H$ CDR2 of 4C10.22, and a $V_H$ CDR3 comprising the amino acid sequence of $V_H$ CDR3 of 4C10.22; b) a $V_L$ CDR1 comprising the amino acid sequence of $V_L$ CDR1 of 4C10.22, a $V_L$ CDR2 comprising the amino acid sequence of $V_L$ CDR2 of 4C10.22, and a $V_L$ CDR3 comprising the amino acid sequence of $V_L$ CDR3 of 4C10.22; c) a $V_H$ CDR1 comprising the amino acid sequence of $V_H$ CDR1 of 4C10.22, a $V_H$ CDR2 comprising the amino acid sequence of $V_H$ CDR2 of 4C10.22, a $V_H$ CDR3 comprising the amino acid sequence of $V_H$ CDR3 of 4C10.22, a $V_L$ CDR1 comprising the amino acid sequence of $V_L$ CDR1 of 4C10.22, a $V_L$ CDR2 comprising the amino acid sequence of $V_L$ CDR2 of 4C10.22, and a $V_L$ CDR3 comprising the amino acid sequence of $V_L$ CDR3 of 4C10.22; or d) a full length $V_H$ comprising the amino acid sequence of the full length $V_H$ of 4C10.22, and a full length $V_L$ comprising the amino acid sequence of the full length $V_L$ of 4C10.22.

In some cases, the antibody competes for binding to a Botulinum neurotoxin with an antibody comprising: a) a $V_H$ CDR1 comprising the amino acid sequence of $V_H$ CDR1 of 4C10.5, a $V_H$ CDR2 comprising the amino acid sequence of $V_H$ CDR2 of 4C10.5, and a $V_H$ CDR3 comprising the amino acid sequence of $V_H$ CDR3 of 4C10.5; and b) a $V_L$ CDR1 comprising the amino acid sequence of $V_L$ CDR1 of an antibody selected from the group consisting of 4C10.8, 4C10.15, 4C10.17, 4C10.18, 4C10.20, and 4C10.22, a $V_L$ CDR2 comprising the amino acid sequence of $V_L$ CDR2 selected from the group consisting of 4C10.8, 4C10.15, 4C10.17, 4C10.18, 4C10.20, and 4C10.22, and a VL CDR3 comprising the amino acid sequence of $V_L$ CDR3 of an antibody selected from the group consisting of 4C10.8, 4C10.15, 4C10.17, 4C10.18, 4C10.20, and 4C10.22.

In some cases, the antibody competes for binding to a Botulinum neurotoxin with an antibody comprising: a) a $V_H$ CDR1 comprising the amino acid sequence of $V_H$ CDR1 of 4C10.8, a $V_H$ CDR2 comprising the amino acid sequence of $V_H$ CDR2 of 4C10.8, and a $V_H$ CDR3 comprising the amino acid sequence of $V_H$ CDR3 of 4C10.8; and b) a $V_L$ CDR1 comprising the amino acid sequence of $V_L$ CDR1 of an antibody selected from the group consisting of 4C10.5, 4C10.15, 4C10.17, 4C10.18, 4C10.20, and 4C10.22, a $V_L$ CDR2 comprising the amino acid sequence of $V_L$ CDR2 of an antibody selected from the group consisting of 4C10.5, 4C10.15, 4C10.17, 4C10.18, 4C10.20, and 4C10.22, and a $V_L$ CDR3 comprising the amino acid sequence of $V_L$ CDR3 of an antibody selected from the group consisting of 4C10.5, 4C10.15, 4C10.17, 4C10.18, 4C10.20, and 4C10.22.

In some cases, the antibody competes for binding to a Botulinum neurotoxin with an antibody comprising: a) a $V_H$ CDR1 comprising the amino acid sequence of $V_H$ CDR1 of 4C10.15, a $V_H$ CDR2 comprising the amino acid sequence of $V_H$ CDR2 of 4C10.15, and a $V_H$ CDR3 comprising the amino acid sequence of $V_H$ CDR3 of 4C10.15; and b) a $V_L$ CDR1 comprising the amino acid sequence of $V_L$ CDR1 of an antibody selected from the group consisting of 4C10.5, 4C10.8, 4C10.17, 4C10.18, 4C10.20, and 4C10.22, a $V_L$ CDR2 comprising the amino acid sequence of $V_L$ CDR2 of an antibody selected from the group consisting of 4C10.5, 4C10.8, 4C10.17, 4C10.18, 4C10.20, and 4C10.22, and a $V_L$ CDR3 comprising an amino acid sequence of $V_L$ CDR3 of an antibody selected from the group consisting of 4C10.5, 4C10.8, 4C10.17, 4C10.18, 4C10.20, and 4C10.22.

In some cases, the antibody competes for binding to a Botulinum neurotoxin with an antibody comprising: a) a $V_H$ CDR1 comprising the amino acid sequence of $V_H$ CDR1 of 4C10.17, a $V_H$ CDR2 comprising the amino acid sequence of $V_H$ CDR2 of 4C10.17, and a $V_H$ CDR3 comprising the amino acid sequence of $V_H$ CDR3 of 4C10.17; and b) a $V_L$ CDR1 comprising the amino acid sequence of $V_L$ CDR1 of an antibody selected from the group consisting of 4C10.5, 4C10.8, 4C10.15, 4C10.18, 4C10.20, and 4C10.22, a $V_L$ CDR2 comprising the amino acid sequence of $V_L$ CDR2 of an antibody selected from the group consisting of 4C10.5, 4C10.8, 4C10.15, 4C10.18, 4C10.20, and 4C10.22, and a $V_L$ CDR3 comprising the amino acid sequence of $V_L$ CDR3 of an antibody selected from the group consisting of 4C10.5, 4C10.8, 4C10.15, 4C10.18, 4C10.20, and 4C10.22.

In some cases, the antibody competes for binding to a Botulinum neurotoxin with an antibody comprising: a) a $V_H$ CDR1 comprising the amino acid sequence of $V_H$ CDR1 of 4C10.18, a $V_H$ CDR2 comprising the amino acid sequence of $V_H$ CDR2 of 4C10.18, and a $V_H$ CDR3 comprising the amino acid sequence of $V_H$ CDR3 of 4C10.18; and b) a $V_L$ CDR1 comprising the amino acid sequence of $V_L$ CDR1 of an antibody selected from the group consisting of 4C10.5, 4C10.8, 4C10.15, 4C10.17, 4C10.20, and 4C10.22, a $V_L$ CDR2 comprising the amino acid sequence of $V_L$ CDR2 of an antibody selected from the group consisting of 4C10.5, 4C10.8, 4C10.15, 4C10.17, 4C10.20, and 4C10.22, and a $V_L$ CDR3 comprising the amino acid sequence of $V_L$ CDR3 of an antibody selected from the group consisting of 4C10.5, 4C10.8, 4C10.15, 4C10.17, 4C10.20, and 4C10.22.

In some cases, the antibody competes for binding to a Botulinum neurotoxin with an antibody comprising: a) a $V_H$ CDR1 comprising the amino acid sequence of $V_H$ CDR1 of 4C10.20, a $V_H$ CDR2 comprising the amino acid sequence of $V_H$ CDR2 of 4C10. 20, and a $V_H$ CDR3 comprising the amino acid sequence of $V_H$ CDR3 of 4C10. 20; and b) a $V_L$ CDR1 comprising the amino acid sequence of $V_L$ CDR1 of an antibody selected from the group consisting of 4C10.5, 4C10.8, 4C10.15, 4C10.17, 4C10.18, and 4C10.22, a $V_L$ CDR2 comprising the amino acid sequence of $V_L$ CDR2 of an antibody selected from the group consisting of 4C10.5, 4C10.8, 4C10.15, 4C10.17, 4C10.18, and 4C10.22, and a $V_L$ CDR3 comprising the amino acid sequence of $V_L$ CDR3 of an antibody selected from the group consisting of 4C10.5, 4C10.8, 4C10.15, 4C10.17, 4C10.18, and 4C10.22.

In some cases, the antibody competes for binding to a Botulinum neurotoxin with an antibody comprising: a) a $V_H$ CDR1 comprising the amino acid sequence of $V_H$ CDR1 of 4C10.22, a $V_H$ CDR2 comprising an amino acid sequence of $V_H$ CDR2 of 4C10. 22, and a $V_H$ CDR3 comprising the amino acid sequence of $V_H$ CDR3 of 4C10. 22; and b) a $V_L$ CDR1 comprising the amino acid sequence of $V_L$ CDR1 of an antibody selected from the group consisting of 4C10.5, 4C10.8, 4C10.15, 4C10.17, 4C10.18, and 4C10.20, a $V_L$ CDR2 comprising the amino acid sequence of $V_L$ CDR2 of an antibody selected from the group consisting of 4C10.5, 4C10.8, 4C10.15, 4C10.17, 4C10.18, and 4C10.20, and a $V_L$ CDR3 comprising the amino acid sequence of $V_L$ CDR3 of an antibody selected from the group consisting of 4C10.5, 4C10.8, 4C10.15, 4C10.17, 4C10.18, and 4C10.20.

In some cases, the competes for binding to a Botulinum neurotoxin with an antibody comprising: a) a $V_H$ CDR1 comprising the amino acid sequence of $V_H$ CDR1 of an antibody selected from the group consisting of 4C10.8, 4C10.15, 4C10.17, 4C10.18, 4C10.20, and 4C10.22, a $V_H$ CDR2 comprising the amino acid sequence of $V_H$ CDR2 of an antibody selected from the group consisting of 4C10.8, 4C10.15, 4C10.17, 4C10.18, 4C10.20, and 4C10.22, and a $V_H$ CDR3 comprising the amino acid sequence of $V_H$ CDR3 of an antibody of selected from the group consisting of 4C10.8, 4C10.15, 4C10.17, 4C10.18, 4C10.20, and 4C10.22; and b) a $V_L$ CDR1 comprising the amino acid sequence of $V_L$ CDR1 of 4C10.5; a $V_L$ CDR2 comprising an amino acid sequence of $V_L$ CDR2 of 4C10.5; and a $V_L$ CDR3 comprising the amino acid sequence of $V_L$ CDR3 of 4C10.5.

In some cases, the antibody competes for binding to a Botulinum neurotoxin with an antibody comprising: a) a $V_H$ CDR1 comprising the amino acid sequence of $V_H$ CDR1 of an antibody selected from the group consisting of 4C10.5, 4C10.15, 4C10.17, 4C10.18, 4C10.20, and 4C10.22, a $V_H$ CDR2 comprising the amino acid sequence of $V_H$ CDR2 of an antibody selected from the group consisting of 4C10.5, 4C10.15, 4C10.17, 4C10.18, 4C10.20, and 4C10.22, and a $V_H$ CDR3 comprising the amino acid sequence of $V_H$ CDR3 of an antibody selected from the group consisting of 4C10.5, 4C10.15, 4C10.17, 4C10.18, 4C10.20, and 4C10.22; and b) a $V_L$ CDR1 comprising the amino acid sequence of $V_L$ CDR1 of 4C10.8, a $V_L$ CDR2 comprising the amino acid sequence of $V_L$ CDR2 of 4C10.8, and a $V_L$ CDR3 comprising the amino acid sequence of $V_L$ CDR3 of 4C10.8.

In some cases, the antibody competes for binding to a Botulinum neurotoxin with an antibody comprising: a) a $V_H$ CDR1 comprising the amino acid sequence of $V_H$ CDR1 of an antibody selected from the group consisting of 4C10.5, 4C10.8, 4C10.17, 4C10.18, 4C10.20, and 4C10.22, a $V_H$ CDR2 comprising the amino acid sequence of $V_H$ CDR2 of an antibody selected from the group consisting of 4C10.5, 4C10.8, 4C10.17, 4C10.18, 4C10.20, and 4C10.22, and a $V_H$ CDR3 comprising the amino acid sequence of $V_H$ CDR3 of an antibody selected from the group consisting of 4C10.5, 4C10.8, 4C10.17, 4C10.18, 4C10.20, and 4C10.22; and b) a $V_L$ CDR1 comprising the amino acid sequence of $V_L$ CDR1 of 4C10.15, a $V_L$ CDR2 comprising the amino acid sequence of $V_L$ CDR2 of 4C10.15, and a $V_L$ CDR3 comprising an amino acid sequence of $V_L$ CDR3 of 4C10.15.

In some cases, the antibody competes for binding to a Botulinum neurotoxin with an antibody comprising: a) a $V_H$ CDR1 comprising the amino acid sequence of $V_H$ CDR1 of an antibody selected from the group consisting of 4C10.5, 4C10.8, 4C10.15, 4C10.18, 4C10.20, and 4C10.22, a $V_H$ CDR2 comprising the amino acid sequence of $V_H$ CDR2 of an antibody selected from the group consisting of 4C10.5, 4C10.8, 4C10.15, 4C10.18, 4C10.20, and 4C10.22, and a $V_H$ CDR3 comprising the amino acid sequence of $V_H$ CDR3 of an antibody selected from the group consisting of 4C10.5, 4C10.8, 4C10.15, 4C10.18, 4C10.20, and 4C10.22; and b) a $V_L$ CDR1 comprising the amino acid sequence of $V_L$ CDR1 of 4C10.17, a $V_L$ CDR2 comprising the amino acid sequence of $V_L$ CDR2 of 4C10.17, and a $V_L$ CDR3 comprising the amino acid sequence of $V_L$ CDR3 of 4C10.17.

In some cases, the antibody competes for binding to a Botulinum neurotoxin with an antibody comprising: a) a $V_H$ CDR1 comprising the amino acid sequence of $V_H$ CDR1 of an antibody selected from the group consisting of 4C10.5, 4C10.8, 4C10.15, 4C10.17, 4C10.20, and 4C10.22, a $V_H$ CDR2 comprising the amino acid sequence of $V_H$ CDR2 of an antibody selected from the group consisting of 4C10.5, 4C10.8, 4C10.15, 4C10.17, 4C10.20, and 4C10.22, and a $V_H$ CDR3 comprising the amino acid sequence of $V_H$ CDR3 of an antibody selected from the group consisting of 4C10.5, 4C10.8, 4C10.15, 4C10.17, 4C10.20, and 4C10.22; and b) a $V_L$ CDR1 comprising the amino acid sequence of $V_L$ CDR1 of 4C10.18, a $V_L$ CDR2 comprising the amino acid sequence of $V_L$ CDR2 of 4C10.18, and a $V_L$ CDR3 comprising the amino acid sequence of $V_L$ CDR3 of 4C10.18.

In some cases, the antibody competes for binding to a Botulinum neurotoxin with an antibody comprising: a) a $V_H$ CDR1 comprising the amino acid sequence of $V_H$ CDR1 of an antibody selected from the group consisting of 4C10.5, 4C10.8, 4C10.15, 4C10.17, 4C10.18, and 4C10.22, a $V_H$ CDR2 comprising the amino acid sequence of $V_H$ CDR2 of an antibody selected from the group consisting of 4C10.5, 4C10.8, 4C10.15, 4C10.17, 4C10.18, and 4C10.22, and a $V_H$ CDR3 comprising the amino acid sequence of $V_H$ CDR3 of an antibody selected from the group consisting of 4C10.5, 4C10.8, 4C10.15, 4C10.17, 4C10.18, and 4C10.22; and b) a $V_L$ CDR1 comprising the amino acid sequence of $V_L$ CDR1 of 4C10.20, a $V_L$ CDR2 comprising the amino acid sequence of $V_L$ CDR2 of 4C10.20, and a $V_L$ CDR3 comprising the amino acid sequence of $V_L$ CDR3 of 4C10.20.

In some cases, the antibody competes for binding to a Botulinum neurotoxin with an antibody comprising: a) a $V_H$ CDR1 comprising the amino acid sequence of $V_H$ CDR1 of an antibody selected from the group consisting of 4C10.5, 4C10.8, 4C10.15, 4C10.17, 4C10.18, and 4C1020, a $V_H$ CDR2 comprising the amino acid sequence of $V_H$ CDR2 selected from the group consisting of 4C10.5, 4C10.8, 4C10.15, 4C10.17, 4C10.18, and 4C1020, and a $V_H$ CDR3 comprising the amino acid sequence of $V_H$ CDR3 of selected from the group consisting of 4C10.5, 4C10.8, 4C10.15, 4C10.17, 4C10.18, and 4C1020; and b) a $V_L$ CDR1 comprising the amino acid sequence of $V_L$ CDR1 of 4C10.22, a $V_L$ CDR2 comprising the amino acid sequence of $V_L$ CDR2 of 4C10.22, and a $V_L$ CDR3 comprising the amino acid sequence of $V_L$ CDR3 of 4C10.22.

In some cases, the antibody competes for binding to a Botulinum neurotoxin with an antibody comprises a variable heavy chain (VH) polypeptide comprising a $V_H$ CDR1 selected from a $V_H$ of the antibody 4C10.20, a $V_H$ CDR2 selected from a $V_H$ of the antibody 4C10.20, and a $V_H$ CDR3 selected from a $V_H$ of the antibody 4C10.20; and a variable light chain (VL) polypeptide comprising a $V_L$ CDR1 selected from a $V_L$ of the antibody 4C10.20, a $V_L$ CDR2 selected from a $V_L$ of the antibody 4C10.20, and a $V_L$ CDR3 selected from a $V_L$ of the antibody 4C10.20.

For example, an antibody may have the binding specificity (i.e., in this context, the same CDRs, or substantially the same CDRs) of an antibody having one or more $V_H$ and $V_L$ CDRs or full length $V_H$ and/or $V_L$ as set forth in FIG. 1 or FIG. 2. An antibody of the present disclosure may therefore contain one or more CDR as set forth in a $V_H$ or $V_L$ sequence shown in FIG. 1 or FIG. 2 and, additionally, may have at least 80% identity, 85%, 90%, or 95% identity up to 100% identity of a full-length $V_H$ or $V_L$ sequence. For example, an antibody may contain the CDRs of a $V_H$ and a $V_L$ sequence and human framework sequences set forth in FIG. 1 or FIG. 2. Each CDR in a subject antibody may also be independently selected from any CDR shown in FIG. 1 or FIG. 2.

Examples of antibodies of the present disclosure are presented in Table 1 below. Although classified as a binder for a serotype, each antibody may be cross-reactive with more than one subtype/serotype, as described above. Details of cross-reactive antibodies can be found in Tables 1-5, 7-9.

TABLE 1

List of antibody clone names

| Type | Original organism | antibody clone name |
|---|---|---|
| BoNT/C, BoNT/CD, BoNT/DC or BoNT/D binders (11 clones): | human | 4C10 |
| | human | 4C10.1 |
| | human | 4C10.2 |
| | human | 4C10.5 |
| | human | 4C10.8 |
| | human | 4C10.15 |
| | human | 4C10.17 |
| | human | 4C10.18 |
| | human | 4C10.19 |
| | human | 4C10.20 |
| | human | 4C10.22 |

II. Potency of Botulinum Neurotoxin (BoNT)—Binding Antibodies

Without being bound to a particular theory, it is believed that the current antitoxins used to treat botulism (horse and human) have a potency of about 5000 mouse $LD_{50}s/mg$ (human) and 55,000 mouse $LD_{50}s/mg$ (horse).

Based on calculation, a commercially desirable antitoxin may generally have a potency greater than about 10,000 to 100,000 $LD_{50}s/mg$. Combinations of the antibodies described herein (e.g., two antibodies, or three antibodies) can meet this potency. Thus, this disclosure provides a combination of antibodies (e.g., two or three antibodies) that specifically bind to BoNT, and in some embodiments neutralize BoNT, at a potency of at least about 10,000 mouse $LD_{50}s/mg$ of antibody, at least about 15,000 mouse $LD_{50}s/mg$ of antibody, or at least about 20,000 mouse $LD_{50}s/mg$ of antibody, at least about 25,000 mouse $LD_{50}s/mg$ of antibody.

III. Preparation of Anti-BoNT Antibodies

Recombinant Expression of Anti-BoNT Antibodies

Using the information provided herein, the botulinum neurotoxin binding antibodies of the present disclosure are prepared using standard techniques well known to those of skill in the art.

For example, the polypeptide sequences provided herein (see, e.g., FIG. 3, FIG. 4, and/or Tables 7-8) can be used to determine appropriate nucleic acid sequences encoding the anti-BoNT antibodies and the nucleic acids sequences then used to express one or more BoNT-neutralizing antibodies. The nucleic acid sequence(s) can be optimized to reflect particular codon "preferences" for various expression systems according to standard methods well known to those of skill in the art.

Using the sequence information provided, the nucleic acids may be synthesized according to a number of standard methods known to those of skill in the art. Oligonucleotide synthesis can be carried out on commercially available solid phase oligonucleotide synthesis machines (Needham-VanDevanter et al. (1984) *Nucleic Acids Res.* 12:6159-6168) or manually synthesized using, for example, the solid phase phosphoramidite triester method described by Beaucage et al. (1981) *Tetrahedron Letts.* 22(20): 1859-1862.

Once a nucleic acid encoding an anti-BoNT antibody is synthesized it can be amplified and/or cloned according to standard methods. Molecular cloning techniques to achieve these ends are known in the art. A wide variety of cloning and in vitro amplification methods suitable for the construction of recombinant nucleic acids are known to persons of skill. Examples of these techniques and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning-A Laboratory Manual* (2nd ed.) Vol. 1-3, Cold Spring Harbor Laboratory, Cold Spring Harbor Press, N.Y., (Sambrook); and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). Methods of producing recombinant immunoglobulins are also known in the art. See, Cabilly, U.S. Pat. No. 4,816,567; and Queen et al. (1989) *Proc. Nat'l Acad. Sci. USA* 86: 10029-10033.

Examples of techniques sufficient to direct persons of skill through in vitro amplification methods, including the polymerase chain reaction (PCR), the ligase chain reaction (LCR), Qβ-replicase amplification and other RNA polymerase mediated techniques are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36-47; *The Journal Of NIH Research* (1991) 3, 81-94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077-1080; Van Brunt (1990) *Biotechnology* 8, 291-294; Wu and Wallace, (1989) *Gene* 4, 560; and Barringer et al. (1990) *Gene* 89, 117. Improved methods of cloning in vitro amplified nucleic acids are described in Wallace et al., U.S. Pat. No. 5,426,039.

Once the nucleic acid for an anti-BoNT antibody is isolated and cloned, one can express the gene in a variety of recombinantly engineered cells known to those of skill in the art. Examples of such cells include bacteria, yeast, filamentous fungi, insect (especially employing baculoviral vectors), plant, and mammalian cells. It is expected that those of skill in the art are knowledgeable in the numerous expression systems available for expression of antibodies.

In brief summary, the expression of natural or synthetic nucleic acids encoding anti-BoNT antibodies will typically be achieved by operably linking a nucleic acid encoding the antibody to a promoter (which is either constitutive or inducible), and incorporating the construct into an expression vector. The vectors can be suitable for replication and integration in prokaryotes, eukaryotes, or both. Typical cloning vectors contain transcription and translation terminators, initiation sequences, and promoters useful for regulation of the expression of the nucleic acid encoding the anti-BoNT antibody. The vectors optionally comprise generic expression cassettes containing at least one independent terminator sequence, sequences permitting replication of the cassette in both eukaryotes and prokaryotes, i.e., shuttle vectors, and selection markers for both prokaryotic and eukaryotic systems. See Sambrook et al (1989) supra.

To obtain high levels of expression of a cloned nucleic acid it is common to construct expression plasmids which typically contain a strong promoter to direct transcription, a ribosome binding site for translational initiation, and a transcription/translation terminator. Examples of regulatory regions suitable for this purpose in *E. coli* are the promoter and operator region of the *E. coli* tryptophan biosynthetic pathway as described by Yanofsky (1984) *J. Bacteriol.*, 158:1018-1024, and the leftward promoter of phage lambda ($P_L$) as described by Herskowitz and Hagen (1980) *Ann. Rev. Genet.*, 14:399-445 and the L-arabinose (araBAD) operon (Better (1999) *Gene Exp Systems* pp 95-107 Academic Press, Inc., San Diego, Calif.). The inclusion of selection markers in DNA vectors transformed in *E. coli* is also useful. Examples of such markers include genes specifying resistance to ampicillin, tetracycline, or chloramphenicol. See Sambrook et al (1989) supra for details concerning selection markers, e.g., for use in *E. coli*.

Expression systems for expressing anti-BoNT antibodies are available using, for example, *E. coli*, *Bacillus* sp. (see, e.g., Palva, et al. (1983) Gene 22:229-235; Mosbach et al. (1983) *Nature,* 302: 543-545), and Salmonella. *E. coli* systems may also be used.

The anti-BoNT antibodies produced by prokaryotic cells may require exposure to chaotropic agents for proper folding. During purification from, e.g., *E. coli*, the expressed protein is optionally denatured and then renatured. This can be accomplished, e.g., by solubilizing the bacterially produced antibodies in a chaotropic agent such as guanidine HCl. The antibody is then renatured, either by slow dialysis or by gel filtration (see, e.g., U.S. Pat. No. 4,511,503). Alternatively, nucleic acid encoding the anti-BoNT antibodies may be operably linked to a secretion signal sequence such as pelB so that the anti-BoNT antibodies are secreted into the medium in correctly-folded form (Better et al (1988) *Science* 240: 1041-1043).

Methods of transfecting and expressing genes in mammalian cells are known in the art (see e.g. Birch and Racher *Adv. Drug Deliv. Rev.* 2006, 58: 671-685). Transducing cells with nucleic acids can involve, for example, incubating viral vectors containing anti-BoNT nucleic acids with cells within the host range of the vector (see, e.g., Goeddel (1990) *Methods in Enzymology*, vol. 185, Academic Press, Inc., San Diego, Calif. or Krieger (1990) *Gene Transfer and Expression-A Laboratory Manual*, Stockton Press, New York, N.Y. and the references cited therein).

The culture of cells used in the present disclosure, including cell lines and cultured cells from tissue or blood samples is well known in the art (see, e.g., Freshney (1994) *Culture of Animal Cells, a Manual of Basic Technique, third edition*, Wiley-Liss, N.Y. and the references cited therein).

Techniques for using and manipulating antibodies are found in Coligan (1991) *Current Protocols in Immunology* Wiley/Greene, N.Y.; Harlow and Lane (1989) *Antibodies: A Laboratory Manual* Cold Spring Harbor Press, NY; Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) *Nature* 256: 495-497.

The anti-BoNT antibody gene(s) (e.g. anti-BoNT scFv gene) may be subcloned into the expression vector pUC119mycHis (Tomlinson et al. (1996) *J. Mol. Biol.,* 256: 813-817) or pSYN3, resulting in the addition of a hexahistidine tag at the C-terminal end of the scFv to facilitate purification. Detailed protocols for the cloning and purification of certain anti-BoNT antibodies are found, for example, in Amersdorfer et al. (1997) *Infect. Immunity,* 65(9): 3743-3752, and the like.

Preparation of Whole Polyclonal or Monoclonal Antibodies

The anti-BoNT antibodies of the present disclosure include individual, allelic, strain, or species variants, and fragments thereof, both in their naturally occurring (full-length) forms and in recombinant forms. Certain antibodies may be selected to bind one or more epitopes bound by the antibodies described herein (as seen in FIG. 1 or FIG. 2). The antibodies can be raised in their native configurations or in non-native configurations. Anti-idiotypic antibodies can also be generated. Many methods of making antibodies that specifically bind to a particular epitope are known to persons of skill. The following discussion is presented as a general overview of the techniques available; however, one of skill will recognize that many variations upon the following methods are known.

Polyclonal Antibody Production

Methods of producing polyclonal antibodies are known to those of skill in the art. In brief, an immunogen (e.g., BoNT/C, BoNT/D, BoNT/DC, etc.), subsequences including, but not limited to subsequences comprising epitopes specifically bound by antibodies expressed by clones disclosed herein, e.g., a purified polypeptide, a polypeptide coupled to an appropriate carrier (e.g., GST, keyhole limpet hemanocyanin, etc.), or a polypeptide incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the polypeptide of interest. When appropriately high titers of antibody to the immunogen are obtained, blood is collected from the animal and antisera are prepared. Further fractionation of the antisera to enrich for antibodies reactive to the BoNT polypeptide is performed where desired (see, e.g., Coligan (1991) *Current Protocols in Immunology* Wiley/Greene, N.Y.; and Harlow and Lane (1989) *Antibodies: A Laboratory Manual* Cold Spring Harbor Press, NY).

Antibodies that specifically bind to the epitopes described herein can be selected from polyclonal sera using the selection techniques described herein.

Monoclonal Antibody Production

In some instances, it is desirable to prepare monoclonal antibodies from various mammalian hosts, such as mice, rodents, primates, humans, etc. Descriptions of techniques for preparing such monoclonal antibodies are found in, e.g., Stites et al. (eds.) *Basic and Clinical Immunology* (4th ed.) Lange Medical Publications, Los Altos, Calif., and references cited therein; Harlow and Lane, supra; Goding (1986) *Monoclonal Antibodies: Principles and Practice* (2d ed.) Academic Press, New York, N.Y.; and Kohler and Milstein (1975) *Nature* 256: 495-497.

Summarized briefly, monoclonal antibody production using hybridomas may proceed by injecting an animal with an immunogen (e.g., BoNT/C, BoNT/D, BoNT/DC, etc.) subsequences including, but not limited to subsequences comprising epitopes specifically bound by antibodies expressed by clones disclosed herein. The animal is then sacrificed and cells taken from its spleen, which are fused with myeloma cells. The result is a hybrid cell or "hybridoma" that is capable of reproducing antibodies in vitro. The population of hybridomas is then screened to isolate individual clones, each of which secretes a single antibody species to the immunogen. In this manner, the individual antibody species obtained are the products of immortalized and cloned single B cells from the immune animal generated in response to a specific site recognized on the immunogenic substance.

Alternative methods of immortalization include transformation with Epstein Barr Virus, oncogenes, or retroviruses, or other methods known in the art. Colonies arising from single immortalized cells are screened for production of antibodies of the desired specificity and affinity for the BoNT antigen, and yield of the monoclonal antibodies produced by such cells is enhanced by various techniques, including injection into the peritoneal cavity of a vertebrate (e.g., mammalian) host. The antibodies of the present disclosure are used with or without modification, and include chimeric antibodies such as humanized murine antibodies.

Techniques for creating recombinant DNA versions of the antigen-binding regions of antibody molecules which bypass the generation of hybridomas are contemplated for the present BoNT binding antibodies and fragments. DNA is cloned into a bacterial expression system. One example of a suitable technique uses a bacteriophage lambda vector system having a leader sequence that causes the expressed Fab protein to migrate to the periplasmic space (between the bacterial cell membrane and the cell wall) or to be secreted. One can rapidly generate and screen great numbers of functional Fab fragments for those which bind BoNT. Such BoNT binding agents (Fab fragments with specificity for a BoNT polypeptide) are specifically encompassed within the BoNT binding antibodies and fragments of the present disclosure. Other methods for screening and production of antibodies may employ one or more of display systems such as phage display, yeast display, ribosome, etc., and an antibody production system such as that derived from transgenic mice.

The present disclosure provides an isolated nucleic acid comprising a nucleotide sequence encoding an antibody of the present disclosure. The present disclosure provides an isolated nucleic acid comprising a nucleotide sequence encoding an amino acid sequence of a $V_H$ of a subject antibody. The present disclosure provides an isolated nucleic acid comprising a nucleotide sequence encoding an amino acid sequence of a $V_L$ of a subject antibody. The present disclosure provides an isolated nucleic acid comprising a nucleotide sequence encoding an amino acid sequence of a $V_H$ and a $V_L$ of a subject antibody. In some instances, a subject nucleic acid comprises a nucleotide sequence encoding $V_H$ CDR1, CDR2, and CDR3 of a subject antibody and/or a $V_L$ CDR1, CDR2, and CDR3 of a subject antibody.

In some cases, the isolated nucleic acid comprises the nucleotide sequence encoding an amino acid sequence of: a) a $V_H$ of an antibody comprising a CDR1, CDR2 and CDR3, wherein the CDR1, CDR2, and CDR3 are selected from the $V_H$ of the antibody 4C10.20; and b) a $V_L$ of an antibody comprising a CDR1, CDR2 and CDR3, wherein the CDR1, CDR2, and CDR3 are selected from the $V_L$ of the antibody 4C10.20.

The present disclosure provides an isolated nucleic acid comprising a nucleotide sequence encoding an amino acid sequence of a variable heavy chain ($V_H$) polypeptide comprising a $V_H$ CDR1 selected from a $V_H$ of the antibody 4C10.20, a $V_H$ CDR2 comprising a $V_H$ CDR2 selected from a $V_H$ of the antibody 4C10.20, and a $V_H$ CDR2 selected from a $V_H$ of the antibody 4C10.20. In such cases, a variable heavy chain ($V_H$) polypeptide is encoded by the nucleic acid.

The present disclosure provides an isolated nucleic acid comprising a nucleotide sequence encoding an amino acid sequence of a variable light chain ($V_L$) polypeptide comprising a $V_L$ CDR1 selected from a $V_L$ of the antibody 4C10.20, a $V_L$ CDR2 comprising a $V_L$ CDR2 selected from a $V_L$ of the antibody 4C10.20, and a $V_L$ CDR2 selected from a $V_L$ of the antibody 4C10.20. In such cases, the variable light chain ($V_L$) polypeptide is encoded by the nucleic acid.

The nucleic acid can be a recombinant vector, as described above, which provides for amplification and/or expression (synthesis) of the encoded antibody. The recombinant vector can be suitable for expression in prokaryotic and/or eukaryotic cells.

The present disclosure also provides a cell, e.g., a genetically modified cell, that comprises a subject nucleic acid. A subject genetically modified cell can be a prokaryotic cell (e.g., a bacterial cell); or a eukaryotic cell (e.g., an insect cell; a mammalian cell, such as a mammalian cell line suitable for in vitro cell culture; a yeast cell; etc.), where the cell may produce the encoded antibody.

IV. Modification of Anti-BoNT Antibodies

Creation of Anti-BoNT (scFv')$_2$ Homodimers

To create anti-BoNT (scFv')$_2$ antibodies, two anti-BoNT scFvs are joined, either through a linker (e.g., a carbon linker, a peptide, etc.) or through a disulfide bond between, for example, two cysteines. Thus, for example, to create disulfide linked scFv, a cysteine residue can be introduced by site directed mutagenesis between a myc tag and a hexahistidine tag at the carboxy-terminus of an anti-BoNT/B. Introduction of the correct sequence can be verified by DNA sequencing. The construct may be in pUC119, so that the pelB leader directs expressed scFv to the periplasm and cloning sites (NcoI and NotI) exist to introduce anti-BoNT mutant scFv. Expressed scFv has the myc tag at the C-terminus, followed by two glycines, a cysteine, and then 6 histidines to facilitate purification by IMAC. After disulfide bond formation between the two cysteine residues, the two scFv can be separated from each other by 26 amino acids (two 11 amino acid myc tags and three repeats of a unit with 4 glycines plus one serine). An scFv expressed from this construct, purified by IMAC may predominantly comprise monomeric scFv. To produce (scFv')$_2$ dimers, the cysteine can be reduced by incubation with 1 mM beta-mercaptoethanol, and half of the scFv blocked by the addition of DTNB. Blocked and unblocked scFvs can be incubated together to form (scFv')$_2$ and the resulting material can optionally be analyzed by gel filtration. The affinity of the anti-BoNT scFv' monomer and (scFv')$_2$ dimer can optionally be determined by BIAcore.

The (scFv')$_2$ dimer may be created by joining the scFv fragments through a linker, e.g., through a peptide linker. This can be accomplished by a wide variety of means well known to those of skill in the art. For example, one suitable approach is described by Holliger et al. (1993) *Proc. Natl. Acad. Sci. USA*, 90: 6444-6448 (see also WO 94/13804).

Typically, linkers are introduced by PCR cloning. For example, synthetic oligonucleotides encoding the 5 amino acid linker (Gly$_4$Ser, SEQ ID NO: 45) can be used to PCR amplify the anti-BoNT antibody $V_H$ and $V_L$ genes which are then spliced together to create the anti-BoNT diabody gene. The gene can then be cloned into an appropriate vector, expressed, and purified according to standard methods well known to those of skill in the art.

Preparation of Anti-BoNT (scFv)$_2$, Fab, and (Fab')$_2$ Molecules

Anti-BoNT antibodies such as anti-BoNT/C or anti-BoNT/D scFv, or variant(s) with higher affinity, are suitable templates for creating size and valency variants. For example, an anti-BoNT (scFv')$_2$ can be created from the parent scFv as described above. An scFv gene can be excised using appropriate restriction enzymes and cloned into another vector as described herein.

Expressed scFv may include a myc tag at the C-terminus, followed by two glycines, a cysteine, and six histidines to facilitate purification. After disulfide bond formation between the two cystine residues, the two scFv may be separated from each other by 26 amino acids (e.g., two eleven amino acid myc tags and four glycines). Single-chain Fv (scFv) can be expressed from this construct and purified.

To produce (scFv')$_2$ dimers, the cysteine is reduced by incubation with 1 mM β-mercaptoethanol, and half of the scFv blocked by the addition of DTNB. Blocked and unblocked scFv are incubated together to form (scFv')$_2$, which is purified. As higher affinity scFv are isolated, their genes are similarly used to construct (scFv')$_2$.

Anti-BoNT Fab may also be expressed in *E. coli* using an expression vector similar to the one described by Better et al. (1988) *Science*, 240: 1041-1043. For example, to create a BoNT/C or BoNT/D binding Fab, the V$_H$ and V$_L$ genes are amplified from the scFv using PCR. The V$_H$ gene is cloned into an expression vector (e.g., a pUC119 based bacterial expression vector) that provides an IgG C$_H$1 domain downstream from, and in frame with, the V$_H$ gene. The vector also contains the lac promoter, a pelB leader sequence to direct expressed V$_H$-C$_H$1 domain into the periplasm, a gene 3 leader sequence to direct expressed light chain into the periplasm, and cloning sites for the light chain gene. Clones containing the correct V$_H$ gene are identified, e.g., by PCR fingerprinting. The V$_L$ gene is spliced to the C$_L$ gene using PCR and cloned into the vector containing the V$_H$C$_H$1 gene.

Selection of Antibodies

Selection of anti-BoNT antibodies (whether produced by phage display, yeast display, immunization methods, hybridoma technology, etc.) can involve screening the resulting antibodies for specific binding to an appropriate antigen(s). In the instant case, suitable antigens can include, but are not limited to BoNT/C, BoNT/D, BoNT/DC, BoNT/CD, a C-terminal domain of BoNT heavy chain (binding domain) of BoNT holotoxins, recombinant BoNT domains such as H$_C$ (binding domain), H$_N$ (translocation domain), or L$_C$ (light chain), and the like. The antibodies may be selected for specific binding of an epitope recognized by one or more of the antibodies described herein.

Selection can be by any of a number of methods well known to those of skill in the art. In one example, selection is by immunochromatography (e.g., using immunotubes, Maxisorp, Nunc) against the desired target, e.g., BoNT/C, BoNT/D, etc. . . . In a related example, selection is against a BoNT protein in a surface plasmon resonance system (e.g., BIAcore, Pharmacia) either alone or in combination with an antibody that binds to an epitope specifically bound by one or more of the antibodies described herein. Selection can also be done using flow cytometry for yeast display libraries. Yeast display libraries are sequentially selected to obtain antibodies that bind with high affinity to all subtypes of BoNT/C. This can be repeated for other subtypes.

For phage display, analysis of binding can be simplified by including an amber codon between the antibody fragment gene and gene III. This makes it possible to easily switch between displayed and soluble antibody fragments simply by changing the host bacterial strain. When phage are grown in a supE suppresser strain of *E. coli*, the amber stop codon between the antibody gene and gene III is read as glutamine and the antibody fragment is displayed on the surface of the phage. When eluted phage are used to infect a non-suppressor strain, the amber codon is read as a stop codon and soluble antibody is secreted from the bacteria into the periplasm and culture media (Hoogenboom et al. (1991) *Nucleic Acids Res.*, 19: 4133-4137). Binding of soluble scFv to antigen can be detected, e.g., by ELISA using a murine IgG monoclonal antibody (e.g., 9E10) which recognizes a C-terminal myc peptide tag on the scFv (Evan et al. (1985) *Mol. Cell Biol.*, 5: 3610-3616; Munro et al. (1986) *Cell*, 46: 291-300), e.g., followed by incubation with polyclonal anti-mouse Fc conjugated to a detectable label (e.g., horseradish peroxidase).

As indicated above, purification of the anti-BoNT antibody can be facilitated by cloning of the scFv gene into an expression vector (e.g., expression vector pUC119mycHIS) that results in the addition of the myc peptide tag followed by a hexa-histidine tag at the C-terminal end of the scFv. The vector may also encode a pectate lyase leader sequence that directs expression of the scFv into the bacterial periplasm where the leader sequence is cleaved. This makes it possible to harvest native properly folded scFv directly from the bacterial periplasm. The anti-BoNT antibody is then expressed and purified from the bacterial supernatant using immobilized metal affinity chromatography.

Measurement of Anti-BoNT Antibody Affinity for One or More BoNT Subtypes

As explained above, selection for increased avidity involves measuring the affinity of an anti-BoNT antibody (e.g. a modified anti-BoNT antibody) for one or more targets of interest (e.g. BoNT subtype(s) or domains thereof. For example, the K$_D$ of a BoNT/C-binding antibody and the kinetics of binding to BoNT/C are determined in a BIAcore, a biosensor based on surface plasmon resonance. For this technique, antigen is coupled to a derivatized sensor chip capable of detecting changes in mass. When antibody is passed over the sensor chip, antibody binds to the antigen resulting in an increase in mass that is quantifiable.

Measurement of the rate of association as a function of antibody concentration can be used to calculate the association rate constant (k$_{on}$). After the association phase, buffer is passed over the chip and the rate of dissociation of antibody (k$_{off}$) determined. K$_{on}$ is typically measured in the range $1.0 \times 10^2$ to $5.0 \times 10^6$ M and k$_{off}$ in the range $1.0 \times 10^{-1}$ to $1.0 \times 10^{-6}$ M. The equilibrium constant K$_d$ is then calculated as k$_{off}$/k$_{on}$ and thus is typically measured in the range $10^{-5}$ to $10^{-12}$ M. Affinities measured in this manner usually correlate well with affinities measured in solution by fluorescence quench titration. Since increased affinity normally results primarily from a reduction in the k$_{off}$, measurement of k$_{off}$ should identify higher affinity scFv. k$_{off}$ can be measured in the BIAcore on unpurified scFv in bacterial periplasm, since expression levels are high enough to give an adequate binding signal and k$_{off}$ is independent of concentration. The value of k$_{off}$ for periplasmic and purified scFv is typically in close agreement.

V. Humanized, Human Engineered or Human Antibody Production

The present BoNT binding antibodies and fragments can be humanized or human engineered antibodies. As used herein, a humanized antibody, or antigen binding fragment thereof, is a recombinant polypeptide that comprises a portion of an antigen binding site from a non-human antibody and a portion of the framework and/or constant regions of a human antibody. A human engineered antibody or antibody fragment may be derived from a human or non-human (e.g., mouse) source that has been engineered by modifying (e.g., deleting, inserting, or substituting) amino acids at specific positions so as to alter certain biophysical properties or to reduce any detectable immunogenicity of the modified antibody in a human.

Humanized antibodies also encompass chimeric antibodies and CDR-grafted antibodies in which various regions may be derived from different species. Chimeric antibodies may be antibodies that include a non-human antibody variable region linked to a human constant region. Thus, in chimeric antibodies, the variable region is mostly non-human, and the constant region is human. Chimeric antibodies and methods for making them are described in Morrison, et al., *Proc. Natl. Acad. Sci.* USA, 81: 6841-6855 (1984), Boulianne, et al., *Nature*, 312: 643-646 (1984), and PCT Application Publication WO 86/01533. Although, they can be less immunogenic than a mouse monoclonal antibody, administrations of chimeric antibodies have been associated with human anti-mouse antibody responses (HAMA) to the non-human portion of the antibodies. Chimeric antibodies can also be produced by splicing the genes from a mouse antibody molecule of appropriate antigen-binding specificity together with genes from a human antibody molecule of appropriate biological activity, such as the ability to activate human complement and mediate ADCC. Morrison et al. (1984), *Proc. Natl. Acad. Sci.*, 81: 6851; Neuberger et al. (1984), *Nature*, 312: 604. One example is the replacement of an Fc region with that of a different isotype.

CDR-grafted antibodies are antibodies that include the CDRs from a non-human "donor" antibody linked to the framework region from a human "recipient" antibody. Generally, CDR-grafted antibodies include more human antibody sequences than chimeric antibodies because they include both constant region sequences and variable region (framework) sequences from human antibodies. Thus, for example, a CDR-grafted humanized antibody may comprise a heavy chain that comprises a contiguous amino acid sequence (e.g., about 5 or more, 10 or more, or even 15 or more contiguous amino acid residues) from the framework region of a human antibody (e.g., FR-1, FR-2, or FR-3 of a human antibody) or, optionally, most or all of the entire framework region of a human antibody. CDR-grafted antibodies and methods for making them are described in, Jones et al., *Nature*, 321: 522-525 (1986), Riechmann et al., *Nature*, 332: 323-327 (1988), and Verhoeyen et al., *Science*, 239: 1534-1536 (1988)). Methods that can be used to produce humanized antibodies also are described in U.S. Pat. Nos. 4,816,567, 5,721,367, 5,837,243, and 6,180,377. CDR-grafted antibodies are considered less likely than chimeric antibodies to induce an immune reaction against non-human antibody portions. However, it has been reported that framework sequences from the donor antibodies are required for the binding affinity and/or specificity of the donor antibody, presumably because these framework sequences affect the folding of the antigen-binding portion of the donor antibody. Therefore, when donor, non-human CDR sequences are grafted onto unaltered human framework sequences, the resulting CDR-grafted antibody can exhibit, in some cases, loss of binding avidity relative to the original non-human donor antibody. See, e.g., Riechmann et al., *Nature*, 332: 323-327 (1988), and Verhoeyen et al., *Science*, 239: 1534-1536 (1988).

Human engineered antibodies include for example "veneered" antibodies and antibodies prepared using HUMAN ENGINEERING™ technology (U.S. Pat. No. 5,869,619). HUMAN ENGINEERING™ technology is commercially available, and involves altering an non-human antibody or antibody fragment, such as a mouse or chimeric antibody or antibody fragment, by making specific changes to the amino acid sequence of the antibody so as to produce a modified antibody with reduced immunogenicity in a human that nonetheless retains the desirable binding properties of the original non-human antibodies. Techniques for making human engineered proteins are described in Studnicka et al., *Protein Engineering*, 7: 805-814 (1994), U.S. Pat. Nos. 5,766,886, 5,770,196, 5,821,123, and 5,869,619, and PCT Application Publication WO 93/11794.

"Veneered" antibodies are non-human or humanized (e.g., chimeric or CDR-grafted antibodies) antibodies that have been engineered to replace certain solvent-exposed amino acid residues so as to further reduce their immunogenicity or enhance their function. As surface residues of a chimeric antibody are presumed to be less likely to affect proper antibody folding and more likely to elicit an immune reaction, veneering of a chimeric antibody can include, for instance, identifying solvent-exposed residues in the non-human framework region of a chimeric antibody and replacing at least one of them with the corresponding surface residues from a human framework region. Veneering can be accomplished by any suitable engineering technique, including the use of the above-described HUMAN ENGINEERING™ technology.

In a different approach, a recovery of binding avidity can be achieved by "de-humanizing" a CDR-grafted antibody. De-humanizing can include restoring residues from the donor antibody's framework regions to the CDR grafted antibody, thereby restoring proper folding. Similar "de-humanization" can be achieved by (i) including portions of the "donor" framework region in the "recipient" antibody or (ii) grafting portions of the "donor" antibody framework region into the recipient antibody (along with the grafted donor CDRs).

For a further discussion of antibodies, humanized antibodies, human engineered, and methods for their preparation, see Kontermann and Dubel, eds., *Antibody Engineering*, Springer, New York, N.Y., 2001.

The present antibodies and fragments encompass antibodies having CDRs of human origin, such as antibodies which bind BoNT polypeptides and are encoded by nucleic acid sequences which are naturally occurring somatic variants of human germline immunoglobulin nucleic acid sequence, and fragments, synthetic variants, derivatives and fusions thereof. Such antibodies may be produced by any method known in the art, such as through the use of transgenic mammals (such as transgenic mice) in which the native immunoglobulin repertoire has been replaced with human V-genes in the mammal chromosome. Such mammals appear to carry out VDJ recombination and somatic hypermutation of the human germline antibody genes in a normal fashion, thus producing high affinity antibodies with completely human sequences.

Human antibodies can also be generated through the in vitro screening of antibody display libraries. See Hoogenboom et al. (1991), *J. Mol. Biol.* 227: 381; and Marks et al. (1991), *J. Mol. Biol.* 222: 581. Various antibody-containing phage display libraries have been described and may be readily prepared. Libraries may contain a diversity of human antibody sequences, such as human Fab, Fv, and scFv fragments that may be screened against an appropriate target. Phage display libraries may comprise peptides or proteins other than antibodies which may be screened to identify selective binding agents of BoNT.

The development of technologies for making repertoires of recombinant human antibody genes, and the display of the encoded antibody fragments on the surface of filamentous bacteriophage, has provided a means for making human antibodies directly. The antibodies produced by phage technology are produced as antigen binding fragments-usually Fv or Fab fragments-in bacteria and thus lack effector functions. Effector functions can be introduced by one of two strategies: The fragments can be engineered either into complete antibodies for expression in mammalian cells, or into bispecific antibody fragments with a second binding site capable of triggering an effector function.

Methods for display of peptides on the surface of yeast and microbial cells have also been used to identify antigen specific antibodies. See, for example, U.S. Pat. No. 6,699,658. Antibody libraries may be attached to yeast proteins, such as agglutinin, effectively mimicking the cell surface display of antibodies by B cells in the immune system.

In addition to phage display methods, antibodies may be isolated using ribosome mRNA display methods and microbial cell display methods. Selection of polypeptide using ribosome display is described in Hanes et al., (*Proc. Natl. Acad. Sci.* USA, 94:4937-4942, 1997) and U.S. Pat. Nos. 5,643,768 and 5,658,754 issued to Kawasaki. Ribosome display is also useful for rapid large scale mutational analysis of antibodies. The selective mutagenesis approach also provides a method of producing antibodies with improved activities that can be selected using ribosomal display techniques.

VI. Other Antibody Forms

Sequence provided herein can be used to generate other antibody forms, including but not limited to nanobodies, UniBodies, and/or affibodies.

VHH and/or Nanobodies

The Camelidae heavy chain antibodies are found as homodimers of a single heavy chain, dimerized via their constant regions. The variable domains of these camelidae heavy chain antibodies are referred to as VHH domains or VHH, and can be either used per se as nanobodies and/or as a starting point for obtaining nanobodies. Isolated VHH retain the ability to bind antigen with high specificity (see, e.g., Hamers-Casterman et al. (1993) *Nature* 363: 446-448). VHH domains, or nucleotide sequences encoding them, can be derived from antibodies raised in Camelidae species, for example in camel, dromedary, llama, alpaca and guanaco. Other species besides Camelidae (e.g., shark, pufferfish) can produce functional antigen-binding heavy chain antibodies, from which (nucleotide sequences encoding) such naturally occurring VHH can be obtained, e.g. using the methods described in U.S. Patent Publication US 2006/0211088.

Human proteins may be used in therapy primarily because they are not as likely to provoke an immune response when administered to a patient. Comparisons of camelid VHH with the $V_H$ domains of human antibodies reveals several key differences in the framework regions of the camelid VHH domain corresponding to the $V_H/V_L$ interface of the human $V_H$ domains. Mutation of these human residues to VHH resembling residues has been performed to produce "camelized" human $V_H$ domains that retain antigen binding activity, yet have improved expression and solubility.

Libraries of single $V_H$ domains have also been derived for example from $V_H$ genes amplified from genomic DNA or from mRNA came from the spleens of immunized mice and expressed in *E. coli* (Ward et al. (1989) *Nature* 341: 544-546) and similar approaches can be performed using the $V_H$ domains and/or the $V_L$ domains described herein. The isolated single $V_H$ domains are called "dAbs" or domain antibodies. A "dAb" is an antibody single variable domain ($V_H$ or $V_L$) polypeptide that specifically binds antigen. A "dAb" binds antigen independently of other V domains; however, as the term is used herein, a "dAb" can be present in a homo- or heteromultimer with other $V_H$ or $V_L$ domains where the other domains are not required for antigen binding by the dAb, i.e., where the dAb binds antigen independently of the additional $V_H$ or $V_L$ domains.

As described in U.S. Patent Publication No. 2006/0211088 methods are known for the cloning and direct screening of immunoglobulin sequences (including but not limited to multivalent polypeptides comprising: two or more variable domains—or antigen binding domains—and in particular $V_H$ domains or VHH domains; fragments of $V_L$, $V_H$ or VHH domains, such as CDR regions, for example CDR3 regions; antigen-binding fragments of conventional 4-chain antibodies such as Fab fragments and scFv's, heavy chain antibodies and domain antibodies; and in particular of VH sequences, and more in particular of VHH sequences) that can be used as part of and/or to construct such nanobodies.

Methods and procedures for the production of VHH/nanobodies can also be found for example in WO 94/04678, WO 96/34103, WO 97/49805, WO 97/49805 WO 94/25591, WO 00/43507 WO 01/90190, WO 03/025020, WO 04/062551, WO 04/041863, WO 04/041865, WO 04/041862, WO 04/041867, PCT/BE2004/000159, Hamers-Casterman et al. (1993) *Nature* 363: 446; Riechmann and Muyldermans (1999) *J. Immunological Meth.*, 231: 25-38; Vu et al. (1997) *Molecular Immunology*, 34(16-17): 1121-1131; Nguyen et al. (2000) EMBO J., 19(5): 921-930; Arbabi Ghahroudi et al. (19997) *FEBS Letters* 414: 521-526; van der Linden et al. (2000) *J. Immunological Meth.*, 240: 185-195; Muyldermans (2001) *Rev. Molecular Biotechnology* 74: 277-302; Nguyen el al. (2001) *Adv. Immunol.* 79:261, and the like, which are all incorporated herein by reference.

UniBodies

UniBodies are generated by an antibody technology that produces a stable, smaller antibody format with an anticipated longer therapeutic window than certain small antibody formats. UniBodies may be produced from IgG4 antibodies by eliminating the hinge region of the antibody. Unlike the full size IgG4 antibody, the half molecule fragment is very stable and is termed a UniBody. Halving the IgG4 molecule left only one area on the UniBody that can bind to a target. Methods of producing UniBodies are described in detail in PCT Publication WO2007/059782, which is incorporated herein by reference in its entirety (see, also, Kolfschoten et al. (2007) *Science* 317: 1554-1557).

Affibodies

Affibody molecules are class of affinity proteins based on a 58-amino acid residue protein domain, derived from one of the IgG-binding domains of staphylococcal protein A. This three helix bundle domain has been used as a scaffold for the construction of combinatorial phagemid libraries, from which affibody variants that target the desired molecules can be selected using phage display technology (see, e.g., Nord et al. (1997) *Nat. Biotechnol.* 15: 772-777; Ronmark et al. (2002) *Eur. J. Biochem.*, 269: 2647-2655.). Details of affibodies and methods of production are known to those of skill (see, e.g., U.S. Pat. No. 5,831,012 which is incorporated herein by reference in its entirety).

VII. Assaying for Cross-Reactivity at an Epitope

The antibodies of the present disclosure encompass those that specifically bind to one or more epitopes recognized by antibodies described herein (as seen in FIG. 1 and FIG. 2). In other words, antibodies are cross-reactive with one or more of these epitopes but may have different sequences. Means of assaying for cross-reactivity are well known to those of skill in the art (see, e.g., Dowbenko et al. (1988) *J. Virol.* 62: 4703-4711).

This can be ascertained by providing one or more isolated target BoNT polypeptide(s) (e.g. BoNT/C and/or BoNT/D, or recombinant domains of said toxin, such as $H_C$) attached to a solid support and assaying the ability of a test antibody to compete with, an antibody described herein for binding to the target BoNT peptide. Thus, immunoassays in a competitive binding format can be used for cross-reactivity determinations. For example, a BoNT/C and/or BoNT/D polypeptide may be immobilized to a solid support. Antibodies to be tested (e.g. generated by selection from a phage-display library) added to the assay compete with any antibody from clones as shown in FIG. 1 and FIG. 2 for binding to the immobilized BoNT polypeptide(s). The ability of test antibodies to compete with the binding of one or more antibodies listed in FIG. 1 or FIG. 2 to the immobilized protein(s) are compared. The percent cross-reactivity above proteins is then calculated, using standard calculations.

If the test antibody competes with one or more of the antibodies listed in FIG. 1 or FIG. 2 and has a binding affinity comparable to or greater than a threshold (such as having a $K_D$ equal or less than about $1 \times 10^{-8}$ M) with the same target then the test antibody is expected to be an anti-BoNT antibody. In some cases, a subject antibody competes for binding to a Botulinum neurotoxin epitope with an antibody comprising VH and/or VL CDRs (e.g., $V_H$ CDR1, CDR2, and CDR3; and/or $V_L$ CDR1, CDR2, and CDR3) of an antibody depicted in FIG. 1 or FIG. 2. As one non-limiting example, in some instances, a subject antibody competes for binding to a Botulinum neurotoxin epitope with an antibody comprising VH CDR1, VH CDR2, and VH CDR3 of the antibody designated 4C10.20. In some instances, a subject antibody competes for binding to a Botulinum neurotoxin epitope with an antibody comprising VL CDR1, VL CDR2, and VL CDR3 of the antibody designated 4C10.20. As another example, in some cases, a subject antibody competes for binding to a Botulinum neurotoxin epitope with an antibody comprising VH CDR1, VH CDR2, VH CDR3, VL CDR1, VL CDR2, VL CDR3 of the antibody designated 4C10.20.

Cross-reactivity may be performed by using surface plasmon resonance in a BIAcore. In a BIAcore flow cell, the BoNT polypeptide(s) (e.g., BoNT/C and/or BoNT/D) are coupled to a sensor chip (e.g. CM5) as described in WO 09/008916, disclosure of which is incorporated herein by reference. With a flow rate of 5 µl/min, a titration of 100 nM to 1 µM antibody is injected over the flow cell surface for about 5 minutes to determine an antibody concentration that results in near saturation of the surface. Epitope mapping is then evaluated using pairs of antibodies at concentrations resulting in near saturation and at least 100 relative units (RU) of antibody bound. The amount of antibody bound is determined for each member of a pair, and then the two antibodies are mixed together to give a final concentration equal to the concentration used for measurements of the individual antibodies. Antibodies recognizing different epitopes show an essentially additive increase in the RU bound when injected together, while antibodies recognizing identical epitopes show only a minimal increase in RU. Antibodies may be said to be cross-reactive if, when "injected" together they show an essentially additive increase (e.g., an increase by at least a factor of about 1.4, an increase by at least a factor of about 1.6, or an increase by at least a factor of about 1.8 or 2).

Epitope mapping may also be determined by incubating a yeast displayed scFv with a BoNT domain polypeptide followed by incubation with an epitope-tagged scFv. Bound scFv is detected with an antibody recognizing the epitope tag and the level of BoNT domain display quantitated by incubation with anti-SV5.

Cross-reactivity at the desired epitopes can be ascertained by a number of other standard techniques (see, e.g., Geysen et al (1987) *J. Immunol. Meth.* 102, 259-274). This technique involves the synthesis of large numbers of overlapping BoNT peptides. The synthesized peptides are then screened against one or more of the prototypical antibodies (e.g., 4C10.1, 8DC1.2, etc.) and the characteristic epitopes specifically bound by these antibodies can be identified by binding specificity and affinity. The epitopes thus identified can be conveniently used for competitive assays as described herein to identify cross-reacting antibodies.

The peptides for epitope mapping can be conveniently prepared using "Multipin" peptide synthesis techniques (see, e.g., Geysen et al (1987) *Science,* 235: 1184-1190). Using the known sequence of one or more BoNT subtypes (see, e.g., Atassi et al. (1996) *J. Prot. Chem.,* 7: 691-700 and references cited therein), overlapping BoNT polypeptide sequences can be synthesized individually in a sequential manner on plastic pins in an array of one or more 96-well microtest plate(s).

The procedure for epitope mapping using this multipin peptide system is described in U.S. Pat. No. 5,739,306. Briefly, the pins are first treated with a pre-coat buffer containing 2% bovine serum albumin and 0.1% Tween 20 in phosphate-buffered saline (PBS) for 1 hour at room temperature. Then the pins are then inserted into the individual wells of 96-well microtest plate containing the antibodies in the pre-coat buffer, e.g. at 2 µg/ml. The incubation can be carried out for about 1 hour at room temperature. The pins are washed in PBST (e.g., 3 rinses for every 10 minutes), and then incubated in the wells of a 96-well microtest plate containing 100 µl of horse radish peroxidase (HRP)-conjugated goat anti-mouse IgG (Fc) (Jackson ImmunoResearch Laboratories) at a 1:4,000 dilution for 1 hour at room temperature. After the pins are washed as before, the pins are put into wells containing peroxidase substrate solution of diammonium 2,2'-azino-bis [3-ethylbenzthiazoline-b-sulfonate] (ABTS) and $H_2O_2$ (Kirkegaard & Perry Laboratories Inc., Gaithersburg, Md.) for 30 minutes at room temperature for color reaction. The plate is read at 405 nm by a plate reader (e.g., BioTek ELISA plate reader) against a background absorption wavelength of 492 nm. Wells showing color development indicate reactivity of the BoNT peptides in such wells with the test antibodies.

VIII. Assaying for Specific Binding and Neutralizing Activity of Anti-BoNT Antibodies Exemplary antibodies of the present disclosure act, individually or in combination, to specifically bind to, and in some embodiments, neutralize (reduce or eliminate) the toxicity of botulinum neurotoxin type. Neutralization can be evaluated in vivo or in vitro. In vivo neutralization measurements simply involve measuring changes in the lethality (e.g., $LD_{50}$ or other standard metric) due to a BoNT neurotoxin administration with the presence of one or more antibodies being tested for neutralizing activity. The neurotoxin can be directly administered to the test organism (e.g. mouse) or the organism can harbor a botulism infection (e.g., be infected with *Clostridium botulinum*). The antibody can be administered before, during, or after the injection of BoNT neurotoxin or infection of the test animal. A decrease in the rate of progression, or mortality rate indicates that the antibody(s) have neutralizing activity.

One suitable in vitro assay for neutralizing activity uses a hemidiaphragm preparation (Deshpande et al. (1995) *Toxicon,* 33: 551-557). Briefly, left and right phrenic nerve hemidiaphragm preparations are suspended in physiological solution and maintained at a constant temperature (e.g. 36° C.). The phrenic nerves are stimulated supramaximally (e.g. at 0.05 Hz with square waves of 0.2 ms duration). Isometric twitch tension is measured with a force displacement transducer (e.g., GrassModel FT03) connected to a chart recorder.

Purified antibodies are incubated with purified BoNT (e.g. BoNT/A1, BoNT/C, BoNT/F1, etc.) for 30 min at room temperature and then added to the tissue bath, resulting in a final antibody concentration of about $2.0 \times 10^{-8}$ M and a final BoNT concentration of about $2.0 \times 10^{-11}$ M. For each antibody studied, time to 50% twitch tension reduction is determined (e.g., three times for BoNT alone and three times for antibody plus BoNT). Differences between times to a given (arbitrary) percentage (e.g. 50%) twitch reduction are determined by standard statistical analyses (e.g. two-tailed t test) at standard levels of significance (e.g., a P value of <0.05 considered significant).

IX. Diagnostic Assays

As explained above, the anti-BoNT antibodies of the present disclosure can be used for the in vivo or in vitro detection of BoNT toxin and thus, are useful in the diagnosis (e.g. confirmatory diagnosis) of botulism. The detection and/or quantification of BoNT in a biological sample obtained from an organism is indicative of a *Clostridium botulinum* infection of that organism.

The BoNT antigen can be quantified in a biological sample derived from a patient such as a cell, or a tissue sample derived from a patient. As used herein, a biological sample is a sample of biological tissue or fluid that contains a BoNT concentration that may be correlated with and indicative of a *Clostridium botulinum* infection. Examples of suitable biological samples include blood (or blood fraction such as serum or plasma), urine, saliva, and tissue biopsies.

Although the sample is typically taken from a human patient, the assays can be used to detect BoNT antigen in samples from mammals in general, such as dogs, cats, sheep, cattle and pigs, and most particularly primates such as humans, chimpanzees, gorillas, macaques, and baboons, and rodents such as mice, rats, and guinea pigs.

Tissue or fluid samples are isolated from a patient according to standard methods well known to those of skill in the art, most typically by biopsy or venipuncture. The sample is optionally pretreated as necessary by dilution in an appropriate buffer solution or concentrated, if desired. Any of a number of standard aqueous buffer solutions, employing one of a variety of buffers, such as phosphate, Tris, or the like, at physiological pH can be used.

Immunological Binding Assays

The BoNT polypeptide (e.g., BoNT/C, BoNT/D, etc.) can be detected in an immunoassay utilizing only one or more than one of the anti-BoNT antibodies of the present disclosure as a capture agent that specifically binds to the BoNT polypeptide.

As used herein, an immunoassay is an assay that utilizes only one or more than one antibody (e.g. one or more anti-BoNT antibodies listed in FIG. 1 or FIG. 2) to specifically bind an analyte. The immunoassay is characterized by the binding of only one or more than one type of anti-BoNT antibody to a target (e.g. one or more BoNT/C or BonT/D subtypes) as opposed to other physical or chemical properties to isolate, target, and quantify the BoNT analyte.

The BoNT marker can be detected and quantified using any of a number of well recognized immunological binding assays. For example, the antibody of the present disclosure may be immobilized on a substrate (e.g. bead) and/or be the capture antibody in an ELISA. The detection step may take one of many formats known in the art, such as using a labeled secondary antibody or PCR amplification. Where PCR amplification is the method of detection, the antibody is conjugated to a nucleic acid, the antigen may optionally be first attached to a substrate, and the antibody is allowed to be bound to the antigen. The bound antibody-nucleic acid fusion then undergoes PCR amplification of the nucleic acid sequence attached to the antibody. The amplified sequences can in turn be detected via a fluorophore bound to the incorporated nucleotides. The amplified sequences can also be first hybridized to an array before fluorescence is measured to enable multiplexing. Multiplexing encompasses processing and detecting two or more samples and/or two or more analytes in parallel. Details of an assay using antibody-nucleic acid fusion may be found in US 20060141505, disclosure of which is incorporated by reference.

Single assay or multiplex assay can also take the form of an array where signal is detected only by electro-stimulation. In this format, the antibody of the present disclosure is conjugated to an electrochemiluminescent moiety and immobilized on an electrode. A signal (e.g. fluorescence) is emitted due to electrical stimulation at a particular electrode. Details of an assay using electrochemiluminescent moiety in an array may be found in US 20100140086, disclosure of which is incorporated by reference.

A fluorescent compound may be also added later to the assay for visualization by either Luminex type or other type of detection (see, e.g., U.S. Patents 4,366,241; 4,376,110; 4,517,288; and 4,837,168, and the like). For a review of the general immunoassays, see also *Methods in Cell Biology Volume* 37: *Antibodies in Cell Biology*, Asai, ed. Academic Press, Inc. New York (1993); *Basic and Clinical Immunology* 7th Edition, Stites & Ten, eds. (1991)).

The immunoassays of the present disclosure can be performed in any of a number of configurations (see, e.g., those reviewed in Maggio (ed.) (1980) *Enzyme Immunoassay* CRC Press, Boca Raton, Fla.; Tijan (1985) "Practice and Theory of Enzyme Immunoassays," *Laboratory Techniques in Biochemistry and Molecular Biology*, Elsevier Science Publishers B.V., Amsterdam; Harlow and Lane, supra; Chan (ed.) (1987) *Immunoassay: A Practical Guide* Academic Press, Orlando, Fla.; Price and Newman (eds.) (1991) *Principles and Practice of Immunoassays* Stockton Press, NY; and Ngo (ed.) (1988) *Non isotopic Immunoassays* Plenum Press, NY).

Immunoassays often utilize a labeling agent to specifically bind to and label the binding complex formed by the capture agent and the analyte (e.g., an anti- BoNT/C antibody/BoNT/C complex, an anti- BoNT/D antibody/BoNT/D complex, or an anti- BoNT/DC antibody/BoNT/DC complex). The labeling agent can itself be one of the moieties comprising the antibody/analyte complex. Thus, for example, the labeling agent can be a labeled BoNT/C polypeptide or a labeled anti-BoNT/C antibody. Alternatively, the labeling agent is optionally a third moiety, such as another antibody, that specifically binds to the BoNT antibody, the BoNT peptide(s), the antibody/polypeptide complex, or to a modified capture group (e.g., biotin) which is covalently linked to BoNT polypeptide or to the anti- BoNT antibody.

The labeling agent encompasses an antibody that specifically binds to the anti-BoNT antibody. Such agents are well known to those of skill in the art, and most typically comprise labeled antibodies that specifically bind antibodies of the particular animal species from which the anti-BoNT antibody is derived (e.g., an anti-species antibody). Thus, for example, where the capture agent is a human derived BoNT/C antibody, the label agent may be a mouse anti-human IgG, i.e., an antibody specific to the constant region of the human antibody.

Other proteins capable of specifically binding immunoglobulin constant regions, such as streptococcal protein A or protein G are also used as the labeling agent. These proteins are normal constituents of the cell walls of streptococcal bacteria. They exhibit a strong non-immunogenic reactivity with immunoglobulin constant regions from a variety of species (see generally Kronval, et al., (1973) *J. Immunol.*, 111:1401-1406, and Akerstrom, et al., (1985) *J. Immunol.*, 135:2589-2542, and the like).

Throughout the assays, incubation and/or washing steps may be required after each combination of reagents. Incubation steps can vary from about 5 seconds to several hours, for example, from about 5 minutes to about 24 hours (e.g., from 5 minutes to 15 minutes, from 15 minutes to 30 minutes, from 30 minutes to 60 minutes, from 1 hour to 4 hours, from 4 hours to 8 hours, from 8 hours to 12 hours, or from 12 hours to 24 hours). However, the incubation time will depend upon the assay format, analyte, volume of solution, concentrations, and the like. Usually, the assays are carried out at ambient temperature, although they can be conducted over a range of temperatures, such as 5° C. to 45° C.

Non Competitive Assay Formats

Immunoassays for detecting BoNT neurotoxins (e.g. BoNT serotypes and/or subtypes) may be either competitive or noncompetitive. Noncompetitive immunoassays are assays in which the amount of captured analyte (in this case, BoNT polypeptide) is directly measured. In one example of a suitable "sandwich" assay, the capture agent (e.g., an anti-BoNT antibody) is bound directly or indirectly to a solid substrate where it is immobilized. These immobilized anti-BoNT antibodies capture BoNT polypeptide(s) present in a test sample (e.g., a blood sample). The BoNT polypeptide(s) thus immobilized are then bound by a labeling agent, e.g., an anti-BoNT antibody bearing a label. Alternatively, the second antibody may lack a label, but it may, in turn, be bound by a labeled third antibody specific to antibodies of the species from which the second antibody is derived. Free labeled antibody is washed away and the remaining bound labeled antibody is detected (e.g., using a gamma detector where the label is radioactive).

Competitive Assay Formats

In competitive assays, the amount of analyte (e.g., BoNT) present in the sample is measured indirectly by measuring the amount of an added (exogenous) analyte displaced (or competed away) from a capture agent (e.g., anti-BoNT antibody) by the analyte present in the sample. For example, in one competitive assay, a known amount of BoNT is added to a test sample with an unquantified amount of BoNT, and the sample is contacted with a capture agent, e.g., an anti-BoNT antibody that specifically binds BoNT/C. The amount of added BoNT that binds to the anti-BoNT antibody is inversely proportional to the concentration of BoNT/C present in the test sample.

The anti-BoNT antibody can be immobilized on a solid substrate. The amount of BoNT bound to the anti-BoNT antibody is determined either by measuring the amount of BoNT present in a BoNT-anti-BoNT antibody complex, or alternatively by measuring the amount of remaining uncomplexed BoNT.

Reduction of Non-Specific Binding

One of skill will appreciate that it is often desirable to reduce non-specific binding in immunoassays and during analyte purification. Where the assay involves, for example BoNT/C polypeptide(s), BoNT/C-binding antibody, or other capture agent(s) immobilized on a solid substrate, it is desirable to minimize the amount of non-specific binding to the substrate. Means of reducing such non-specific binding are well known to those of skill in the art. Typically, this involves coating the substrate with a proteinaceous composition. In particular, protein compositions such as bovine serum albumin (BSA), nonfat powdered milk, and gelatin are widely used.

Substrates

As mentioned above, depending upon the assay, various components, including the BoNT polypeptide(s), anti-BoNT antibodies, etc., are optionally bound to a solid surface. Many methods for immobilizing biomolecules to a variety of solid surfaces are known in the art. For instance, the solid surface may be a membrane (e.g., nitrocellulose), a microtiter dish (e.g., PVC, polypropylene, or polystyrene), a test tube (glass or plastic), a dipstick (e.g., glass, PVC, polypropylene, polystyrene, latex, and the like), a microcentrifuge tube, or a glass, silica, plastic, metallic or polymer bead. The desired component may be covalently bound, or noncovalently attached through nonspecific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which may be employed include paper, glasses, ceramics, metals, metalloids, semiconductive materials, cements or the like. In addition, substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12-24 carbon atoms) alkyl ammonium salts and the like are also suitable. Where the solid surface is porous, various pore sizes may be employed depending upon the nature of the system.

In preparing the surface, a plurality of different materials may be employed, e.g., as laminates, to obtain various properties. For example, protein coatings, such as gelatin can be used to avoid non-specific binding, simplify covalent conjugation, and enhance signal detection or the like.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature. See, for example, *Immobilized Enzymes*, Ichiro Chibata, Halsted Press, New York, 1978, and Cuatrecasas, (1970) *J. Biol. Chem.* 245 3059.

In addition to covalent bonding, various methods for noncovalently binding an assay component can be used. Noncovalent binding is typically nonspecific absorption of a compound to the surface. Typically, the surface is blocked with a second compound to prevent nonspecific binding of labeled assay components. Alternatively, the surface is designed such that it nonspecifically binds one component but does not significantly bind another. For example, a surface bearing a lectin such as concanavalin A will bind a carbohydrate containing compound but not a labeled protein that lacks glycosylation. Various solid surfaces for use in noncovalent attachment of assay components are reviewed in U.S. Pat. Nos. 4,447,576 and 4,254,082, which is incorporated herein by reference.

Other Assay Formats

BoNT polypeptides or anti-BoNT antibodies (e.g. BoNT neutralizing antibodies and antibodies that specifically bind to BoNT) can also be detected and quantified by any of a number of other means well known to those of skill in the art. These include analytic biochemical methods such as spectrophotometry, radiography, electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like.

Western blot analysis and related methods can also be used to detect and quantify the presence of BoNT polypeptides in a sample. The technique generally comprises separating sample products by gel electrophoresis on the basis of molecular weight, transferring the separated products to a suitable solid support, (such as a nitrocellulose filter, a nylon filter, or derivatized nylon filter), and incubating the sample with the antibodies that specifically bind either the BoNT polypeptide. The antibodies specifically bind to the biological agent of interest on the solid support. These antibodies are directly labeled or alternatively are subsequently detected using labeled antibodies (e.g., labeled sheep anti-human antibodies where the antibody to a marker gene is a human antibody) which specifically bind to the antibody which binds the BoNT polypeptide.

Other assay formats include liposome immunoassays (LIAs), which use liposomes designed to bind specific molecules (e.g., antibodies) and release encapsulated reagents or markers. The released chemicals are then detected according to standard techniques (see, Monroe et al., (1986) *Amer. Clin. Prod. Rev.* 5:34-41).

Labeling of Anti-BoNT Antibodies

Anti-BoNT antibodies can be labeled by any of a number of methods known to those of skill in the art. Thus, for example, the labeling agent can be, e.g., a monoclonal antibody, a polyclonal antibody, a protein or complex such as those described herein, or a polymer such as an affinity matrix, carbohydrate or lipid. Detection proceeds by any known method, including immunoblotting, western analysis, gel-mobility shift assays, tracking of radioactive or bioluminescent markers, nuclear magnetic resonance, electron paramagnetic resonance, stopped-flow spectroscopy, column chromatography, capillary electrophoresis, or other methods which track a molecule based upon an alteration in size and/or charge. The detectable group can be any material having a detectable physical or chemical property. Such detectable labels have been well-developed in the field of immunoassays and, in general, any label useful in such methods can be applied in the various embodiments of the present disclosure. Thus, a label is any composition detectable by spectroscopic, photochemical, biochemical, immunochemical, electrical, optical or chemical means. Useful labels in the present disclosure include magnetic beads (e.g. Dynabeads™), fluorescent dyes (e.g., fluorescein isothiocyanate, Texas red, rhodamine, Alexa fluor dyes and the like), radiolabels (e.g., $^3$H, $^{125}$I, $^{35}$S, $^{14}$C, or $^{32}$P), enzymes (e.g., LacZ, CAT, horse radish peroxidase, luciferase, alkaline phosphatase and others, commonly used as detectable enzymes, either as marker gene products or in an ELISA), and colorimetric labels such as colloidal gold or colored glass or plastic (e.g. polystyrene, polypropylene, latex, etc.) beads. For example, an antibody can include a fluorescent label, a chemiluminescent label, a radiolabel, a chromogenic label, or other suitable label.

The label may be coupled directly or indirectly to the desired component of the assay according to methods well known in the art. As indicated above, a wide variety of labels may be used, with the choice of label depending on the sensitivity required, ease of conjugation of the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see, U.S. Pat. No. 4,391,904, which is incorporated herein by reference.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence, e.g., by microscopy, visual inspection, via photographic film, by the use of electronic detectors such as charge coupled devices (CCDs) or photomultipliers and the like. Similarly, enzymatic labels may be detected by providing appropriate substrates for the enzyme and detecting the resulting reaction product. Finally, simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of BoNT peptides. In this case, antigen-coated particles are agglutinated by samples comprising the target antibodies. In this format, none of the components need be labeled and the presence of the target antibody is detected by simple visual inspection.

X. Compositions

The BoNT-binding antibodies of this disclosure are useful in preventing or mitigating the progression of botulism produced, e.g., by endogenous disease processes or by chemical/biological warfare agents. Typically compositions containing one, two, or more different antibodies can be provided as a pharmaceutical composition and administered to a mammal (e.g., to a human) in need thereof.

As disclosed herein, particularly efficient neutralization of a botulism neurotoxin (BoNT) can be achieved by the use of antibodies that bind two or more BoNT subtypes/serotypes/mosaics with high affinity. This can be accomplished by using one, two or more different antibodies. Where there is more than one type of antibody, each can be directed against a different subtype. One or more of the antibodies can also be cross-reactive. Cross-reactive antibodies can bind two or more BoNT serotypes/subtypes (e.g., BoNT/CD, BoNT/D, BoNT/DC, BoNT/C etc.) with high affinity.

Different neutralizing antibodies when combined, exhibit a potency that is increased dramatically. This increase makes it possible to generate a botulinum antibody composition of the required potency for therapeutic use. Compositions comprising at least two, at least three, or more high affinity antibodies that bind overlapping or non-overlapping epitopes on the BoNT are contemplated herein.

Compositions contemplated herein may contain at least one antibody from the antibodies of the present disclosure (e.g. any of the clones as shown in FIG. 1 or FIG. 2). For example, the composition may include antibodies comprising one or more CDRs from these antibodies, and/or one or more antibodies comprising mutants or derivatives of these antibodies. Examples of compositions of the present disclosure comprise one antibody selected from 4C10, 4C10.1, 4C10.2, 4C10.5, 4C10.8, 4C10.15, 4C10.17, 4C10.18, 4C10.20, 4C10.22, which antibodies can be provided in combination with a pharmaceutical carrier. In some cases, the compositions of the present disclosure comprise at least one 4C10 antibody or any of its derivatives, in combination with at least one, at least 2, at least 3, or at least 4 antibodies such as 4C4 or its derivatives (e.g. 4C4.2, 4C4.4, 4C4.5, 4C4.6, 4C4.7, 4C4.8, 4C4.9, 4C4.10), 8DC1 or its derivatives (e.g. 8DC1.4, 8DC1.5, 8DC1.6), and 8DC4 or its derivatives (8DC4.3, 8DC4.3SP, 8DC4.4, 8DC4.4AT). Examples of compositions of the present disclosure comprise one of the 4C10 antibodies or its derivatives (e.g. 4C10.1, 4C10.2, 4C10.5, 4C10.8, 4C10.15, 4C10.17, 4C10.18, 4C10.20, 4C10.22), which antibody can be provided in combination with 4C4 or its derivatives, 8DC1 or its derivatives, and/or 8DC4 or its derivatives, and a pharmaceutical carrier. In some cases, the composition comprises: a) at least one 4C10 antibody selected from the group consisting of: 4C10.1, 4C10.2, 4C10.5, 4C10.8, 4C10.15, 4C10.17, 4C10.18, 4C10.20, and 4C10.22; and b) at least one, at least 2, at least 3, or at least 4 antibodies selected from the group consisting of: 4C4, 4C4.2, 4C4.4, 4C4.5, 4C4.6, 4C4.7, 4C4.8, 4C4.9, 4C4.10, 8DC1, 8DC1.4, 8DC1.5, 8DC1.6, 8DC4, 8DC4.3, 8DC4.3SP, 8DC4.4, and 8DC4.4AT. In some cases, the composition comprises: a) at least one 4C10 antibody selected from the group consisting of: 4C10.1, 4C10.2, 4C10.5, 4C10.8, 4C10.15, 4C10.17, 4C10.18, 4C10.20, and 4C10.22; b) at least one, at least 2, at least 3, or at least 4 antibodies selected from the group consisting of: 4C4, 4C4.2, 4C4.4, 4C4.5, 4C4.6, 4C4.7, 4C4.8, 4C4.9, 4C4.10, 8DC1, 8DC1.4, 8DC1.5, 8DC1.6, 8DC4, 8DC4.3, 8DC4.3SP, 8DC4.4, and 8DC4.4AT; and c) a pharmaceutical carrier.

The subject composition encompasses compositions that specifically bind to one or more serotypes/subtypes/mosaics. The composition can contain one or more antibodies that are cross-reactive. The composition may also contain any first combination of antibodies described above that specifically bind to one serotype together with a second combination of antibodies that specifically binds to, and in some embodiments, specifically neutralizes a different serotype. The subject composition may contain multiple combinations such that that composition may bind and/or neturalize two, three, or more serotypes/subtypes (e.g. BonT/C, BoNT/CD, BoNT/D, BoNT/DC, etc.).

A composition that specifically binds to, and in some embodiments, neutralizes multiple serotypes may include any of the combinations described above or one or more of the antibodies disclosed in Tables 1-10 and/or FIG. 1 and/or FIG. 2.

Where combinations of antibodies are disclosed herein, such combinations can be provided in a single formulation or can be provided as separate formulations in a kit, where the separate formulations may contain a single antibody or more antibodies. Such separate formulations of a kit may be combined prior to administration or administered by separate injection.

The anti-BoNT antibodies provided by the present disclosure are useful for parenteral, topical, oral, or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, capsules and lozenges. The antibodies present in the pharmaceutical compositions of the present disclosure, when administered orally, can be protected from digestion. This is typically accomplished either by complexing the antibodies with a composition to render them resistant to acidic and enzymatic hydrolysis or by packaging the antibodies in an appropriately resistant carrier such as a liposome. Means of protecting proteins from digestion are well known in the art.

The present disclosure provides a pharmaceutical composition comprising an antibody comprising a $V_H$ of a subject antibody. The present disclosure provides a pharmaceutical composition comprising an antibody comprising a $V_L$ of a subject antibody. The present disclosure provides a pharmaceutical composition comprising an amino acid sequence of a $V_H$ and a $V_L$ of a subject antibody. In some instances, a subject pharmaceutical composition comprises an amino acid sequence comprising a $V_H$ CDR1, CDR2, and CDR3 of a subject antibody and/or a $V_L$ CDR1, CDR2, and CDR3 of a subject antibody.

The pharmaceutical compositions of the present disclosure are particularly useful for parenteral administration, such as intravenous administration or administration into a body cavity or lumen of an organ. The compositions for administration can comprise a solution of one or more anti-BoNT antibody dissolved in a pharmaceutically acceptable carrier, which may be an aqueous carrier. A variety of aqueous carriers can be used, e.g., buffered saline and the like.

The pharmaceutical composition of the present disclosure, in some cases, comprises: a pharmaceutically acceptable carrier; and at least a first antibody that cross-reacts with and specifically binds to Botulinum neurotoxin serotype BoNT/C and Botulinum neurotoxin serotype BoNT/D, and their mosaics, wherein the antibody specifically binds an epitope of a Botulinum neurotoxin that is specifically bound by an antibody comprising a) a $V_H$ comprising a CDR1, CDR2 and CDR3, wherein CDR1, CDR2, and CDR3 of an antibody is selected from the group consisting 4C10.5, 4C10.8, 4C10.15, 4C10.17, 4C10.18, 4C10.20, and 4C10.22; and b) a $V_L$ comprising a CDR1, CDR2 and CDR3, wherein the CDR1, CDR2, and CDR3 of an antibody is selected from the group consisting of 4C10.5, 4C10.8, 4C10.15, 4C10.17, 4C10.18, 4C10.20, and 4C10.22.

The pharmaceutical composition of the present disclosure, in some cases, comprises a pharmaceutically acceptable carrier; and at least a first antibody that cross-reacts with and neutralizes Botulinum neurotoxin serotype BoNT/C and Botulinum neurotoxin serotype BoNT/D, wherein the antibody comprises: a) a $V_H$ comprising a CDR1, CDR2 and CDR3, wherein CDR1, CDR2, and CDR3 of an antibody is selected from the group consisting 4C10.5, 4C10.8, 4C10.15, 4C10.17, 4C10.18, 4C10.20, and 4C10.22; and b) a $V_L$ comprising a CDR1, CDR2 and CDR3, wherein the CDR1, CDR2, and CDR3 of an antibody is selected from the group consisting of 4C10.5, 4C10.8, 4C10.15, 4C10.17, 4C10.18, 4C10.20, and 4C10.22.

In some cases, the pharmaceutical composition comprises a first anti-BoNT antibody binds a Botulinum neurotoxin C, D, or mosaics BoNT/CD and BoNT/DC. In some cases, the BoNT antibody binds more than one subtype of Botulinum neurotoxin.

In some cases, the pharmaceutical composition comprises a first antibody that is a 4C10 antibody or its derivatives, and a second antibody selected from the group consisting of 4C4 or its derivatives (e.g. 4C4.2, 4C4.4, 4C4.5, 4C4.6, 4C4.7, 4C4.8, 4C4.9, 4C4.10), 8DC1 or its derivatives (e.g. 8DC1.4, 8DC1.5, 8DC1.6), and/or 8DC4 or its derivatives (8DC4.3, 8DC4.3SP, 8DC4.4, 8DC4.4AT). In some cases, the pharmaceutical composition comprises a first antibody selected from the group consisting of: 4C10.5, 4C10.8, 4C10.15, 4C10.17, 4C10.18, 4C10.20, and 4C10.22; and a second antibody selected from the group consisting of 4C4, 4C4.2, 4C4.4, 4C4.5, 4C4.6, 4C4.7, 4C4.8, 4C4.9, 4C4.10, 8DC1, 8DC1.4, 8DC1.5, 8DC1.6, 8DC4, 8DC4.3, 8DC4.3SP, 8DC4.4, and 8DC4.4AT. In some cases, the pharmaceutical composition comprises a first antibody that is a 4C10 antibody or its derivatives, and a second antibody selected from the group consisting of 4C4 or its derivatives (e.g. 4C4.2, 4C4.4, 4C4.5, 4C4.6, 4C4.7, 4C4.8, 4C4.9, 4C4.10), 8DC1 or its derivatives (e.g. 8DC1.4, 8DC1.5, 8DC1.6), and/or 8DC4 or its derivatives (8DC4.3, 8DC4.3SP, 8DC4.4, 8DC4.4AT). In some cases, the pharmaceutical composition comprises a first antibody selected from the group consisting of: 4C10.5, 4C10.8, 4C10.15, 4C10.17, 4C10.18, 4C10.20, and 4C10.22; a second antibody selected from the group consisting of 4C4, 4C4.2, 4C4.4, 4C4.5, 4C4.6, 4C4.7, 4C4.8, 4C4.9, 4C4.10, 8DC1, 8DC1.4, 8DC1.5, 8DC1.6, 8DC4, 8DC4.3, 8DC4.3SP, 8DC4.4, and 8DC4.4AT; and a pharmaceutical carrier.

Non- aqueous pharmaceutically acceptable carriers (excipients) are known to those of skill in the art. Such excipients can comprise any substance that is biocompatible and liquid or soft enough at the subject's body temperature to release the active agent(s) (e.g., Anti-BoNT antibodies) into the subject's bloodstream at a desired rate. Non-aqueous carriers are usually hydrophobic and commonly organic, e.g., an oil or fat of vegetable, animal, mineral or synthetic origin or derivation. The carrier may include at least one chemical moiety of the kind that typifies "fatty" compounds, e.g., fatty acids, alcohols, esters, etc., i.e., a hydrocarbon chain, an ester linkage, or both. "Fatty" acids in this context include, but are not limited to, acetic, propionic and butyric acids through straight-or branched-chain organic acids containing up to 30 or more carbon atoms. The non-aqueous carrier may be immiscible in water and/or soluble in the substances commonly known as fat solvents. The non-aqueous carrier can correspond to a reaction product of a "fatty" compound or compounds with a hydroxy compound, e, g., a mono-hydric, di-hydric, trihydric or other polyhydric alcohol, e.g., glycerol, propanediol, lauryl alcohol, polyethylene or-propylene glycol, etc. These compounds include, but are not limited to, the fat-soluble vitamins, e.g., tocopherols and their esters, e.g., acetates sometimes produced to stabilize tocopherols. Sometimes, for economic reasons, the carrier can comprise a natural, unmodified vegetable oil such as sesame oil, soybean oil, peanut oil, palm oil, or an unmodified fat. Alternatively, the vegetable oil or fat may be modified by hydrogenation or other chemical means which is compatible with the present disclosure. The appropriate use of hydrophobic substances prepared by synthetic means is also envisioned. Non-aqueous excipient compositions can also comprise, in addition to a biocompatible oil, an "antihydration agent" which term as used herein means a substance that retards hydration of the active agent(s) and/or the biocompatible oil or fat and thereby further decreases and/or stabilizes the rate of release of the active agent(s) from that composition following administration to an animal (e.g. human) A great variety of non-toxic antihydration agents are known. By way of example there are "gelling" agents that, when dispersed, and in some cases heated to dissolve them in the oil, give the body of oil greater visco-elasticity (and therefore greater structural stability) and thereby slow down penetration of the oil by body fluids.

Illustrative antihydration agents include various polyvalent metal salts or complexes of organic acids, for instance fatty acids having from about 8 or 10 to about 20 or 22 carbon atoms, e.g., aluminum, zinc, magnesium or calcium salts of lauric acid, palmitic acid, stearic acid and the like. Such salts can be mono-, di- or tri- substituted, depending on the valence of the metal and the degree of oxidation of the metal by the acid. Of common usage are the aluminum salts of such fatty acids. Aluminum monostearate and distearate are frequently used anti-hydration agents. Others that are useful include aluminum tristearate, calcium mono-and distearate, magnesium mono-and distearate and the corresponding palmitates, laurates and the like. The concentration of such an antihydration agent, based on the weight of the oil plus that agent, may be between about 1% and about 10% (most typically between about 2% and about 5%), although other concentrations may be suitable in some cases.

The various solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of anti-BoNT antibody in these formulations can vary widely, and will be selected primarily based on fluid volumes, viscosities, body weight and the like in accordance with the particular mode of administration selected and the patient's needs. In some instances, the solutions may be stored in lyophilized or frozen form. Examples of suitable anti-BoNT antibody formulations are described in WO 2011/028961.

Thus, a typical pharmaceutical composition for intravenous administration would be about 0.1 mg to 10 mg per patient per day. Dosages from about 1 mg up to about 200 mg per patient per day can be used. Methods for preparing parenterally administrable compositions will be known or apparent to those skilled in the art and are described in more detail in such publications as *Remington's Pharmaceutical Science,* 15th ed., Mack Publishing Company, Easton, Pa. (1980).

The compositions containing the anti-BoNT antibodies of the present disclosure or a cocktail thereof can be administered for therapeutic and/or prophylactic treatments. Pharmaceutical compositions can be administered in a dosage sufficient to neutralize (mitigate or eliminate) the BoNT toxin(s) (i.e., reduce or eliminate a symptom of BoNT poisoning (botulism)). An amount adequate to accomplish this is defined as a "therapeutically effective dose." Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the antibodies of the present disclosure to effectively treat the patient.

The present disclosure thus provides a method of specifically binding to, and in some cases, neutralizing a Botulinum neurotoxin in an individual (e.g., a human; or a non-human mammal), the method generally involving administering to the individual an effective amount of a subject anti-BoNT antibody, or an effective amount of a subject composition comprising a subject anti-BoNT antibody. The treatments essentially comprise administering to the poisoned organism (e.g. human or non-human mammal) a quantity of one or more neutralizing antibodies sufficient to neutralize (e.g. mitigate or eliminate) symptoms of BoNT poisoning. Administering the antibody, or the composition comprising the antibody, provides for specific binding to and, in some embodiments neutralization of, Botulinum neurotoxin present in the individual. The BoNT poisoning can be due to ingestion of contaminated food products (food botulism), can result from an anaerobic wound infection (wound botulism), or can result from an act of biological warfare or bioterrorism.

The present disclosure also provides methods of reducing the likelihood that an individual at risk of exposure to Botulinum neurotoxin will experience symptoms of Botulinum neurotoxin poisoning following exposure to the Botulinum neurotoxin (e.g., where the exposure is via inhalation, via ingestion, via a wound infection, or via another route/mode of exposure). Administration of a subject antibody or subject composition reduces the likelihood that the individual will experience symptoms of Botulinum neurotoxin poisoning. Thus, e.g., a subject anti-BoNT antibody, or a subject composition comprising a subject anti-BoNT antibody, can be administered to an individual before the individual has Botulinum neurotoxin poisoning, e.g., before a BoNT is present in the individual. For example, a subject anti-BoNT antibody, or a subject composition comprising a subject anti-BoNT antibody, can be administered to an individual who is at risk of BoNT exposure, e.g., an individual who is at greater risk than the general population of experiencing Botulinum neurotoxin exposure and poisoning. Such individuals include, e.g., military personnel, e.g., military personnel in a combat setting; personnel involved in investigation or clean up of a site suspected of involving Botulinum neurotoxin exposure (e.g., hazardous materials ("hazmat") personnel) and other individuals who are at risk of Botulinum neurotoxin exposure, either accidental or intentional.

XI. Kits for Diagnosis or Treatment

Kits for the treatment of botulism or for the detection/confirmation of a *Clostridium botulinum* infection are also provided. Kits will typically comprise one or more anti-BoNT antibodies (e.g., anti-BoNT antibodies in a composition for pharmaceutical use). For diagnostic purposes, the antibody(s) can optionally be labeled. In addition, the kits will typically include instructional materials disclosing means of use anti-BoNT antibodies in the treatment of symptoms of botulism. The kits may also include additional components to facilitate the particular application for which the kit is designed. Thus, for example, where a kit contains one or more anti-BoNT antibodies for detection of diagnosis of BoNT subtype, the antibody can be labeled, and the kit can additionally contain means of detecting the label (e.g. enzyme substrates for enzymatic labels, filter sets to detect fluorescent labels, appropriate secondary labels such as a sheep anti-human antibody, or the like). The kits may additionally include buffers and other reagents routinely used for the practice of a particular method. Such kits and appropriate contents are well known to those of skill in the art.

Kits provided for the treatment of botulism may contain one or more anti-BoNT antibodies. The antibodies can be provided separately or mixed together. Typically, the antibodies will be provided in a sterile pharmacologically acceptable excipient. The antibodies can also be provided pre-loaded into a delivery device (e.g., a disposable syringe).

The kits can optionally include instructional materials teaching the use of the antibodies, recommended dosages, contraindications, and the like.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-39 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. An isolated antibody that cross-reacts with and specifically binds to Botulinum neurotoxin serotype BoNT/C, Botulinum neurotoxin serotype BoNT/D, Botulinum neurotoxin serotype BoNT/CD, and/or Botulinum neurotoxin serotype BoNT/DC, wherein the antibody specifically binds an epitope of a Botulinum neurotoxin that is specifically bound by an antibody comprising: a) a $V_H$ comprising a CDR1, CDR2 and CDR3, wherein the CDR1, CDR2 and CDR3 are selected from a $V_H$ of an antibody selected from the group consisting of 4C10.5, 4C10.8, 4C10.15, 4C10.17, 4C10.18, 4C10.20, and 4C10.22; and b) a $V_L$ comprising a CDR1, CDR2 and CDR3, wherein the CDR1, CDR2 and CDR3 are selected from a $V_L$ of an antibody selected from the group consisting 4C10.5, 4C10.8, 4C10.15, 4C10.17, 4C10.18, 4C10.20, and 4C10.22.

Aspect 2. The isolated antibody of aspect 1, wherein said antibody is selected from the group consisting of 4C10.5, 4C10.8, 4C10.15, 4C10.17, 4C10.18, 4C10.20, and 4C10.22.

Aspect 3. The isolated antibody of aspect 1, wherein said antibody competes for binding to a Botulinum neurotoxin with an antibody comprising: a) a $V_L$ CDR1 comprising an amino acid sequence of $V_L$ CDR1 of 4C10.20; b) a $V_L$ CDR2 comprising an amino acid sequence of $V_L$ CDR2 of 4C10.20; and c) a $V_L$ CDR3 comprising an amino acid sequence of $V_L$ CDR3 of 4C10.20.

Aspect 4. The isolated antibody of aspect 1, wherein said antibody competes for binding to a Botulinum neurotoxin with an antibody comprising: a) a $V_H$ CDR1 comprising an amino acid sequence of $V_H$ CDR1 of 4C10.20; b) a $V_H$ CDR2 comprising an amino acid sequence of $V_H$ CDR2 of 4C10.20; and c) a $V_H$ CDR3 comprising an amino acid sequence of $V_H$ CDR3 of 4C10.20.

Aspect 5. The isolated antibody of aspect 1, wherein said antibody that binds to a Botulinum neurotoxin, wherein the antibody comprises: a) a $V_H$ CDR1 comprising an amino acid sequence of $V_H$ CDR1 of 4C10.20; b) a $V_H$ CDR2 comprising an amino acid sequence of $V_H$ CDR2 of 4C10.20; c) a $V_H$ CDR3 comprising an amino acid sequence of $V_H$ CDR3 of 4C10.20; d) a $V_L$ CDR1 comprising an amino acid sequence of $V_L$ CDR1 of 4C10.20; e) a $V_L$ CDR2 comprising an amino acid sequence of $V_L$ CDR2 of 4C10.20; and f) a $V_L$ CDR3 comprising an amino acid sequence of $V_L$ CDR3 of 4C10.20.

Aspect 6. An isolated antibody that binds to a Botulinum neurotoxin, wherein the antibody comprises: a) a full length $V_H$ comprising the amino acid sequence of the full length $V_H$ of 4C10.20; b) a full length $V_L$ comprising the amino acid sequence of the full length $V_L$ of 4C10.20; c) a $V_H$ CDR1 comprising the amino acid sequence of $V_H$ CDR1 of 4C10.20, a $V_H$ CDR2 comprising an amino acid sequence of $V_H$ CDR2 of 4C10.20, and a $V_H$ CDR3 comprising an amino acid sequence of $V_H$ CDR3 of 4C10.20; d) a $V_L$ CDR1 comprising the amino acid sequence of $V_L$ CDR1 of 4C10.20, a $V_L$ CDR2 comprising an amino acid sequence of $V_L$ CDR2 of 4C10.20, and a $V_L$ CDR3 comprising an amino acid sequence of $V_L$ CDR3 of 4C10.20; e) a $V_H$ CDR1 comprising the amino acid sequence of $V_H$ CDR1 of 4C10.20, a $V_H$ CDR2 comprising an amino acid sequence of $V_H$ CDR2 of 4C10.20, a $V_H$ CDR3 comprising an amino acid sequence of $V_H$ CDR3 of 4C10.20, a $V_L$ CDR1 comprising an amino acid sequence of $V_L$ CDR1 of 4C10.20; a $V_L$ CDR2 comprising an amino acid sequence of $V_L$ CDR2 of 4C10.20, and a $V_L$ CDR3 comprising an amino acid sequence of $V_L$ CDR3 of 4C10.20; or f) a full length $V_H$ comprising an amino acid sequence of the full length $V_H$ of 4C10.20, and a full length $V_L$ comprising an amino acid sequence of the full length $V_L$ of 4C10.20. Aspect 7. The isolated antibody of aspect 6, wherein the antibody comprises the full length $V_H$ comprising an amino acid sequence of the full length $V_H$ of 4C10.20.

Aspect 8. The isolated antibody of aspect 6, wherein the antibody comprises the full length $V_L$ comprising an amino acid sequence of the full length $V_L$ of 4C10.20.

Aspect 9. The isolated antibody of aspect 6, wherein the antibody comprises the full length $V_H$ comprising an amino acid sequence of the full length $V_H$ of 4C10.20; and the full length $V_L$ comprising an amino acid sequence of the full length $V_L$ of 4C10.20.

Aspect 10. The isolated antibody of aspect 6, wherein the antibody comprises the $V_H$ CDR1 comprising an amino acid sequence of $V_H$ CDR1 of 4C10.20; the $V_H$ CDR2 comprising an amino acid sequence of $V_H$ CDR2 of 4C10.20; the $V_H$ CDR3 comprising an amino acid sequence of $V_H$ CDR3 of 4C10.20; the $V_L$ CDR1 comprising an amino acid sequence of $V_L$ CDR1 of 4C10.20; the $V_L$ CDR2 comprising an amino acid sequence of $V_L$ CDR2 of 4C10.20; and the $V_L$ CDR3 comprising an amino acid sequence of $V_L$ CDR3 of 4C10.20.

Aspect 11. The isolated antibody of aspect 1, wherein said antibody competes for binding to a Botulinum neurotoxin with an antibody comprising: a) a $V_H$ CDR1 comprising an amino acid sequence of $V_H$ CDR1 of 4C10.20, a $V_H$ CDR2 comprising an amino acid sequence of $V_H$ CDR2 of 4C10.20, and a $V_H$ CDR3 comprising an amino acid sequence of $V_H$ CDR3 of 4C10.20; and b) a $V_L$ CDR1 comprising an amino acid sequence of $V_L$ CDR1 of an antibody selected from the group consisting of 4C10.5, 4C10.8, 4C10.15, 4C10.17, 4C10.18, and 4C10.22, a $V_L$ CDR2 comprising an amino acid sequence of $V_L$ CDR2 of an antibody selected from the group consisting of 4C10.5, 4C10.8, 4C10.15, 4C10.17, 4C10.18, and 4C10.22, and a $V_L$ CDR3 comprising an amino acid sequence of $V_L$ CDR3 of an antibody selected from the group consisting of 4C10.5, 4C10.8, 4C10.15, 4C10.17, 4C10.18, and 4C10.22.

Aspect 12. The isolated antibody of any one of aspects 1-11, wherein said antibody is a human antibody or a humanized antibody.

Aspect 13. The isolated antibody of any one of aspects 1-12, wherein said antibody is a single chain Fv (scFv), IgG, Fab, (Fab')$_2$, or (scFv')$_2$.

Aspect 14. The isolated antibody of any one of aspects 1-13, wherein said antibody cross-reacts with Botulinum neurotoxin serotype BoNT/C, serotype BoNT/D, and a mosaic of BoNT/CD or BoNT/DC.

Aspect 15. The isolated antibody of any one of aspects 1-14, wherein said antibody has a $K_D$ with a Botulinum neurotoxin of about 5 nM or less.

Aspect 16. The isolated antibody of any one of aspects 1-15, wherein said antibody binds to BoNT/C, BoNT/D, or a mosaic thereof with high affinity.

Aspect 17. A composition comprising: a pharmaceutically acceptable carrier; and at least a first antibody in according to any one of aspects 1-16, Aspect 18. The composition of aspect 17, wherein said first antibody binds a Botulinum neurotoxin serotype of serotype C, D, or a mosaic of serotype C and D.

Aspect 19. The composition of aspect 17, wherein said first antibody binds more than one subtype of Botulinum neurotoxin.

Aspect 20. The composition of aspect 17, comprising a second antibody, wherein said second antibody is an antibody of aspect 1 that is different from said first antibody.

Aspect 21. The composition of aspect 17, comprising a second antibody that binds to a BoNT epitope that is different from that Botulinum neurotoxin serotype bound by said first antibody.

Aspect 22. A method of specifically binding to a Botulinum neurotoxin in a mammal comprising: administering to said mammal an effective amount of an antibody of any one of aspects 1 and 6; wherein said administering provides for specific binding of Botulinum neurotoxin present in the mammal.

Aspect 23. A method of specifically binding to a Botulinum neurotoxin in a mammal, comprising: administering to said mammal an effective amount of a composition of aspect 17; wherein said administering provides for specific binding of Botulinum neurotoxin present in the mammal.

Aspect 24. An isolated nucleic acid comprising a nucleotide sequence encoding the amino acid sequence of: a $V_H$ of an antibody comprising a CDR1, CDR2 and CDR3, wherein the CDR1, CDR2 and CDR3 are present in an antibody selected from the group consisting of 4C10.5, 4C10.8, 4C10.15, 4C10.17, 4C10.18, 4C10.20, and 4C10.22; and a $V_L$ of an antibody comprising a CDR1, CDR2 and CDR3, wherein the CDR1, CDR2 and CDR3 are present in an antibody selected from the group consisting of 4C10.5, 4C10.8, 4C10.15, 4C10.17, 4C10.18, 4C10.20, and 4C10.22.

Aspect 25. The isolated nucleic acid of aspect 24, wherein the isolated nucleic acid comprises the nucleotide sequence encoding an amino acid sequence of: the $V_H$ of an antibody comprising a CDR1, CDR2 and CDR3, wherein the CDR1, CDR2 and CDR3 of the antibody are present in the $V_H$ of the antibody 4C10.20; and the $V_L$ of an antibody comprising a CDR1, CDR2 and CDR3, wherein the CDR1, CDR2 and CDR3 of the antibody are present in the $V_L$ of the antibody 4C10.20.

Aspect 26. A cell containing the nucleic acid of aspect 24.

Aspect 27. An isolated nucleic acid comprising a nucleotide sequence encoding an amino acid sequence of a variable heavy chain ($V_H$) polypeptide comprising a $V_H$ CDR1 selected from a $V_H$ of the antibody 4C10.20, a $V_H$ CDR2 comprising a $V_H$ CDR2 selected from a $V_H$ of the antibody 4C10.20, and a $V_H$ CDR2 selected from a $V_H$ of the antibody 4C10.20.

Aspect 28. A variable heavy chain ($V_H$) polypeptide encoded by the nucleic acid of aspect 27.

Aspect 29. An isolated nucleic acid comprising a nucleotide sequence encoding an amino acid sequence of a variable light chain ($V_L$) polypeptide comprising a $V_L$ CDR1 selected from a $V_L$ of the antibody 4C10.20, a $V_L$ CDR2 comprising a $V_L$ CDR2 selected from a $V_L$ of the antibody 4C10.20, and a $V_L$ CDR2 selected from a $V_L$ of the antibody 4C10.20.

Aspect 30. A variable light chain ($V_L$) polypeptide encoded by the nucleic acid of aspect 29.

Aspect 31. The isolated antibody of aspect 1, wherein said antibody comprises: a) a variable heavy chain (VH) polypeptide comprising a $V_H$ CDR1 of the antibody 4C10.20, a $V_H$ CDR2 of the antibody 4C10.20, and a $V_H$ CDR3 of the antibody 4C10.20; and b) a variable light chain (VL) polypeptide comprising a $V_L$ CDR1 of the antibody 4C10.20, a $V_L$ CDR2 of the antibody 4C10.20, and a $V_L$ CDR3 of the antibody 4C10.20.

Aspect 32. A kit for specifically binding to a Botulinum neurotoxin, comprising a composition of aspect 17.

Aspect 33. A method for detecting Botulinum neurotoxin in a sample, comprising: contacting an antibody of any one of aspects 1-16 with the sample, detecting binding of said antibody to Botulinum neurotoxin in said sample.

Aspect 34. The method of aspect 33, wherein said antibody is labeled.

Aspect 35. The method of aspect 33, wherein said label is a fluorescent label, a chemiluminescent label, a radiolabel, an enzyme, or a chromogenic label.

Aspect 36. The method of aspect 33, wherein said sample is blood.

Aspect 37. The method of aspect 33, wherein said antibody is immobilized on a substrate.

Aspect 38. The method of aspect 33, wherein said antibody is conjugated to a nucleic acid and wherein said detecting comprises a polymerase chain reaction.

Aspect 39. A method of reducing the likelihood that an individual at risk of exposure to Botulinum neurotoxin will experience symptoms of Botulinum neurotoxin poisoning following exposure, the method comprising administering to said individual an effective amount of an antibody of any one of aspects 1-16; wherein said administering provides for reducing the likelihood that the individual will experience symptoms of Botulinum neurotoxin poisoning.

EXAMPLES

The following examples are offered to illustrate, but not to limit any embodiments provided by the present disclosure.

Overview

The antibody 4C10.5 was isolated from yeast display libraries in the laboratory of Dr. James Marks at the University of California at San Francisco. During affinity-maturation in the same laboratory, three amino acid changes were made in the light chain and in the heavy to generate the antibody 4C10.20.

Example 1: Construction of the 4C10.20 Expression Plasmids

Source of the Original Anti-BoNT/C Antibody

The precursor to 4C10.20, 4C10.5, was isolated from yeast display libraries in the laboratory of Dr. James Marks at the University of California at San Francisco. During affinity-maturation in the same laboratory, three amino acid changes were made in the light chain and one in the heavy chain to generate the final antibody 4C10.20, also used interchangeably herein as "XC41" and "4C10.5.20". DNAs encoding the 4C10.20 light chain and heavy chain variable (V) region domains were codon-optimized for CHO-K1 cells, synthesized, and fused to Human Kappa and Gamma-1 constant regions, respectively. The resulting expressed antibody product was 4C10.20.

Description of the 4C10.20 Expression Plasmid pMXN248

The plasmid pMXN248 was constructed to direct the expression of 4C10.20 in CHO-K1 cells. These expression plasmids contained the light chain (LC) and heavy chain (HC) of 4C10.20 each under control of the human cytomegalovirus (hCMV) immediate early promoter. The hCMV promoter was followed by an intron comprised of the splice donor sequence from the hCMV promoter and a splice acceptor sequence from the SV40 16S intron. DNA encoding the mouse LC polyadenylation (poly A) sequence followed the 3' end of gene sequences encoding 4C10.20 LC and HC. The secretion signal sequences were chosen based on the closest matches of the 4C10.20 LC and HC V region sequences with the corresponding human germline LC and HC, respectively. Other elements common to both plasmids included the chicken lysozyme matrix attachment region (CL MAR), an origin of replication (ori) from the plasmid pBR322, which allows replication of the plasmid in E. coli, and the beta lactamase gene (bla), which confers ampicillin resistance in E. coli.

The plasmid pMXN248 contained the neomycin phosphotransferase (neo) gene which encodes resistance to the antibiotic, Geneticin® (G418) (Southern and Berg, 1982). In medium containing Geneticin®, only cells expressing the neo gene survive. The neo selective marker gene in this plasmid was under control of the SV40 early region promoter and polyA sequences. pMXN248 also contained two copies of the CL MAR to promote better position-independent expression.

Example 2: Evaluation of 4C10 Variants of Human Antibodies

Tables 2, 3, and 4 display information for the candidate antibody variants. Affinities for C and DC, and CHO-K1 manufacturability also are shown in Table 2. CHO-K1 manufacturability represents relative expression within each experiment relative to the XB10 control. Relative expression for LC:HC and 1:1 and 2:1 ratios are shown.

TABLE 2

Affinities for 4C10 antibody variants (IgG by KinExA)

| Antibody | BoNT/C (pM) | IgG-Kd (pM) BoNT D/C | CHO-K1 Mfg |
|---|---|---|---|
| 4C10.5 | 65.1 | 986.8 | 32/19 |
| 4C10.8 | 3.5 | 56.44 | 22/10 |
| 4C10.15 | 12.19 | 112.22 | 24/11 |
| 4C10.17 | 32.47 | 766.07 | 33/17 |

TABLE 2-continued

Affinities for 4C10 antibody variants (IgG by KinExA)

| Antibody | BoNT/C (pM) | IgG-Kd (pM) BoNT D/C | CHO-K1 Mfg |
|---|---|---|---|
| 4C10.18 | 10.82 | 108.7 | 21/7 |
| 4C10.20 | 1.02 | 16.6 | 21/18; 93/177 |
| 4C10.22 | 1.92 | 60.39 | 15/3 |
| 4C10.23 | 6.65 | 90.38 | 21/11; 88/93 |

TABLE 3

Affinities with respect to wt (4C10.5) control KD for 4C10 antibody variants. Yeast displayed scFV

| Clone | Clone KD/ wt KD C nM | Clone KD/ wt KD DC nM |
|---|---|---|
| 4C10.8 | 1.13/6.37 | 4.25/17.55 |
| 4C10.15 | 2.17/6.37 | 5.16/17.55 |
| 4C10.17 | 1.71/6.37 |

The original codon optimized heavy chain from Blue Heron was designated as BH. Expression levels are relative to XB10 at 1:1 which is set at 100. The highest expression for each antibody is shown in red. XB10 and XB23 antibodies were previously selected at Dr Marks Lab and both antibodies are BoNT/B specific, which were used only as expression controls.

Example 3: Evaluation of 4C10.5 variants of human antibodies in yeast cells

Study results of 4C10.5 and variants 4C10.8, 4C10.15, 4C10.17, 4C10.18, 4C10.20, and 4C10.22, showed that all of the antibodies tested displayed positive staining within subsets of the positive control yeast cells and negative staining of the negative control yeast cells at a concentration of 1 μg/mL. At 0.1 and 0.01 μg/mL, all antibodies tested were negative for staining in both the positive and negative control yeast cell lines.

Example 4: Thermal, physical, and chemical evaluation of 4C10.20 and 4C10.23 antibodies This study evaluated candidate Botulism Type C and DC antibodies for solubility as well as thermal, physical and chemical stability. The minimum solubility requirement was 10 mg/mL in the BoNT/A target formulation (10 mM NaSuccinate/Succinic Acid, 142mM L-arginine, pH 6.0). Candidate antibodies in the target formulation were analyzed using differential scanning calorimetry to obtain comparative thermal stability. The mAbs were also assessed for physical stability with and without surfactant (0.005% PS80) by agitation and freeze/thaw. Limited chemical stability was initiated at 40° C. and 50° C. to obtain general degradation patterns and to enable development of stability-indicating analytical methods.

The 4C10.20 and 4C10.23 antibodies achieved a solubility of 10 mg/mL or greater in the target formulation without polysorbate 80. Aggregate levels did not increase significantly for either candidate pre (1 mg/mL) versus post concentration (>10 mg/mL). Table 16 shows relevant concentration and percent aggregate data.

TABLE 6

Solubility data for 4C10.5 candidate antibodies.

| | Protein concentration (mg/ml) | | % Aggregate by SEC-HPLC | |
|---|---|---|---|---|
| mAb | Starting [ ] | Ending [ ] | Starting % | Ending % |
| 4C10.20 | 4.4 | 24.0 | 0.56 | 0.73 |
| 4C10.23 | 4.3 | 29.5 | 0.07 | 0.05 |

One useful biophysical method for screening different formulation conditions was high sensitivity differential scanning calorimetry (DSC). As the temperature in the cell is increased, the protein starts to unfold from the native state to the denatured state, exhibiting one or more onset transition temperature(s) (To) and transition temperature of maximum heat capacity (Tms). Although these temperatures are primary indicators of the thermal stability of each protein in a given formulation environment, they may not be predictive of long-term storage stability. The candidate antibodies were dialyzed into the target formulation and protein concentrations were adjusted to 2 mg/ml for DSC analysis.

The 4C10.23 antibody was slightly more thermally stable than 4C10.20. 4C10.23 had a higher main transition (~83° C.) but did not have a well resolved Fab transition. 4C10.20's main transition was 75° C., but the Fab transition was 83° C. Both 4C10.20 and 4C10.23 antibodies that were assessed were formulated at 1 mg/ml in the target formulation both with and without surfactant (0.005% polysorbate 80) to determine if any physical stability sensitivity existed. 4C10.20 showed a large initial increase in A350 measurement after the first thaw. Regardless of the addition of polysorbate 80 as a physical stabilizer, light scattering did not increase across subsequent FT cycles. Unlike 4C10.20, the light scattering increase did not occur for 4C10.23. There were no significant increases in percent aggregate and no losses in total protein for either antibody during freeze/thaw stress.

Limited short-term chemical stability at 40° C. was performed on transient candidates to determine susceptibility to aggregation and also to determine if any unusual charge-based change was occurring. No instability was shown by the 4C10.20 and 4C10.23 antibodies. Short term stability at 50° C. was also performed to elucidate degradation mechanisms such as aggregation (FIG. 5). 4C10.20 showed slight decreases in percent aggregate at 40° and 50° C. In contrast, 4C10.23 showed no aggregates at time zero and no aggregate formation through the four week time point. Both antibodies showed normal clip formation. There were no significant losses in total protein and no significant increases in A350 light scattering for samples stored at accelerated temperature. 4C10.20 and 4C10.23 both showed typical charge-based shifts from basic and main to more acidic species; 4C10.23 had a slightly higher rate of change than 4C10.20.

Example 5: Amino Acid Sequences of VH and VL Chain CDRs for 4C10 Variants

TABLE 7

Amino acid sequence of VH CDRs of 4C10.5 and variant antibodies

| mAb | CDR1 (VH) | CDR2 (VH) | CDR3 (VH) |
|---|---|---|---|
| 4C10.5 | GFDMH (SEQ ID NO: 4) | RISHDGSMADYADSLRG (SEQ ID NO: 6) | DRWRSGSYPAFEI (SEQ ID NO: 8) |
| 4C10.8 | GFDMH (SEQ ID NO: 4) | RISHDGSMADYADSLRG (SEQ ID NO: 6) | DPWRSGSYPAFEI (SEQ ID NO: 9) |
| 4C10.15 | GFDMH (SEQ ID NO: 4) | RISHDGSMADYADSLRG (SEQ ID NO: 6) | DRWRSGSYPAFEI (SEQ ID NO: 8) |
| 4C10.17 | GFDMH (SEQ ID NO: 4) | RISHDGSMADYADSLRG (SEQ ID NO: 6) | DRWRSGSYPAFEI (SEQ ID NO: 8) |
| 4C10.18 | GFDMH (SEQ ID NO: 4) | RISHDGSMADYADSLRG (SEQ ID NO: 6) | DRWRSGSYPAFEI (SEQ ID NO: 8) |
| 4C10.20 | GFDMH (SEQ ID NO: 4) | RISHDGSMADYADSLRG (SEQ ID NO: 6) | DPWRSGSYPAFEI (SEQ ID NO: 9) |

TABLE 7-continued

Amino acid sequence of VH CDRs of 4C10.5 and variant antibodies

| mAb | CDR1 (VH) | CDR2 (VH) | CDR3 (VH) |
|---|---|---|---|
| 4C10.22 | GFDMH (SEQ ID NO: 4) | RISHDGSMADYADSLRG (SEQ ID NO: 6) | DPWRSGSYPAFEI (SEQ ID NO: 9) |

TABLE 8

Amino acid sequence of VL CDRs of 4C10.5 and variant antibodies

| mAb | CDR1 (VL) | CDR2 (VL) | CDR3 (VL) |
|---|---|---|---|
| 4C10.5 | RASQGISNRLA (SEQ ID NO: 13) | ASTLQS (SEQ ID NO: 18) | QQANSFPLT (SEQ ID NO: 21) |
| 4C10.8 | RASQGISNRLA (SEQ ID NO: 13) | ASTLQS (SEQ ID NO: 18) | QQANSFPLT (SEQ ID NO: 21) |
| 4C10.15 | RASKGIGNRLA (SEQ ID NO: 14) | ASTLQS (SEQ ID NO: 18) | QQANSFPLT (SEQ ID NO: 21) |
| 4C10.17 | RASQGISNRLA (SEQ ID NO: 13) | ASSLQS (SEQ ID NO: 19) | QQANSFPLT (SEQ ID NO: 21) |
| 4C10.18 | RASQGIGNRLA (SEQ ID NO: 15) | ASTLQS (SEQ ID NO: 18) | QQAHRFPLT (SEQ ID NO: 22) |
| 4C10.20 | RASQGIGNRLA (SEQ ID NO: 15) | ASTLQS (SEQ ID NO: 18) | QQANSFPLT (SEQ ID NO: 21) |
| 4C10.22 | RASQGISNRLA (SEQ ID NO: 13) | ASTLQS (SEQ ID NO: 18) | QQANSFPLT (SEQ ID NO: 21) |

TABLE 9

Select mAbs specific for BoNT/C, BoNT/D, BoNT/CD or BoNT/DC from human libraries. Clone name, library source, VH CDR3 sequence, epitope overlapping with known antibodies for BoNT/C, equilibrium dissociation constant ($K_D$) for BoNT/C and cross reactivity with BoNT/C, BoNT/CD, BoNT/DC and BoNT/D subtypes are shown. scFv $K_D$ measured on yeast displayed scFv. + means the lead scFv has good binding with the tested subtype; − means the lead does not react with the tested subtype at the maximum concentration used for testing (~1 μM).

| Clone Name | Library source | KD nM | Domain Speci- ficity | Epitope Overlap with | Cross-reactivity C1 | CD | D | DC |
|---|---|---|---|---|---|---|---|---|
| 4C10 D12 | | 0.39 | DRWRSGSYPAFEK (SEQ ID NO: 40) | LC | + | + | + | + |

TABLE 10

Characteristics of yeast displayed scFv for BoNT/C; BoNT/CD; BoNT/DC; and BoNT/D. ScFv $K_D$ measured on yeast displayed scFv. + means the scFv has good binding with the tested serotype or mosaic; − means the scFv does not react with the tested serotype or mosiac at the maximum concentration used for testing (~1 μM).

| Clone | Epitope | VH CDR3 Sequence | BoNT ScFv KD by FACS ($\times 10^{-9}$ M$^{-1}$) C1 | CD | DC | D |
|---|---|---|---|---|---|---|
| 4C10 | LC1 | DRWRSGSYPAFEK (SEQ ID NO: 40) | 1.1 | + | 107 | + |
| 4C10.1 | LC1 | DRWRSGSYPAFEI (SEQ ID NO: 8) | 0.45 | + | + | + |
| 4C10.2 | LC1 | DRWRSGSYPAFEK (SEQ ID NO: 40) | 0.27 | + | 0.89 | + |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

While the subject antibody, method, and composition have been particularly shown and described with references to preferred embodiments thereof, it will be understood by those skilled in the art that various changes in form and details may be made therein without departing from the scope of the invention encompassed by the appended claims.

What is claimed is:

1. An isolated antibody that binds to a Botulinum neurotoxin serotype BoNT/C, wherein the antibody comprises:
   a) a light chain variable region comprising, from amino terminus to carboxy terminus, a first framework region, a light chain CDR1 comprising the amino acid sequence set forth in SEQ ID NO: 15, a second framework region, a light chain CDR2 comprising the amino acid sequence set forth in SEQ ID NO: 18, a third framework region, a light chain CDR3 comprising the amino acid sequence set forth in SEQ ID NO: 21, and a fourth framework region; and
   b) a heavy chain variable region comprising, from amino terminus to carboxy terminus, a first framework region, a heavy chain CDR1 comprising the amino acid sequence set forth in SEQ ID NO: 4, a second framework region, a heavy chain CDR2 comprising the amino acid sequence set forth in SEQ ID NO: 6, a third framework region, a heavy chain CDR3 comprising the amino acid sequence set forth in SEQ ID NO: 9, and a fourth framework region.

2. The isolated antibody of claim 1, wherein said antibody comprises a full length VH comprising the amino acid sequence set forth in SEQ ID NO: 26.

3. The isolated antibody of claim 1, wherein the antibody comprises a full length $V_L$ comprising the amino acid sequence set forth in SEQ ID NO:36.

4. The isolated antibody of claim 1, wherein the antibody comprises:
   a full length $V_H$ comprising the amino acid sequence set forth in SEQ ID NO:26; and
   a full length $V_L$ comprising the amino acid sequence set forth in SEQ ID NO:36.

5. A composition comprising:
   a pharmaceutically acceptable carrier; and
   an antibody according to claim 4.

6. A kit comprising:
   an antibody according to claim 4; and
   a buffer.

7. A syringe comprising:
   an antibody according to claim 4.

8. The isolated antibody of claim 1, wherein said antibody is a human antibody or a humanized antibody.

9. The isolated antibody of claim 1, wherein said antibody is a single chain variable fragment (scFv), an IgG antibody, an antigen binding fragment (Fab), a $(Fab')_2$, or a $(scFv')_2$.

10. A composition comprising:
    a pharmaceutically acceptable carrier; and
    an antibody according to claim 1.

11. A method of specifically binding to a Botulinum neurotoxin serotype BoNT/C in a mammal comprising:
    administering to said mammal an effective amount of the antibody of claim 1;
    wherein said administering provides for specific binding of Botulinum neurotoxin serotype BoNT/C present in the mammal.

12. A method of specifically binding to a Botulinum neurotoxin serotype BoNT/C in a mammal, comprising:
    administering to said mammal an effective amount of the composition of claim 10;
    wherein said administering provides for specific binding of Botulinum neurotoxin serotype BoNT/C present in the mammal.

13. A kit comprising:
    an antibody according to claim 1; and
    a buffer.

14. A syringe comprising:
    an antibody according to claim 1.

* * * * *

SEQUENCE LISTING

<160> NUMBER OF SEQ ID NOS: 50

<210> SEQ ID NO 1

```
<211> LENGTH: 30
<212> TYPE: PRT
<213> ORGANISM: Artificial Sequence
<220> FEATURE:
<223> OTHER INFORMATION: Synthetic sequence

<400> SEQUENCE: 1

Gln Val Gln Leu Val Gln Ser Gly Gly Gly Val Val Gln Pro Gly Arg
1               5                   10                  15

Ser Leu Arg Leu Ser Cys Gly Ala Ser Arg Phe Thr Phe Ser
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: Synthetic sequence

<400> SEQUENCE: 2

Gln Val Gln Leu Val Gln Ser Gly Gly Gly Val Ala Gln Pro Gly Arg
1               5                   10                  15

Ser Leu Arg Leu Ser Cys Gly Ala Ser Arg Phe Thr Phe Ser
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: Synthetic sequence

<400> SEQUENCE: 3

Gln Val Gln Leu Val Gln Ser Gly Gly Gly Val Val Gln Pro Gly Arg
1               5                   10                  15

Ser Leu Arg Leu Ser Cys Gly Ala Ser Gly Phe Lys Phe Ser
            20                  25                  30

<210> SEQ ID NO 4
<211> LENGTH: 5
<212> TYPE: PRT
<213> ORGANISM: Artificial Sequence
<220> FEATURE:
<223> OTHER INFORMATION: Synthetic sequence

<400> SEQUENCE: 4

Gly Phe Asp Met His
1               5

<210> SEQ ID NO 5
<211> LENGTH: 14
<212> TYPE: PRT
<213> ORGANISM: Artificial Sequence
<220> FEATURE:
<223> OTHER INFORMATION: Synthetic sequence

<400> SEQUENCE: 5

Trp Val Arg Gln Ala Pro Gly Lys Gly Leu Glu Trp Val Ala
1               5                   10

<210> SEQ ID NO 6
<211> LENGTH: 17
<212> TYPE: PRT
<213> ORGANISM: Artificial Sequence
<220> FEATURE:
<223> OTHER INFORMATION: Synthetic sequence
```

-continued

```
<400> SEQUENCE: 6

Arg Ile Ser His Asp Gly Ser Met Ala Asp Tyr Ala Asp Ser Leu Arg
1               5                   10                  15

Gly

<210> SEQ ID NO 7
<211> LENGTH: 32
<212> TYPE: PRT
<213> ORGANISM: Artificial Sequence
<220> FEATURE:
<223> OTHER INFORMATION: Synthetic sequence

<400> SEQUENCE: 7

Arg Phe Thr Ile Ser Arg Asp Asn Ser Lys Asn Thr Leu Tyr Leu Gln
1               5                   10                  15

Met Asn Ser Leu Arg Val Glu Asp Thr Ala Leu Tyr Tyr Cys Ala Lys
            20                  25                  30

<210> SEQ ID NO 8
<211> LENGTH: 13
<212> TYPE: PRT
<213> ORGANISM: Artificial Sequence
<220> FEATURE:
<223> OTHER INFORMATION: Synthetic sequence

<400> SEQUENCE: 8

Asp Arg Trp Arg Ser Gly Ser Tyr Pro Ala Phe Glu Ile
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic sequence

<400> SEQUENCE: 9

Asp Pro Trp Arg Ser Gly Ser Tyr Pro Ala Phe Glu Ile
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic sequence

<400> SEQUENCE: 10

Trp Gly Gln Gly Thr Met Val Thr Val Ser Ser
1               5                   10

<210> SEQ ID NO 11
<211> LENGTH: 23
<212> TYPE: PRT
<213> ORGANISM: Artificial Sequence
<220> FEATURE:
<223> OTHER INFORMATION: Synthetic sequence

<400> SEQUENCE: 11

Glu Ile Val Leu Thr Gln Ser Pro Ser Phe Leu Ser Ala Phe Val Gly
1               5                   10                  15

Asp Arg Ile Thr Ile Thr Cys
            20
```

<210> SEQ ID NO 12
<211> LENGTH: 23
<212> TYPE: PRT
<213> ORGANISM: Artificial Sequence
<220> FEATURE:
<223> OTHER INFORMATION: Synthetic sequence

<400> SEQUENCE: 12

Glu Ile Val Leu Thr Gln Ser Pro Ser Phe Leu Ser Ala Phe Ile Gly
1               5                   10                  15

Asp Arg Ile Thr Ile Thr Cys
            20

<210> SEQ ID NO 13
<211> LENGTH: 11
<212> TYPE: PRT
<213> ORGANISM: Artificial Sequence
<220> FEATURE:
<223> OTHER INFORMATION: Synthetic sequence

<400> SEQUENCE: 13

Arg Ala Ser Gln Gly Ile Ser Asn Arg Leu Ala
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic sequence

<400> SEQUENCE: 14

Arg Ala Ser Lys Gly Ile Gly Asn Arg Leu Ala
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Synthetic sequence

<400> SEQUENCE: 15

Arg Ala Ser Gln Gly Ile Gly Asn Arg Leu Ala
1               5                   10

<210> SEQ ID NO 16
<211> LENGTH: 16
<212> TYPE: PRT
<213> ORGANISM: Artificial Sequence
<220> FEATURE:
<223> OTHER INFORMATION: Synthetic sequence

<400> SEQUENCE: 16

Trp Tyr Gln Gln Lys Pro Gly Lys Ala Pro Asn Leu Leu Ile His Pro
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Synthetic sequence

<400> SEQUENCE: 17

Trp Tyr Gln Gln Lys Pro Gly Lys Ala Pro Asn Leu Leu Ile Tyr Pro

<210> SEQ ID NO 18
<211> LENGTH: 6
<212> TYPE: PRT
<213> ORGANISM: Artificial Sequence
<220> FEATURE:
<223> OTHER INFORMATION: Synthetic sequence

<400> SEQUENCE: 18

Ala Ser Thr Leu Gln Ser
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic sequence

<400> SEQUENCE: 19

Ala Ser Ser Leu Gln Ser
1               5

<210> SEQ ID NO 20
<211> LENGTH: 32
<212> TYPE: PRT
<213> ORGANISM: Artificial Sequence
<220> FEATURE:
<223> OTHER INFORMATION: Synthetic sequence

<400> SEQUENCE: 20

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 21
<211> LENGTH: 9
<212> TYPE: PRT
<213> ORGANISM: Artificial Sequence
<220> FEATURE:
<223> OTHER INFORMATION: Synthetic sequence

<400> SEQUENCE: 21

Gln Gln Ala Asn Ser Phe Pro Leu Thr
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic sequence

<400> SEQUENCE: 22

Gln Gln Ala His Arg Phe Pro Leu Thr
1               5

<210> SEQ ID NO 23
<211> LENGTH: 122
<212> TYPE: PRT
<213> ORGANISM: Artificial Sequence
<220> FEATURE:
<223> OTHER INFORMATION: Synthetic sequence

<400> SEQUENCE: 23

Gln Val Gln Leu Val Gln Ser Gly Gly Gly Val Val Gln Pro Gly Arg
1               5                   10                  15

Ser Leu Arg Leu Ser Cys Gly Ala Ser Arg Phe Thr Phe Ser Gly Phe
            20                  25                  30

Asp Met His Trp Val Arg Gln Ala Pro Gly Lys Gly Leu Glu Trp Val
            35                  40                  45

Ala Arg Ile Ser His Asp Gly Ser Met Ala Asp Tyr Ala Asp Ser Leu
        50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Leu Tyr Tyr Cys
                85                  90                  95

Ala Lys Asp Arg Trp Arg Ser Gly Ser Tyr Pro Ala Phe Glu Ile Trp
            100                 105                 110

Gly Gln Gly Thr Met Val Thr Val Ser Ser
        115                 120

<210> SEQ ID NO 24
<211> LENGTH: 108
<212> TYPE: PRT
<213> ORGANISM: Artificial Sequence
<220> FEATURE:
<223> OTHER INFORMATION: Synthetic sequence

<400> SEQUENCE: 24

Glu Ile Val Leu Thr Gln Ser Pro Ser Phe Leu Ser Ala Phe Val Gly
1               5                   10                  15

Asp Arg Ile Thr Ile Thr Cys Arg Ala Ser Gln Gly Ile Ser Asn Arg
            20                  25                  30

Leu Ala Trp Tyr Gln Gln Lys Pro Gly Lys Ala Pro Asn Leu Leu Ile
            35                  40                  45

His Pro Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys Arg
            100                 105

<210> SEQ ID NO 25
<211> LENGTH: 230
<212> TYPE: PRT
<213> ORGANISM: Artificial Sequence
<220> FEATURE:
<223> OTHER INFORMATION: Synthetic sequence

<400> SEQUENCE: 25

Gln Val Gln Leu Val Gln Ser Gly Gly Gly Val Val Gln Pro Gly Arg
1               5                   10                  15

Ser Leu Arg Leu Ser Cys Gly Ala Ser Arg Phe Thr Phe Ser Gly Phe
            20                  25                  30

Asp Met His Trp Val Arg Gln Ala Pro Gly Lys Gly Leu Glu Trp Val
            35                  40                  45

Ala Arg Ile Ser His Asp Gly Ser Met Ala Asp Tyr Ala Asp Ser Leu
        50                  55                  60

Arg Gly Arg Phe Thr Ile Ser Arg Asp Asn Ser Lys Asn Thr Leu Tyr

```
                65                  70                  75                  80
Leu Gln Met Asn Ser Leu Arg Val Glu Asp Thr Ala Leu Tyr Tyr Cys
                    85                  90                  95

Ala Lys Asp Arg Trp Arg Ser Gly Ser Tyr Pro Ala Phe Glu Ile Trp
                100                 105                 110

Gly Gln Gly Thr Met Val Thr Val Ser Ser Glu Ile Val Leu Thr Gln
                115                 120                 125

Ser Pro Ser Phe Leu Ser Ala Phe Val Gly Asp Arg Ile Thr Ile Thr
            130                 135                 140

Cys Arg Ala Ser Gln Gly Ile Ser Asn Arg Leu Ala Trp Tyr Gln Gln
145                 150                 155                 160

Lys Pro Gly Lys Ala Pro Asn Leu Leu Ile His Pro Ala Ser Thr Leu
                165                 170                 175

Gln Ser Gly Val Pro Ser Arg Phe Ser Gly Ser Gly Ser Gly Thr Asp
                180                 185                 190

Phe Thr Leu Thr Ile Ser Ser Leu Gln Pro Glu Asp Phe Ala Thr Tyr
                195                 200                 205

Tyr Cys Gln Gln Ala Asn Ser Phe Pro Leu Thr Phe Gly Gly Gly Thr
            210                 215                 220

Lys Val Glu Ile Lys Arg
225                 230

<210> SEQ ID NO 26
<211> LENGTH: 122
<212> TYPE: PRT
<213> ORGANISM: Artificial Sequence
<220> FEATURE:
<223> OTHER INFORMATION: Synthetic sequence

<400> SEQUENCE: 26

Gln Val Gln Leu Val Gln Ser Gly Gly Gly Val Val Gln Pro Gly Arg
1               5                   10                  15

Ser Leu Arg Leu Ser Cys Gly Ala Ser Arg Phe Thr Phe Ser Gly Phe
                20                  25                  30

Asp Met His Trp Val Arg Gln Ala Pro Gly Lys Gly Leu Glu Trp Val
            35                  40                  45

Ala Arg Ile Ser His Asp Gly Ser Met Ala Asp Tyr Ala Asp Ser Leu
        50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Leu Tyr Tyr Cys
                    85                  90                  95

Ala Lys Asp Pro Trp Arg Ser Gly Ser Tyr Pro Ala Phe Glu Ile Trp
                100                 105                 110

Gly Gln Gly Thr Met Val Thr Val Ser Ser
                115                 120

<210> SEQ ID NO 27
<211> LENGTH: 108
<212> TYPE: PRT
<213> ORGANISM: Artificial Sequence
<220> FEATURE:
<223> OTHER INFORMATION: Synthetic sequence

<400> SEQUENCE: 27

Glu Ile Val Leu Thr Gln Ser Pro Ser Phe Leu Ser Ala Phe Ile Gly
1               5                   10                  15
```

```
Asp Arg Ile Thr Ile Thr Cys Arg Ala Ser Gln Gly Ile Ser Asn Arg
            20                  25                  30

Leu Ala Trp Tyr Gln Gln Lys Pro Gly Lys Ala Pro Asn Leu Leu Ile
        35                  40                  45

Tyr Pro Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys Arg
            100                 105
```

<210> SEQ ID NO 28
<211> LENGTH: 230
<212> TYPE: PRT
<213> ORGANISM: Artificial Sequence
<220> FEATURE:
<223> OTHER INFORMATION: Synthetic sequence

<400> SEQUENCE: 28

```
Gln Val Gln Leu Val Gln Ser Gly Gly Gly Val Val Gln Pro Gly Arg
1               5                   10                  15

Ser Leu Arg Leu Ser Cys Gly Ala Ser Arg Phe Thr Phe Ser Gly Phe
            20                  25                  30

Asp Met His Trp Val Arg Gln Ala Pro Gly Lys Gly Leu Glu Trp Val
        35                  40                  45

Ala Arg Ile Ser His Asp Gly Ser Met Ala Asp Tyr Ala Asp Ser Leu
50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Leu Tyr Tyr Cys
                85                  90                  95

Ala Lys Asp Pro Trp Arg Ser Gly Ser Tyr Pro Ala Phe Glu Ile Trp
            100                 105                 110

Gly Gln Gly Thr Met Val Thr Val Ser Ser Glu Ile Val Leu Thr Gln
        115                 120                 125

Ser Pro Ser Phe Leu Ser Ala Phe Ile Gly Asp Arg Ile Thr Ile Thr
130                 135                 140

Cys Arg Ala Ser Gln Gly Ile Ser Asn Arg Leu Ala Trp Tyr Gln Gln
145                 150                 155                 160

Lys Pro Gly Lys Ala Pro Asn Leu Leu Ile Tyr Pro Ala Ser Thr Leu
                165                 170                 175

Gln Ser Gly Val Pro Ser Arg Phe Ser Gly Ser Gly Ser Gly Thr Asp
            180                 185                 190

Phe Thr Leu Thr Ile Ser Ser Leu Gln Pro Glu Asp Phe Ala Thr Tyr
        195                 200                 205

Tyr Cys Gln Gln Ala Asn Ser Phe Pro Leu Thr Phe Gly Gly Gly Thr
210                 215                 220

Lys Val Glu Ile Lys Arg
225                 230
```

<210> SEQ ID NO 29
<211> LENGTH: 108
<212> TYPE: PRT
<213> ORGANISM: Artificial Sequence
<220> FEATURE:

<223> OTHER INFORMATION: Synthetic sequence

<400> SEQUENCE: 29

```
Glu Ile Val Leu Thr Gln Ser Pro Ser Phe Leu Ser Ala Phe Val Gly
1               5                   10                  15

Asp Arg Ile Thr Ile Thr Cys Arg Ala Ser Lys Gly Ile Gly Asn Arg
            20                  25                  30

Leu Ala Trp Tyr Gln Gln Lys Pro Gly Lys Ala Pro Asn Leu Leu Ile
        35                  40                  45

His Pro Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys Arg
            100                 105
```

<210> SEQ ID NO 30
<211> LENGTH: 230
<212> TYPE: PRT
<213> ORGANISM: Artificial Sequence
<220> FEATURE:
<223> OTHER INFORMATION: Synthetic sequence

<400> SEQUENCE: 30

```
Gln Val Gln Leu Val Gln Ser Gly Gly Gly Val Val Gln Pro Gly Arg
1               5                   10                  15

Ser Leu Arg Leu Ser Cys Gly Ala Ser Arg Phe Thr Phe Ser Gly Phe
            20                  25                  30

Asp Met His Trp Val Arg Gln Ala Pro Gly Lys Gly Leu Glu Trp Val
        35                  40                  45

Ala Arg Ile Ser His Asp Gly Ser Met Ala Asp Tyr Ala Asp Ser Leu
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Leu Tyr Tyr Cys
                85                  90                  95

Ala Lys Asp Arg Trp Arg Ser Gly Ser Tyr Pro Ala Phe Glu Ile Trp
            100                 105                 110

Gly Gln Gly Thr Met Val Thr Val Ser Ser Glu Ile Val Leu Thr Gln
        115                 120                 125

Ser Pro Ser Phe Leu Ser Ala Phe Val Gly Asp Arg Ile Thr Ile Thr
    130                 135                 140

Cys Arg Ala Ser Lys Gly Ile Gly Asn Arg Leu Ala Trp Tyr Gln Gln
145                 150                 155                 160

Lys Pro Gly Lys Ala Pro Asn Leu Leu Ile His Pro Ala Ser Thr Leu
                165                 170                 175

Gln Ser Gly Val Pro Ser Arg Phe Ser Gly Ser Gly Ser Gly Thr Asp
            180                 185                 190

Phe Thr Leu Thr Ile Ser Ser Leu Gln Pro Glu Asp Phe Ala Thr Tyr
        195                 200                 205

Tyr Cys Gln Gln Ala Asn Ser Phe Pro Leu Thr Phe Gly Gly Gly Thr
    210                 215                 220

Lys Val Glu Ile Lys Arg
225                 230
```

<210> SEQ ID NO 31
<211> LENGTH: 108
<212> TYPE: PRT
<213> ORGANISM: Artificial Sequence
<220> FEATURE:
<223> OTHER INFORMATION: Synthetic sequence

<400> SEQUENCE: 31

Glu Ile Val Leu Thr Gln Ser Pro Ser Phe Leu Ser Ala Phe Val Gly
1               5                   10                  15

Asp Arg Ile Thr Ile Thr Cys Arg Ala Ser Gln Gly Ile Ser Asn Arg
            20                  25                  30

Leu Ala Trp Tyr Gln Gln Lys Pro Gly Lys Ala Pro Asn Leu Leu Ile
        35                  40                  45

His Pro Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys Arg
            100                 105

<210> SEQ ID NO 32
<211> LENGTH: 230
<212> TYPE: PRT
<213> ORGANISM: Artificial Sequence
<220> FEATURE:
<223> OTHER INFORMATION: Synthetic sequence

<400> SEQUENCE: 32

Gln Val Gln Leu Val Gln Ser Gly Gly Gly Val Val Gln Pro Gly Arg
1               5                   10                  15

Ser Leu Arg Leu Ser Cys Gly Ala Ser Arg Phe Thr Phe Ser Gly Phe
            20                  25                  30

Asp Met His Trp Val Arg Gln Ala Pro Gly Lys Gly Leu Glu Trp Val
        35                  40                  45

Ala Arg Ile Ser His Asp Gly Ser Met Ala Asp Tyr Ala Asp Ser Leu
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Leu Tyr Tyr Cys
                85                  90                  95

Ala Lys Asp Arg Trp Arg Ser Gly Ser Tyr Pro Ala Phe Glu Ile Trp
            100                 105                 110

Gly Gln Gly Thr Met Val Thr Val Ser Ser Glu Ile Val Leu Thr Gln
        115                 120                 125

Ser Pro Ser Phe Leu Ser Ala Phe Val Gly Asp Arg Ile Thr Ile Thr
    130                 135                 140

Cys Arg Ala Ser Gln Gly Ile Ser Asn Arg Leu Ala Trp Tyr Gln Gln
145                 150                 155                 160

Lys Pro Gly Lys Ala Pro Asn Leu Leu Ile His Pro Ala Ser Ser Leu
                165                 170                 175

Gln Ser Gly Val Pro Ser Arg Phe Ser Gly Ser Gly Ser Gly Thr Asp
            180                 185                 190

Phe Thr Leu Thr Ile Ser Ser Leu Gln Pro Glu Asp Phe Ala Thr Tyr

```
            195                 200                 205
Tyr Cys Gln Ala Asn Ser Phe Pro Leu Thr Phe Gly Gly Gly Thr
    210                 215                 220

Lys Val Glu Ile Lys Arg
225                 230

<210> SEQ ID NO 33
<211> LENGTH: 122
<212> TYPE: PRT
<213> ORGANISM: Artificial Sequence
<220> FEATURE:
<223> OTHER INFORMATION: Synthetic sequence

<400> SEQUENCE: 33

Gln Val Gln Leu Val Gln Ser Gly Gly Gly Val Ala Gln Pro Gly Arg
1               5                   10                  15

Ser Leu Arg Leu Ser Cys Gly Ala Ser Arg Phe Thr Phe Ser Gly Phe
                20                  25                  30

Asp Met His Trp Val Arg Gln Ala Pro Gly Lys Gly Leu Glu Trp Val
            35                  40                  45

Ala Arg Ile Ser His Asp Gly Ser Met Ala Asp Tyr Ala Asp Ser Leu
        50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Leu Tyr Tyr Cys
                85                  90                  95

Ala Lys Asp Arg Trp Arg Ser Gly Ser Tyr Pro Ala Phe Glu Ile Trp
            100                 105                 110

Gly Gln Gly Thr Met Val Thr Val Ser Ser
        115                 120

<210> SEQ ID NO 34
<211> LENGTH: 108
<212> TYPE: PRT
<213> ORGANISM: Artificial Sequence
<220> FEATURE:
<223> OTHER INFORMATION: Synthetic sequence

<400> SEQUENCE: 34

Glu Ile Val Leu Thr Gln Ser Pro Ser Phe Leu Ser Ala Phe Val Gly
1               5                   10                  15

Asp Arg Ile Thr Ile Thr Cys Arg Ala Ser Gln Gly Ile Gly Asn Arg
                20                  25                  30

Leu Ala Trp Tyr Gln Gln Lys Pro Gly Lys Ala Pro Asn Leu Leu Ile
            35                  40                  45

His Pro Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala His Arg Phe Pro Leu
                85                  90                  95

Thr Phe Gly Gly Gly Thr Lys Val Glu Ile Lys Arg
            100                 105

<210> SEQ ID NO 35
<211> LENGTH: 230
<212> TYPE: PRT
<213> ORGANISM: Artificial Sequence
<220> FEATURE:
```

<223> OTHER INFORMATION: Synthetic sequence

<400> SEQUENCE: 35

```
Gln Val Gln Leu Val Gln Ser Gly Gly Gly Val Ala Gln Pro Gly Arg
1               5                   10                  15
Ser Leu Arg Leu Ser Cys Gly Ala Ser Arg Phe Thr Phe Ser Gly Phe
            20                  25                  30
Asp Met His Trp Val Arg Gln Ala Pro Gly Lys Gly Leu Glu Trp Val
        35                  40                  45
Ala Arg Ile Ser His Asp Gly Ser Met Ala Asp Tyr Ala Asp Ser Leu
    50                  55                  60
Arg Gly Arg Phe Thr Ile Ser Arg Asp Asn Ser Lys Asn Thr Leu Tyr
65                  70                  75                  80
Leu Gln Met Asn Ser Leu Arg Val Glu Asp Thr Ala Leu Tyr Tyr Cys
                85                  90                  95
Ala Lys Asp Arg Trp Arg Ser Gly Ser Tyr Pro Ala Phe Glu Ile Trp
            100                 105                 110
Gly Gln Gly Thr Met Val Thr Val Ser Ser Glu Ile Val Leu Thr Gln
        115                 120                 125
Ser Pro Ser Phe Leu Ser Ala Phe Val Gly Asp Arg Ile Thr Ile Thr
    130                 135                 140
Cys Arg Ala Ser Gln Gly Ile Gly Asn Arg Leu Ala Trp Tyr Gln Gln
145                 150                 155                 160
Lys Pro Gly Lys Ala Pro Asn Leu Leu Ile His Pro Ala Ser Thr Leu
                165                 170                 175
Gln Ser Gly Val Pro Ser Arg Phe Ser Gly Ser Gly Ser Gly Thr Asp
            180                 185                 190
Phe Thr Leu Thr Ile Ser Ser Leu Gln Pro Glu Asp Phe Ala Thr Tyr
        195                 200                 205
Tyr Cys Gln Gln Ala His Arg Phe Pro Leu Thr Phe Gly Gly Gly Thr
    210                 215                 220
Lys Val Glu Ile Lys Arg
225                 230
```

<210> SEQ ID NO 36
<211> LENGTH: 108
<212> TYPE: PRT
<213> ORGANISM: Artificial Sequence
<220> FEATURE:
<223> OTHER INFORMATION: Synthetic sequence

<400> SEQUENCE: 36

```
Glu Ile Val Leu Thr Gln Ser Pro Ser Phe Leu Ser Ala Phe Ile Gly
1               5                   10                  15
Asp Arg Ile Thr Ile Thr Cys Arg Ala Ser Gln Gly Ile Gly Asn Arg
            20                  25                  30
Leu Ala Trp Tyr Gln Gln Lys Pro Gly Lys Ala Pro Asn Leu Leu Ile
        35                  40                  45
Tyr Pro Ala Ser Thr Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ala Asn Ser Phe Pro Leu
                85                  90                  95
Thr Phe Gly Gly Gly Thr Lys Val Glu Ile Lys Arg
            100                 105
```

<210> SEQ ID NO 37
<211> LENGTH: 230
<212> TYPE: PRT
<213> ORGANISM: Artificial Sequence
<220> FEATURE:
<223> OTHER INFORMATION: Synthetic sequence

<400> SEQUENCE: 37

```
Gln Val Gln Leu Val Gln Ser Gly Gly Gly Val Val Gln Pro Gly Arg
1               5                   10                  15

Ser Leu Arg Leu Ser Cys Gly Ala Ser Arg Phe Thr Phe Ser Gly Phe
            20                  25                  30

Asp Met His Trp Val Arg Gln Ala Pro Gly Lys Gly Leu Glu Trp Val
        35                  40                  45

Ala Arg Ile Ser His Asp Gly Ser Met Ala Asp Tyr Ala Asp Ser Leu
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Leu Tyr Tyr Cys
                85                  90                  95

Ala Lys Asp Pro Trp Arg Ser Gly Ser Tyr Pro Ala Phe Glu Ile Trp
            100                 105                 110

Gly Gln Gly Thr Met Val Thr Val Ser Ser Glu Ile Val Leu Thr Gln
        115                 120                 125

Ser Pro Ser Phe Leu Ser Ala Phe Ile Gly Asp Arg Ile Thr Ile Thr
    130                 135                 140

Cys Arg Ala Ser Gln Gly Ile Gly Asn Arg Leu Ala Trp Tyr Gln Gln
145                 150                 155                 160

Lys Pro Gly Lys Ala Pro Asn Leu Leu Ile Tyr Pro Ala Ser Thr Leu
                165                 170                 175

Gln Ser Gly Val Pro Ser Arg Phe Ser Gly Ser Gly Ser Gly Thr Asp
            180                 185                 190

Phe Thr Leu Thr Ile Ser Ser Leu Gln Pro Glu Asp Phe Ala Thr Tyr
        195                 200                 205

Tyr Cys Gln Gln Ala Asn Ser Phe Pro Leu Thr Phe Gly Gly Gly Thr
    210                 215                 220

Lys Val Glu Ile Lys Arg
225                 230
```

<210> SEQ ID NO 38
<211> LENGTH: 122
<212> TYPE: PRT
<213> ORGANISM: Artificial Sequence
<220> FEATURE:
<223> OTHER INFORMATION: Synthetic sequence

<400> SEQUENCE: 38

```
Gln Val Gln Leu Val Gln Ser Gly Gly Gly Val Val Gln Pro Gly Arg
1               5                   10                  15

Ser Leu Arg Leu Ser Cys Gly Ala Ser Gly Phe Lys Phe Ser Gly Phe
            20                  25                  30

Asp Met His Trp Val Arg Gln Ala Pro Gly Lys Gly Leu Glu Trp Val
        35                  40                  45

Ala Arg Ile Ser His Asp Gly Ser Met Ala Asp Tyr Ala Asp Ser Leu
    50                  55                  60

Arg Gly Arg Phe Thr Ile Ser Arg Asp Asn Ser Lys Asn Thr Leu Tyr
```

```
            65                  70                  75                  80
Leu Gln Met Asn Ser Leu Arg Val Glu Asp Thr Ala Leu Tyr Tyr Cys
                85                  90                  95

Ala Lys Asp Pro Trp Arg Ser Gly Ser Tyr Pro Ala Phe Glu Ile Trp
                100                 105                 110

Gly Gln Gly Thr Met Val Thr Val Ser Ser
                115                 120

<210> SEQ ID NO 39
<211> LENGTH: 230
<212> TYPE: PRT
<213> ORGANISM: Artificial Sequence
<220> FEATURE:
<223> OTHER INFORMATION: Synthetic sequence

<400> SEQUENCE: 39

Gln Val Gln Leu Val Gln Ser Gly Gly Gly Val Val Gln Pro Gly Arg
1               5                   10                  15

Ser Leu Arg Leu Ser Cys Gly Ala Ser Gly Phe Lys Phe Ser Gly Phe
                20                  25                  30

Asp Met His Trp Val Arg Gln Ala Pro Gly Lys Gly Leu Glu Trp Val
                35                  40                  45

Ala Arg Ile Ser His Asp Gly Ser Met Ala Asp Tyr Ala Asp Ser Leu
        50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Leu Tyr Tyr Cys
                85                  90                  95

Ala Lys Asp Pro Trp Arg Ser Gly Ser Tyr Pro Ala Phe Glu Ile Trp
                100                 105                 110

Gly Gln Gly Thr Met Val Thr Val Ser Ser Glu Ile Val Leu Thr Gln
                115                 120                 125

Ser Pro Ser Phe Leu Ser Ala Phe Ile Gly Asp Arg Ile Thr Ile Thr
        130                 135                 140

Cys Arg Ala Ser Gln Gly Ile Ser Asn Arg Leu Ala Trp Tyr Gln Gln
145                 150                 155                 160

Lys Pro Gly Lys Ala Pro Asn Leu Leu Ile Tyr Pro Ala Ser Thr Leu
                165                 170                 175

Gln Ser Gly Val Pro Ser Arg Phe Ser Gly Ser Gly Ser Gly Thr Asp
                180                 185                 190

Phe Thr Leu Thr Ile Ser Ser Leu Gln Pro Glu Asp Phe Ala Thr Tyr
                195                 200                 205

Tyr Cys Gln Gln Ala Asn Ser Phe Pro Leu Thr Phe Gly Gly Gly Thr
        210                 215                 220

Lys Val Glu Ile Lys Arg
225                 230

<210> SEQ ID NO 40
<211> LENGTH: 13
<212> TYPE: PRT
<213> ORGANISM: Artificial Sequence
<220> FEATURE:
<223> OTHER INFORMATION: Synthetic sequence

<400> SEQUENCE: 40

Asp Arg Trp Arg Ser Gly Ser Tyr Pro Ala Phe Glu Lys
1               5                   10
```

```
<210> SEQ ID NO 41
<211> LENGTH: 14
<212> TYPE: PRT
<213> ORGANISM: Artificial Sequence
<220> FEATURE:
<223> OTHER INFORMATION: Synthetic sequence

<400> SEQUENCE: 41

Ala Ala Ala Ala Ala Ala Ala Ala Ala Ala Ala Ala Ala Ala
1               5                   10

<210> SEQ ID NO 42
<211> LENGTH: 15
<212> TYPE: PRT
<213> ORGANISM: Artificial Sequence
<220> FEATURE:
<223> OTHER INFORMATION: Synthetic sequence

<400> SEQUENCE: 42

Gly Gly Gly Gly Ser Gly Gly Gly Gly Ser Gly Gly Gly Gly Ser
1               5                   10                  15

<210> SEQ ID NO 43
<211> LENGTH: 5
<212> TYPE: PRT
<213> ORGANISM: Artificial Sequence
<220> FEATURE:
<223> OTHER INFORMATION: Synthetic sequence

<400> SEQUENCE: 43

Ser Ser Ser Ser Gly
1               5

<210> SEQ ID NO 44
<211> LENGTH: 15
<212> TYPE: PRT
<213> ORGANISM: Artificial Sequence
<220> FEATURE:
<223> OTHER INFORMATION: Synthetic sequence

<400> SEQUENCE: 44

Ser Ser Ser Ser Gly Ser Ser Ser Ser Gly Ser Ser Ser Ser Gly
1               5                   10                  15

<210> SEQ ID NO 45
<211> LENGTH: 5
<212> TYPE: PRT
<213> ORGANISM: Artificial Sequence
<220> FEATURE:
<223> OTHER INFORMATION: Synthetic sequence

<400> SEQUENCE: 45

Gly Gly Gly Gly Ser
1               5

<210> SEQ ID NO 46
<211> LENGTH: 11
<212> TYPE: PRT
<213> ORGANISM: Artificial Sequence
<220> FEATURE:
<223> OTHER INFORMATION: Synthetic sequence

<400> SEQUENCE: 46

Phe Gly Gly Gly Thr Lys Val Glu Ile Lys Arg
1               5                   10
```

<210> SEQ ID NO 47
<211> LENGTH: 711
<212> TYPE: DNA
<213> ORGANISM: Artificial Sequence
<220> FEATURE:
<223> OTHER INFORMATION: Synthetic Sequence

<400> SEQUENCE: 47

```
atggacatgc gtgtgcctgc ccagcttctg gggctcttgc tcctgtggct gccaggagct    60
agatgcgaaa tcgttcttac acaatctcca tccttcctga gtgcctttat cggtgataga   120
atcacaatca cctgccgtgc ttcacagggt attggcaaca ggctggcctg gtatcagcag   180
aaacccggca agcacctaa tttgctgatc tacccaccca gtacactgca gagtggcgta    240
ccatctcgct ttagcgggtc cggctctggc actgatttta cactgaccat atcaagcctg   300
cagccagagg atttcgccac ctattattgt caacaagcaa actccttccc cctgaccttc   360
ggaggcggaa caaaagtgga gattaagcgt acggtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata cgccctcca atcgggtaac    540
tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgtta g            711
```

<210> SEQ ID NO 48
<211> LENGTH: 236
<212> TYPE: PRT
<213> ORGANISM: Artificial Sequence
<220> FEATURE:
<223> OTHER INFORMATION: Synthetic Sequence

<400> SEQUENCE: 48

```
Met Asp Met Arg Val Pro Ala Gln Leu Leu Gly Leu Leu Leu Leu Trp
 1               5                  10                  15
Leu Pro Gly Ala Arg Cys Glu Ile Val Leu Thr Gln Ser Pro Ser Phe
             20                  25                  30
Leu Ser Ala Phe Ile Gly Asp Arg Ile Thr Ile Thr Cys Arg Ala Ser
         35                  40                  45
Gln Gly Ile Gly Asn Arg Leu Ala Trp Tyr Gln Gln Lys Pro Gly Lys
     50                  55                  60
Ala Pro Asn Leu Leu Ile Tyr Pro Pro Ser Thr Leu Gln Ser Gly Val
 65                  70                  75                  80
Pro Ser Arg Phe Ser Gly Ser Gly Ser Gly Thr Asp Phe Thr Leu Thr
                 85                  90                  95
Ile Ser Ser Leu Gln Pro Glu Asp Phe Ala Thr Tyr Tyr Cys Gln Gln
            100                 105                 110
Ala Asn Ser Phe Pro Leu Thr Phe Gly Gly Gly Thr Lys Val Glu Ile
        115                 120                 125
Lys Arg Thr Val Ala Ala Pro Ser Val Phe Ile Phe Pro Pro Ser Asp
    130                 135                 140
Glu Gln Leu Lys Ser Gly Thr Ala Ser Val Val Cys Leu Leu Asn Asn
145                 150                 155                 160
Phe Tyr Pro Arg Glu Ala Lys Val Gln Trp Lys Val Asp Asn Ala Leu
                165                 170                 175
Gln Ser Gly Asn Ser Gln Glu Ser Val Thr Glu Gln Asp Ser Lys Asp
            180                 185                 190
```

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
        210                 215                 220

Ser Pro Val Thr Lys Ser Phe Asn Arg Gly Glu Cys
225                 230                 235

<210> SEQ ID NO 49
<211> LENGTH: 1416
<212> TYPE: DNA
<213> ORGANISM: Artificial Sequence
<220> FEATURE:
<223> OTHER INFORMATION: Synthetic Sequence

<400> SEQUENCE: 49

| | | | | | |
|---|---|---|---|---|---|
| atggaatttg | cctgtcctg | ggtgttcctg | gtggccctgc | tgagaggcgt | gcagtgtcag | 60 |
| gtgcagctgg | tgcagtctgg | cggcggagtg | gtgcagcctg | gaagatccct | gagactgtcc | 120 |
| tgcggcgcct | cccggttcac | cttctctggc | ttcgacatgc | actgggtgcg | acaggcccct | 180 |
| ggcaagggac | tggaatgggt | ggccagaatc | tcccacgacg | gctccatggc | cgactacgcc | 240 |
| gattccctga | gaggcagatt | caccatctcc | cgggacaact | ccaagaacac | cctgtacctg | 300 |
| cagatgaact | ccctgcgggt | ggaagatacc | gccctgtact | actgcgccaa | ggacccttgg | 360 |
| agatccggct | cctaccccgc | cttcgagatt | tggggccagg | gcacaatggt | caccgtcagc | 420 |
| tcagccagca | caaagggccc | atcggtcttc | ccctggcac | cctcctccaa | gagcacctct | 480 |
| gggggcacag | cggccctggg | ctgcctggtc | aaggactact | tccccgaacc | ggtgacggtg | 540 |
| tcgtggaact | caggcgccct | gaccagcggc | gtgcacacct | tcccggctgt | cctacagtcc | 600 |
| tcaggactct | actccctcag | cagcgtggtg | accgtgccct | ccagcagctt | gggcacccag | 660 |
| acctacatct | gcaacgtgaa | tcacaagccc | agcaacacca | aggtggacaa | gagagttgag | 720 |
| cccaaatctt | gtgacaaaac | tcacacatgt | ccaccgtgcc | cagcacctga | actcctgggg | 780 |
| ggaccgtcag | tcttcctctt | ccccccaaaa | cccaaggaca | ccctcatgat | ctcccggacc | 840 |
| cctgaggtca | catgcgtggt | ggtggacgtg | agccacgaag | accctgaggt | caagttcaac | 900 |
| tggtacgtgg | acggcgtgga | ggtgcataat | gccaagacaa | agccgcggga | ggagcagtac | 960 |
| aacagcacgt | accgtgtggt | cagcgtcctc | accgtcctgc | accaggactg | gctgaatggc | 1020 |
| aaggagtaca | agtgcaaggt | ctccaacaaa | gccctcccag | cccccatcga | gaaaaccatc | 1080 |
| tccaaagcca | aagggcagcc | ccgagaacca | caggtgtaca | ccctgcccc | atcccgggag | 1140 |
| gagatgacca | agaaccaggt | cagcctgacc | tgcctggtca | aaggcttcta | tcccagcgac | 1200 |
| atcgccgtgg | agtgggagag | caatgggcag | ccggagaaca | actacaagac | cacgcctccc | 1260 |
| gtgctggact | ccgacggctc | cttcttcctc | tatagcaagc | tcaccgtgga | caagagcagg | 1320 |
| tggcagcagg | ggaacgtctt | ctcatgctcc | gtgatgcatg | aggctctgca | caaccactac | 1380 |
| acgcagaaga | gcctctcct | gtccccgggt | aaatga | | | 1416 |

<210> SEQ ID NO 50
<211> LENGTH: 471
<212> TYPE: PRT
<213> ORGANISM: Artificial Sequence
<220> FEATURE:
<223> OTHER INFORMATION: Synthetic Sequence

<400> SEQUENCE: 50

Met Glu Phe Gly Leu Ser Trp Val Phe Leu Val Ala Leu Leu Arg Gly
1               5                   10                  15

```
Val Gln Cys Gln Val Gln Leu Val Gln Ser Gly Gly Val Val Gln
                20                  25                  30

Pro Gly Arg Ser Leu Arg Leu Ser Cys Gly Ala Ser Arg Phe Thr Phe
            35                  40                  45

Ser Gly Phe Asp Met His Trp Val Arg Gln Ala Pro Gly Lys Gly Leu
50                  55                  60

Glu Trp Val Ala Arg Ile Ser His Asp Gly Ser Met Ala Asp Tyr Ala
65                  70                  75                  80

Asp Ser Leu Arg Gly Arg Phe Thr Ile Ser Arg Asp Asn Ser Lys Asn
                85                  90                  95

Thr Leu Tyr Leu Gln Met Asn Ser Leu Arg Val Glu Asp Thr Ala Leu
            100                 105                 110

Tyr Tyr Cys Ala Lys Asp Pro Trp Arg Ser Gly Ser Tyr Pro Ala Phe
        115                 120                 125

Glu Ile Trp Gly Gln Gly Thr Met Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430
```

-continued

```
Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465             470
```